US012486236B2

(12) United States Patent
Wang et al.

(10) Patent No.: US 12,486,236 B2
(45) Date of Patent: Dec. 2, 2025

(54) ELECTROLUMINESCENT DEVICE

(71) Applicant: BEIJING SUMMER SPROUT TECHNOLOGY CO., LTD., Beijing (CN)

(72) Inventors: Le Wang, Beijing (CN); Qiang Wang, Beijing (CN); Junfei Wang, Beijing (CN); Han Zhang, Beijing (CN); Qi Zhang, Beijing (CN); Zhihong Dai, Beijing (CN); Cuifang Zhang, Beijing (CN); Nannan Lu, Beijing (CN); Chi Yuen Raymond Kwong, Beijing (CN); Chuanjun Xia, Beijing (CN)

(73) Assignee: BEIJING SUMMER SPROUT TECHNOLOGY CO., LTD., Beijing (CN)

( * ) Notice: Subject to any disclaimer, the term of this patent is extended or adjusted under 35 U.S.C. 154(b) by 798 days.

(21) Appl. No.: 17/339,222

(22) Filed: Jun. 4, 2021

(65) Prior Publication Data

US 2022/0402877 A1 Dec. 22, 2022

(30) Foreign Application Priority Data

Jun. 5, 2020 (CN) ......................... 202010505871.4
Apr. 28, 2021 (CN) ......................... 202110464966.0

(51) Int. Cl.
*C07D 223/32* (2006.01)
*C07F 15/00* (2006.01)
(Continued)

(52) U.S. Cl.
CPC ........ *C07D 223/32* (2013.01); *C07F 15/0086* (2013.01); *H10K 85/342* (2023.02);
(Continued)

(58) Field of Classification Search
CPC ............... C07D 223/32; C07F 15/0086; C07F 15/0033; C07F 5/00; C07F 5/003;
(Continued)

(56) References Cited

U.S. PATENT DOCUMENTS 5,703,436 A 12/1997 Forrest et al.
5,707,745 A 1/1998 Forrest et al.
(Continued)

FOREIGN PATENT DOCUMENTS

CN 110016059 A 7/2019
CN 111100129 A 5/2020
(Continued)

OTHER PUBLICATIONS

English translation of KR 20150077220 A obtained by Google Patents (Year: 2015).*
(Continued)

*Primary Examiner* — Jennifer A Boyd
*Assistant Examiner* — Braelyn R Watson
(74) *Attorney, Agent, or Firm* — Workman Nydegger

(57) ABSTRACT

Provided is an electroluminescent device. The electroluminescent device includes an anode, a cathode and an organic layer disposed between the anode and the cathode, where the organic layer includes at least a first compound having a structure of H-L-E and a second compound having a general formula of $M(L_a)_m(L_b)_n(L_c)_q$. The novel material combination consisting of the first compound and the second compound can enable the electroluminescent device to obtain a lower voltage, higher efficiency and an ultra-long lifetime and can provide better device performance. Further provided are a display assembly and a compound combination.

30 Claims, 2 Drawing Sheets

(51) Int. Cl.

| | |
|---|---|
| ***H10K 50/11*** | (2023.01) |
| ***H10K 85/30*** | (2023.01) |
| ***H10K 85/60*** | (2023.01) |

(52) U.S. Cl.
CPC ....... *H10K 85/654* (2023.02); *H10K 85/6572* (2023.02); *H10K 50/11* (2023.02)

(58) Field of Classification Search
CPC ...... C07F 5/06-069; C07F 7/00; C07F 7/003; C07F 7/22-28; C07F 9/00; C07F 9/005; H10K 85/342; H10K 85/654; H10K 50/11; H10K 2101/10; H10K 50/12; H10K 85/615; H10K 85/631; H10K 85/30-351; H10K 85/371; H10K 85/657-6572; H01L 51/0077; H01L 51/0078; H01L 51/0079; H01L 51/008; H01L 51/0081; H01L 51/0082; H01L 51/0083; H01L 51/0084; H01L 51/0085; H01L 51/0086; H01L 51/0087; H01L 51/0088; H01L 51/0089; H01L 51/0091; H01L 51/0092; H01L 51/0071; H01L 51/0072; C09K 11/06; C09K 2211/182-188
See application file for complete search history.

(56) References Cited

U.S. PATENT DOCUMENTS

| | | | | |
|---|---|---|---|---|
| 5,844,363 | A | 12/1998 | Gu et al. | |
| 6,097,147 | A | 8/2000 | Baldo et al. | |
| 6,303,238 | B1 | 10/2001 | Thompson et al. | |
| 7,279,704 | B2 | 10/2007 | Walters et al. | |
| 7,968,416 | B2 | 6/2011 | Bottner et al. | |
| 2003/0230980 | A1 | 12/2003 | Forrest et al. | |
| 2004/0174116 | A1 | 9/2004 | Lu et al. | |
| 2008/0194853 | A1* | 8/2008 | Kim | C09K 11/06 556/13 |
| 2008/0261076 | A1* | 10/2008 | Kwong | H10K 85/381 546/4 |
| 2015/0001472 | A1* | 1/2015 | Boudreault | C07F 15/0033 546/4 |
| 2015/0236277 | A1* | 8/2015 | Boudreault | H10K 85/342 257/40 |
| 2015/0349273 | A1 | 12/2015 | Hung et al. | |
| 2016/0359122 | A1 | 12/2016 | Boudreault et al. | |
| 2018/0337340 | A1* | 11/2018 | Moon | C07D 487/16 |
| 2019/0214582 | A1* | 7/2019 | Thompson | C07F 7/0812 |
| 2021/0328153 | A1 | 10/2021 | Zhang et al. | |
| 2022/0077404 | A1 | 3/2022 | Zhang et al. | |
| 2022/0177502 | A1 | 6/2022 | Wang et al. | |
| 2022/0231232 | A1 | 7/2022 | Wang et al. | |
| 2022/0274998 | A1 | 9/2022 | Wang et al. | |
| 2022/0289681 | A1 | 9/2022 | Wang et al. | |

FOREIGN PATENT DOCUMENTS

| | | | | |
|---|---|---|---|---|
| CN | 112876489 | | | 6/2021 |
| CN | 113527316 | | | 10/2021 |
| CN | 113527317 | | | 10/2021 |
| CN | 113968873 | | | 1/2022 |
| CN | 113968875 | | | 1/2022 |
| CN | 114075208 | | | 2/2022 |
| CN | 114835718 | | | 8/2022 |
| KR | 20150077220 | | | 7/2015 |
| KR | 20150077220 | A | * | 7/2015 |
| KR | 20200034636 | A | | 3/2020 |
| WO | 2020091446 | A1 | | 5/2020 |

OTHER PUBLICATIONS

Joyama et al., "Highly efficient organic light-emitting diodes from delayed fluorescence," Nature, vol. 492, (Dec. 13, 2012), pp. 234-238.

Tang et al., "Organic electroluminescent diodes," Applied Physics Letters, (Sep. 1987), pp. 913-915.

Chinese Notification to Grant for Chinese Application No. 202110464966.0, dated Jun. 28, 2023, 3 pages with translation.

Chinese Search Report for Chinese Application No. 2021104649660, dated Jun. 15, 2023 4 pages with translation.

Korean Notice of Reasons for Rejection for Korean Application No. 10-2021-0072716, dated May 11, 2023, 19 pages with English translation.

Korean Notice of Final Rejection for Korean Application No. 10-2021-0072716, dated Jan. 22, 2024, 7 pages with English translation.

* cited by examiner

ELECTROLUMINESCENT DEVICE

TECHNICAL FIELD

The present disclosure relates to electronic devices, for example, electroluminescent devices. In particular, the present disclosure relates to an electroluminescent device containing a novel material combination of a first compound having a structure of H-L-E and a second compound having a general formula of $M(L_a)_m(L_b)_n(L_c)_q$ in an organic layer.

BACKGROUND

Organic electronic devices include, but are not limited to, the following types: organic light-emitting diodes (OLEDs), organic field-effect transistors (O-FETs), organic light-emitting transistors (OLETs), organic photovoltaic devices (OPVs), dye-sensitized solar cells (DSSCs), organic optical detectors, organic photoreceptors, organic field-quench devices (OFQDs), light-emitting electrochemical cells (LECs), organic laser diodes and organic plasmon emitting devices.

In 1987, Tang and Van Slyke of Eastman Kodak reported a bilayer organic electroluminescent device, which comprises an arylamine hole transporting layer and a tris-8-hydroxyquinolato-aluminum layer as the electron and emitting layer (Applied Physics Letters, 1987, 51 (12): 913-915). Once a bias is applied to the device, green light was emitted from the device. This device laid the foundation for the development of modern organic light-emitting diodes (OLEDs). State-of-the-art OLEDs may comprise multiple layers such as charge injection and transporting layers, charge and exciton blocking layers, and one or multiple emissive layers between the cathode and anode. Since the OLED is a self-emitting solid state device, it offers tremendous potential for display and lighting applications. In addition, the inherent properties of organic materials, such as their flexibility, may make them well suited for particular applications such as fabrication on flexible substrates.

The OLED can be categorized as three different types according to its emitting mechanism. The OLED invented by Tang and van Slyke is a fluorescent OLED. It only utilizes singlet emission. The triplets generated in the device are wasted through nonradiative decay channels. Therefore, the internal quantum efficiency (IQE) of the fluorescent OLED is only 25%. This limitation hindered the commercialization of OLED. In 1997, Forrest and Thompson reported phosphorescent OLED, which uses triplet emission from heavy metal containing complexes as the emitter. As a result, both singlet and triplets can be harvested, achieving 100% IQE. The discovery and development of phosphorescent OLED contributed directly to the commercialization of active-matrix OLED (AMOLED) due to its high efficiency. Recently, Adachi achieved high efficiency through thermally activated delayed fluorescence (TADF) of organic compounds. These emitters have small singlet-triplet gap that makes the transition from triplet back to singlet possible. In the TADF device, the triplet excitons can go through reverse intersystem crossing to generate singlet excitons, resulting in high IQE.

OLEDs can also be classified as small molecule and polymer OLEDs according to the forms of the materials used. A small molecule refers to any organic or organometallic material that is not a polymer. The molecular weight of the small molecule can be large as long as it has well defined structure. Dendrimers with well-defined structures are considered as small molecules. Polymer OLEDs include conjugated polymers and non-conjugated polymers with pendant emitting groups. Small molecule OLED can become the polymer OLED if post polymerization occurred during the fabrication process.

There are various methods for OLED fabrication. Small molecule OLEDs are generally fabricated by vacuum thermal evaporation. Polymer OLEDs are fabricated by solution process such as spin-coating, inkjet printing, and slit printing. If the material can be dissolved or dispersed in a solvent, the small molecule OLED can also be produced by solution process.

The emitting color of the OLED can be achieved by emitter structural design. An OLED may comprise one emitting layer or a plurality of emitting layers to achieve desired spectrum. In the case of green, yellow, and red OLEDs, phosphorescent emitters have successfully reached commercialization. Blue phosphorescent device still suffers from non-saturated blue color, short device lifetime, and high operating voltage. Commercial full-color OLED displays normally adopt a hybrid strategy, using fluorescent blue and phosphorescent yellow, or red and green. At present, efficiency roll-off of phosphorescent OLEDs at high brightness remains a problem. In addition, it is desirable to have more saturated emitting color, higher efficiency, and longer device lifetime.

To develop phosphorescent OLEDs, appropriate host materials are to be selected for use in conjunction with phosphorescent light-emitting materials, which is an important and extensive research direction.

KR1020150077220A has disclosed a compound with a general formula of

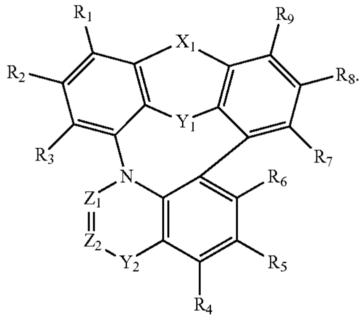

Specific examples include

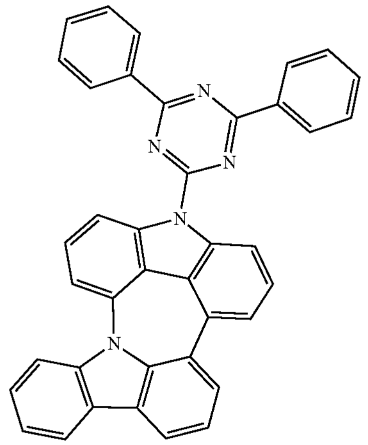

and

-continued

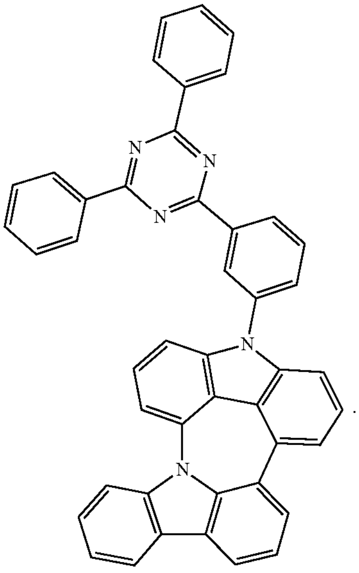

Although this application claims the synthesis of these two compounds, the characterization data of the key intermediate

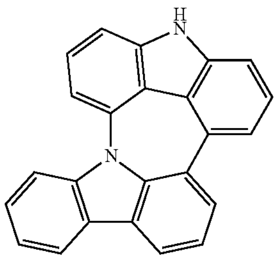 [SMILES: c1cc2[nH]c3cccc4c3c2c(c1)c1cccc2c3ccccc3n4c12]

provided by this application does not match the structure of this compound. Therefore, whether these two compounds have been obtained remains uncertain. Additionally, this application has only mentioned the use in conjunction with the following light-emitting materials:

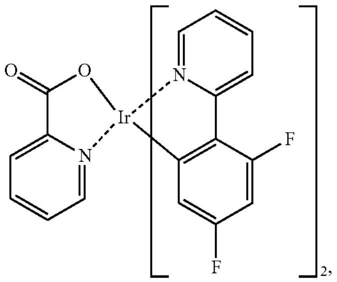

-continued

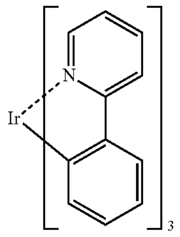

and

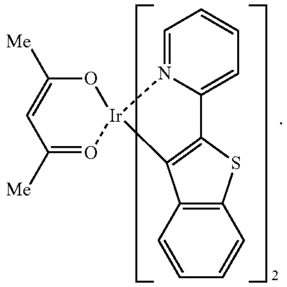

This application pays no attention to the coordination of host materials and light-emitting materials and has not disclosed or taught the use of the disclosed host materials in conjunction with light-emitting materials of other structures.

US20180337340A1 has disclosed an organic electroluminescent compound and an organic electroluminescent device containing the same. The organic electroluminescent device includes an organic layer containing one or more hosts, where a first host is an organic optical compound having the following structure:

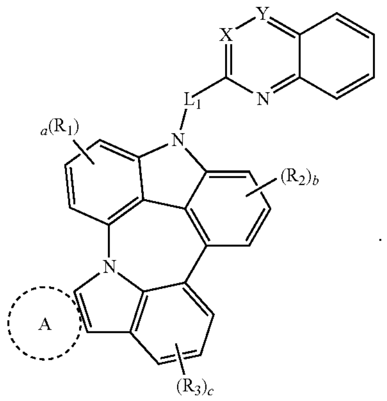

However, the disclosed compounds have to include a structural unit of quinazoline or quinoxaline. Additionally, this application uses a combination of such a host compound and a phosphorescent light-emitting compound,

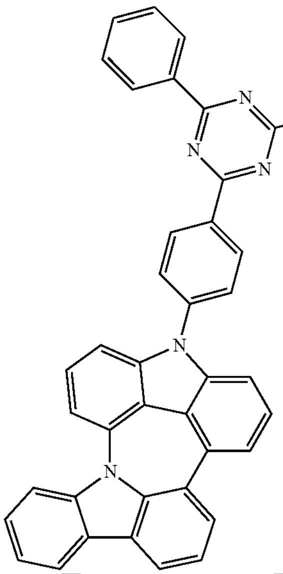

and

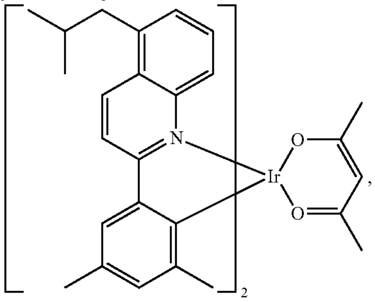

, in a comparative device example. It is believed that the compound formed through carbazole fused to an aza seven-membered ring structural unit and linked to a triazine structural unit is not suitable as phosphorescent host materials. Inventors of this application have not discovered that excellent performance can be obtained by rationally selecting a novel material combination of a host compound having triazine or similar structures and a suitable phosphorescent light-emitting compound. The teaching in the comparative example of this application goes against the present application in essence.

However, the device performance of a combination of a host material and a phosphorescent light-emitting material reported so far can still be improved. To meet the increasing requirements of the industry, it is an efficient research and development means to select a combination of a suitable host material and the phosphorescent light-emitting material and the novel material combination still needs to be further researched and developed.

SUMMARY

The present disclosure aims to provide an electroluminescent device having a novel material combination to solve at least part of the above-mentioned problems. The electroluminescent device adopts a novel material combination consisting of a first compound having a structure of H-L-E and a second compound having a general formula of $M(L_a)_m(L_b)_n(L_c)_q$. The novel material combination may be used in a light-emitting layer of the electroluminescent device. The novel material combination can enable the electroluminescent device to obtain a lower voltage, higher efficiency and an ultra-long lifetime and can provide better device performance.

According to an embodiment of the present disclosure, disclosed is an electroluminescent device including an anode, a cathode and an organic layer disposed between the anode and the cathode, wherein the organic layer at least includes a first compound and a second compound;

the first compound has a structure of H-L-E;

H has a structure represented by Formula 1:

Formula 1

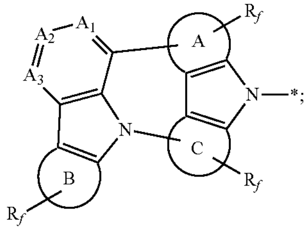

in Formula 1, $A_1$, $A_2$ and $A_3$ are, at each occurrence identically or differently, selected from N or CR, and the ring A, the ring B and the ring C are, at each occurrence identically or differently, selected from a carbocyclic ring having 5 to 18 carbon atoms or a heterocyclic ring having 3 to 18 carbon atoms;

$R_f$ represents, at each occurrence identically or differently, mono-substitution, multiple substitutions or non-substitution;

E has a structure represented by Formula 2:

Formula 2

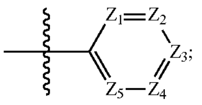

in Formula 2, at least one of $Z_1$ to $Z_5$ is N, and the rest of $Z_1$ to $Z_5$ are each independently selected from $CR_z$;

L is selected from a single bond, substituted or unsubstituted arylene having 6 to 30 carbon atoms, substituted or unsubstituted heteroarylene having 3 to 30 carbon atoms or a combination thereof;

R, $R_f$ and $R_z$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;

adjacent substituents R, $R_f$ can be optionally joined to form a ring;

the second compound is a metal complex having a general formula of $M(L_a)_m(L_b)_n(L_c)_q$;

wherein the M is selected from a metal with a relative atomic mass greater than 40;

$L_a$, $L_b$ and $L_c$ are a first ligand, a second ligand and a third ligand coordinated to the M, respectively; $L_a$, $L_b$ and $L_c$ can be optionally joined to form a multidentate ligand;

$L_a$, $L_b$ and $L_c$ may be the same or different; m is 1, 2 or 3, n is 0, 1 or 2, q is 0 or 1, and m+n+q equals to the oxidation state of the M; when m is greater than or equal to 2, the multiple $L_a$ may be the same or different; when n is equal to 2, the two $L_b$ may be the same or different;

$L_a$ has a structure represented by Formula 3:

Formula 3

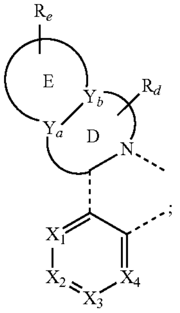

wherein, the ring D is selected from a five-membered heteroaromatic ring or a six-membered heteroaromatic ring;

the ring E is selected from a five-membered unsaturated carbocyclic ring, a benzene ring, a five-membered heteroaromatic ring or a six-membered heteroaromatic ring;

the ring D and the ring E are fused via $Y_a$ and $Y_b$;

$Y_a$ and $Y_b$ are, at each occurrence identically or differently, selected from C or N;

$R_d$ and $R_e$ represent, at each occurrence identically or differently, mono-substitution, multiple substitutions or non-substitution;

$X_1$ to $X_4$ are, at each occurrence identically or differently, selected from $CR_x$ or N;

$R_d$, $R_e$ and $R_x$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;

adjacent substituents $R_d$, $R_e$, $R_x$ can be optionally joined to form a ring;

$L_b$ and $L_c$ are each independently selected from any one of the following structures:

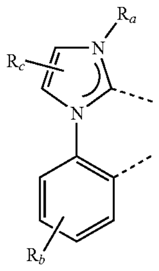, 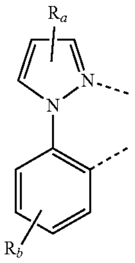, 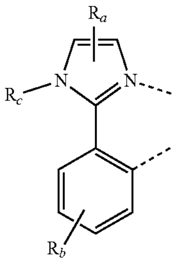, 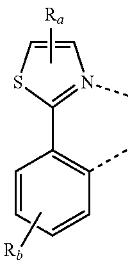, 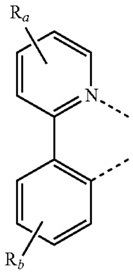, 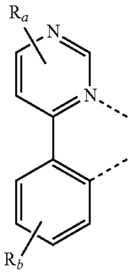, 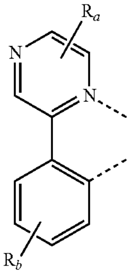, 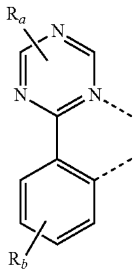, 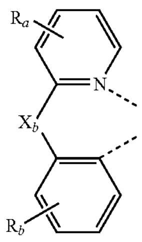, 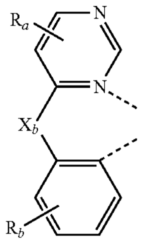, 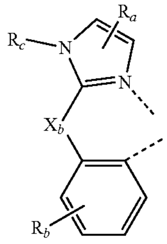, 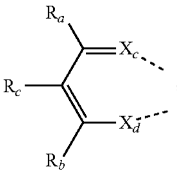;

$R_a$, $R_b$ and $R_c$ represent, at each occurrence identically or differently, mono-substitution, multiple substitutions or non-substitution;

$X_b$ is selected from the group consisting of: O, S, Se, $NR_{N1}$ and $CR_{C1}R_{C2}$;

$X_c$ and $X_d$ are each independently selected from the group consisting of: O, S, Se and $NR_{N2}$;

$R_a$, $R_b$, $R_c$, $R_{N1}$, $R_{N2}$, $R_{C1}$ and $R_{C2}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;

in structures of $L_b$ and $L_c$, adjacent substituents $R_a$, $R_b$, $R_c$, $R_{N1}$, $R_{N2}$, $R_{C1}$ and $R_{C2}$ can be optionally joined to form a ring;

and, the following case is not comprised: the first compound is

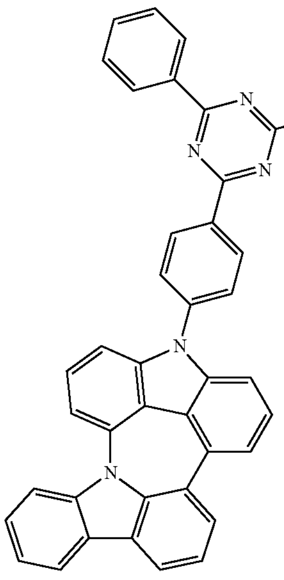

while the second compound is

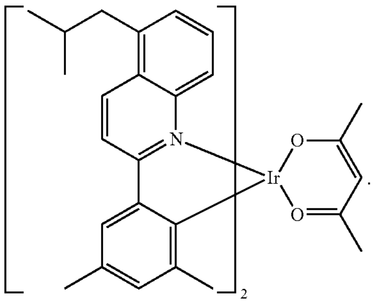

According to another embodiment of the present disclosure, further disclosed is a display assembly comprising the electroluminescent device described above.

According to another embodiment of the present disclosure, further disclosed is a compound combination comprising a first compound and a second compound;

the first compound has a structure of H-L-E;

H has a structure represented by Formula 1:

Formula 1

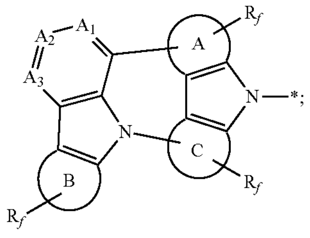

in Formula 1, $A_1$, $A_2$ and $A_3$ are, at each occurrence identically or differently, selected from N or CR, and the ring A, the ring B and the ring C are, at each occurrence identically or differently, selected from a carbocyclic ring having 5 to 18 carbon atoms or a heterocyclic ring having 3 to 18 carbon atoms;

$R_f$ represents, at each occurrence identically or differently, mono-substitution, multiple substitutions or non-substitution;

E has a structure represented by Formula 2:

Formula 2

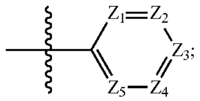

in Formula 2, at least one of $Z_1$ to $Z_5$ is N, and the rest of $Z_1$ to $Z_5$ are each independently selected from $CR_z$;

L is selected from a single bond, substituted or unsubstituted arylene having 6 to 30 carbon atoms, substituted or unsubstituted heteroarylene having 3 to 30 carbon atoms or a combination thereof;

R, $R_f$ and $R_z$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;

adjacent substituents R, $R_f$ can be optionally joined to form a ring;

the second compound is a metal complex having a general formula of $M(L_a)_m(L_b)_n(L_c)_q$;

wherein the M is selected from a metal with a relative atomic mass greater than 40;

$L_a$, $L_b$ and $L_c$ are a first ligand, a second ligand and a third ligand coordinated to the M, respectively; $L_a$, $L_b$ and $L_c$ can be optionally joined to form a multidentate ligand;

$L_a$, $L_b$ and $L_c$ may be the same or different; m is 1, 2 or 3, n is 0, 1 or 2, q is 0 or 1, and m+n+q equals to the oxidation state of the M; when m is greater than or equal to 2, the multiple $L_a$ may be the same or different; when n is equal to 2, the two $L_b$ may be the same or different;

$L_a$ has a structure represented by Formula 3:

Formula 3

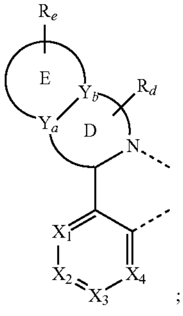

;

wherein, the ring D is selected from a five-membered heteroaromatic ring or a six-membered heteroaromatic ring;

the ring E is selected from a five-membered unsaturated carbocyclic ring, a benzene ring, a five-membered heteroaromatic ring or a six-membered heteroaromatic ring;

the ring D and the ring E are fused via $Y_a$ and $Y_b$;

$Y_a$ and $Y_b$ are, at each occurrence identically or differently, selected from C or N;

$R_d$ and $R_e$ represent, at each occurrence identically or differently, mono-substitution, multiple substitutions or non-substitution;

$X_1$ to $X_4$ are, at each occurrence identically or differently, selected from $CR_x$ or N;

$R_d$, $R_e$ and $R_x$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;

adjacent substituents $R_d$, $R_e$, $R_x$ can be optionally joined to form a ring;

$L_b$ and $L_c$ are each independently selected from any one of the following structures:

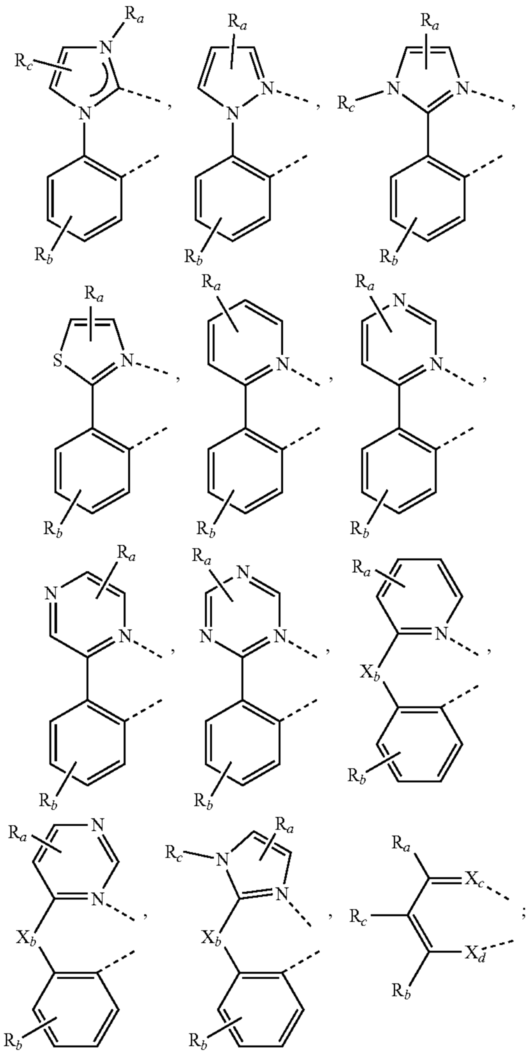

$R_a$, $R_b$ and $R_c$ represent, at each occurrence identically or differently, mono-substitution, multiple substitutions or non-substitution;

$X_b$ is selected from the group consisting of: O, S, Se, $NR_{N1}$ and $CR_{C1}R_{C2}$;

$X_c$ and $X_d$ are each independently selected from the group consisting of: O, S, Se and $NR_{N2}$;

$R_a$, $R_b$, $R_c$, $R_{N1}$, $R_{N2}$, $R_{C1}$ and $R_{C2}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;

in structures of $L_b$ and $L_c$, adjacent substituents $R_a$, $R_b$, $R_c$, $R_{N1}$, $R_{N2}$, $R_{C1}$ and $R_{C2}$ can be optionally joined to form a ring;

and, the following case is not comprised: the first compound is

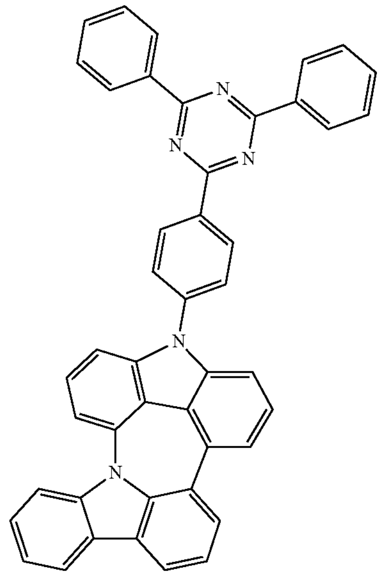 [SMILES: c1ccc(-c2nc(-c3ccccc3)nc(-c3ccc(-n4c5cccc6c7cccc8c9ccccc9n(c9cccc4c9c65)c78)cc3)n2)cc1]

while the second compound is

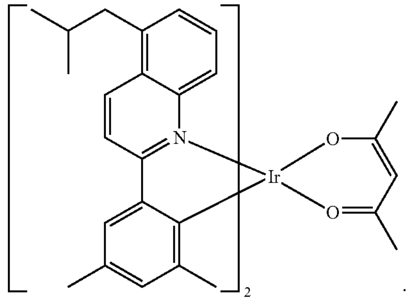

The present disclosure discloses a novel electroluminescent device. The electroluminescent device adopts the novel material combination consisting of the first compound having the structure of H-L-E and the second compound having the general formula of $M(L_a)_m(L_b)_n(L_c)_q$. The novel material combination may be used in the light-emitting layer of the electroluminescent device. The novel material combination can enable the novel electroluminescent device to obtain the lower voltage, the higher efficiency and the ultra-long lifetime and can provide the better device performance.

DETAILED DESCRIPTION

Figure 1:
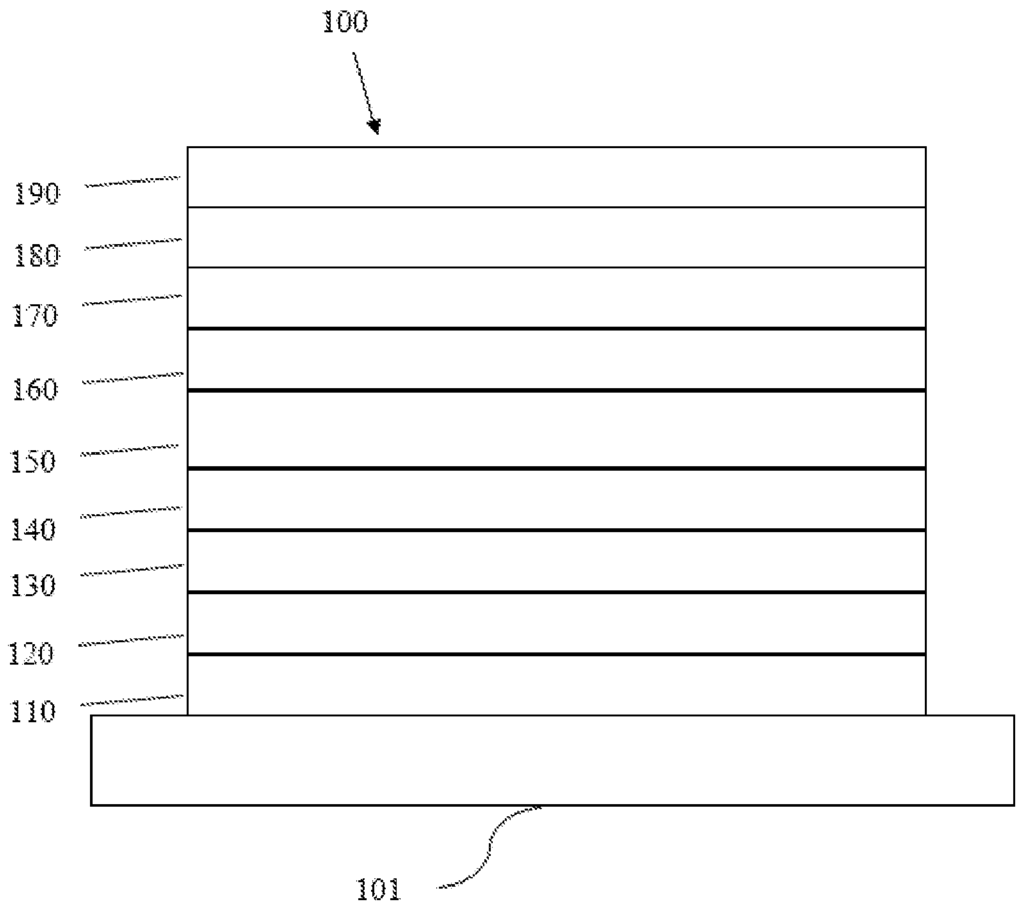
FIG. 1 is a schematic diagram of an organic light-emitting apparatus that may include an electroluminescent device disclosed by the present disclosure.

OLEDs can be fabricated on various types of substrates such as glass, plastic, and metal foil. FIG. 1 schematically shows an organic light emitting device 100 without limitation. The figures are not necessarily drawn to scale. Some of the layers in the figures can also be omitted as needed. Device 100 may include a substrate 101, an anode 110, a hole injection layer 120, a hole transport layer 130, an electron blocking layer 140, an emissive layer 150, a hole blocking layer 160, an electron transport layer 170, an electron injection layer 180 and a cathode 190. Device 100 may be fabricated by depositing the layers described in order. The properties and functions of these various layers, as well as example materials, are described in more detail in U.S. Pat. No. 7,279,704 at cols. 6-10, the contents of which are incorporated by reference herein in its entirety.

More examples for each of these layers are available. For example, a flexible and transparent substrate-anode combination is disclosed in U.S. Pat. No. 5,844,363, which is incorporated by reference herein in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference herein in its entirety. Examples of host materials are disclosed in U.S. Pat. No. 6,303,238 to Thompson et al., which is incorporated by reference herein in its entirety. An example of an n-doped electron transport layer is BPhen doped with Li at a molar ratio of 1:1, as disclosed in U.S. Patent Application Publication No. 2003/0230980, which is incorporated by reference herein in its entirety. U.S. Pat. Nos. 5,703,436 and 5,707,745, which are incorporated by reference herein in their entireties, disclose examples of cathodes including composite cathodes having a thin layer of metal such as Mg:Ag with an overlying transparent, electrically-conductive, sputter-deposited ITO layer. The theory and use of blocking layers are described in more detail in U.S. Pat. No. 6,097,147 and U.S. Patent Application Publication No. 2003/0230980, which are incorporated by reference herein in their entireties. Examples of injection layers are provided in U.S. Patent Application Publication No. 2004/0174116, which is incorporated by reference herein in its entirety. A description of protective layers may be found in U.S. Patent Application Publication No. 2004/0174116, which is incorporated by reference herein in its entirety.

The layered structure described above is provided by way of non-limiting examples. Functional OLEDs may be achieved by combining the various layers described in different ways, or layers may be omitted entirely. It may also include other layers not specifically described. Within each layer, a single material or a mixture of multiple materials can be used to achieve optimum performance. Any functional layer may include several sublayers. For example, the emissive layer may have two layers of different emitting materials to achieve desired emission spectrum.

In one embodiment, an OLED may be described as having an "organic layer" disposed between a cathode and an anode. This organic layer may comprise a single layer or multiple layers.

Figure 2:
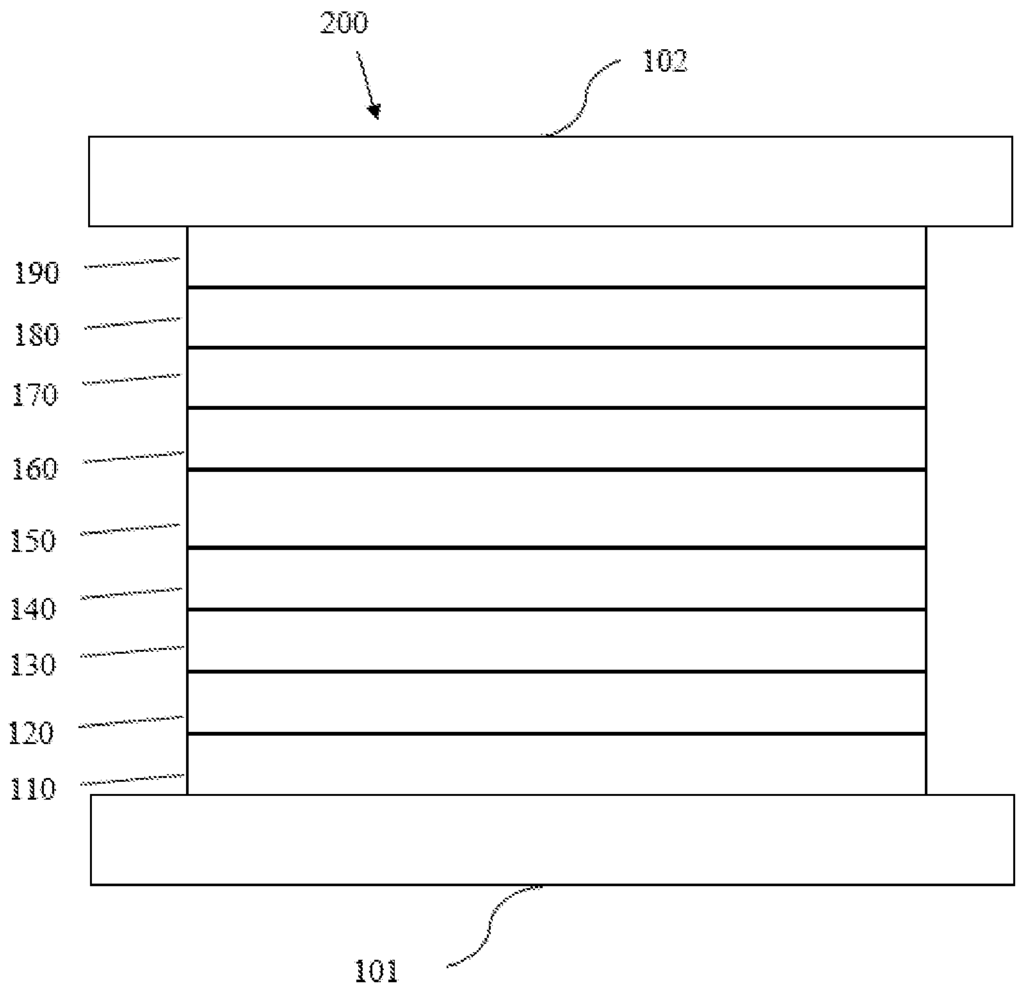
FIG. 2 is a schematic diagram of another organic light-emitting apparatus that may include an electroluminescent device disclosed by the present disclosure.

An OLED can be encapsulated by a barrier layer. FIG. 2 schematically shows an organic light emitting device 200 without limitation. FIG. 2 differs from FIG. 1 in that the organic light emitting device include a barrier layer 102, which is above the cathode 190, to protect it from harmful species from the environment such as moisture and oxygen. Any material that can provide the barrier function can be used as the barrier layer such as glass or organic-inorganic hybrid layers. The barrier layer should be placed directly or indirectly outside of the OLED device. Multilayer thin film encapsulation was described in U.S. Pat. No. 7,968,146, which is incorporated by reference herein in its entirety.

Devices fabricated in accordance with embodiments of the present disclosure can be incorporated into a wide variety of consumer products that have one or more of the electronic component modules (or units) incorporated therein. Some examples of such consumer products include flat panel displays, monitors, medical monitors, televisions, billboards, lights for interior or exterior illumination and/or signaling, heads-up displays, fully or partially transparent displays, flexible displays, smart phones, tablets, phablets, wearable devices, smart watches, laptop computers, digital cameras, camcorders, viewfinders, micro-displays, 3-D displays, vehicles displays, and vehicle tail lights.

The materials and structures described herein may be used in other organic electronic devices listed above.

As used herein, "top" means furthest away from the substrate, while "bottom" means closest to the substrate. Where a first layer is described as "disposed over" a second layer, the first layer is disposed further away from the substrate. There may be other layers between the first and second layers, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the transition between the triplet states and the singlet excited states. Compounds that are capable of generating E-type delayed fluorescence are required to have very small singlet-triplet gaps to convert between energy states. Thermal energy can activate the transition from the triplet state back to the singlet state. This type of delayed fluorescence is also known as thermally activated delayed fluorescence (TADF). A distinctive feature of TADF is that the delayed component increases as temperature rises. If the reverse intersystem crossing rate is fast enough to minimize the non-radiative decay from the triplet state, the fraction of back populated singlet excited states can potentially reach 75%. The total singlet fraction can be 100%, far exceeding 25% of the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap (AEs-T). Organic, non-metal containing, donor-acceptor luminescent materials may be able to achieve this. The emission in these materials is generally characterized as a donor-acceptor charge-transfer (CT) type emission. The spatial separation of the HOMO and LUMO in these donor-acceptor type compounds generally results in small $\Delta E_{S-T}$. These states may involve CT states. Generally, donor-acceptor luminescent materials are constructed by connecting an electron donor moiety such as amino- or carbazole-derivatives and an electron acceptor moiety such as N-containing six-membered aromatic rings.

Definition of Terms of Substituents

Halogen or halide—as used herein includes fluorine, chlorine, bromine, and iodine.

Alkyl—as used herein includes both straight and branched chain alkyl groups. Alkyl may be alkyl having 1 to 20 carbon atoms, preferably alkyl having 1 to 12 carbon atoms, and more preferably alkyl having 1 to 6 carbon atoms. Examples of alkyl groups include a methyl group, an ethyl group, a propyl group, an isopropyl group, a n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a 2-methylpentyl group, a 1-pentylhexyl group, a 1-butylpentyl group, a 1-heptyloctyl group, and a 3-methylpentyl group. Additionally, the alkyl may be optionally substituted. Of the above, preferred are a methyl group, an ethyl group, a propyl group, an isopropyl group, a n-butyl group, an s-butyl group, an isobutyl group, a t-butyl group, an n-pentyl group, a neopentyl group, and an n-hexyl group. Additionally, the alkyl group may be optionally substituted.

Cycloalkyl—as used herein includes cyclic alkyl groups. The cycloalkyl groups may be those having 3 to 20 ring carbon atoms, preferably those having 4 to 10 carbon atoms. Examples of cycloalkyl include cyclobutyl, cyclopentyl, cyclohexyl, 4-methylcyclohexyl, 4,4-dimethylcylcohexyl, 1-adamantyl, 2-adamantyl, 1-norbornyl, 2-norbornyl, and the like. Of the above, preferred are cyclopentyl, cyclohexyl, 4-methylcyclohexyl, and 4,4-dimethylcylcohexyl. Additionally, the cycloalkyl group may be optionally substituted.

Heteroalkyl—as used herein, includes a group formed by replacing one or more carbons in an alkyl chain with a hetero-atom(s) selected from the group consisting of a nitrogen atom, an oxygen atom, a sulfur atom, a selenium atom, a phosphorus atom, a silicon atom, a germanium atom, and a boron atom. Heteroalkyl may be those having 1 to 20 carbon atoms, preferably those having 1 to 10 carbon atoms, and more preferably those having 1 to 6 carbon atoms. Examples of heteroalkyl include methoxymethyl, ethoxymethyl, ethoxyethyl, methylthiomethyl, ethylthiomethyl, ethylthioethyl, methoxymethoxymethyl, ethoxymethoxymethyl, ethoxyethoxyethyl, hydroxymethyl, hydroxyethyl, hydroxypropyl, mercaptomethyl, mercaptoethyl, mercaptopropyl, aminomethyl, aminoethyl, aminopropyl, dimethylaminomethyl, trimethylsilyl, dimethylethylsilyl, dimethylisopropylsilyl, t-butyldimethylsilyl, triethylsilyl, triisopropylsilyl, trimethylsilylmethyl, trimethylsilylethyl, and trimethylsilylisopropyl. Additionally, the heteroalkyl group may be optionally substituted.

Alkenyl—as used herein includes straight chain, branched chain, and cyclic alkene groups. Alkenyl may be those having 2 to 20 carbon atoms, preferably those having 2 to 10 carbon atoms. Examples of alkenyl include vinyl, propenyl, 1-butenyl, 2-butenyl, 3-butenyl, 1,3-butandienyl, 1-methylvinyl, styryl, 2,2-diphenylvinyl, 1,2-diphenylvinyl, 1-methylallyl, 1,1-dimethylallyl, 2-methylallyl, 1-phenylallyl, 2-phenylallyl, 3-phenylallyl, 3,3-diphenylallyl, 1,2-dimethylallyl, 1-phenyl-1-butenyl, 3-phenyl-1-butenyl, cyclopentenyl, cyclopentadienyl, cyclohexenyl, cycloheptenyl, cycloheptatrienyl, cyclooctenyl, cyclooctatetraenyl, and norbornenyl. Additionally, the alkenyl group may be optionally substituted.

Alkynyl—as used herein includes straight chain alkynyl groups. Alkynyl may be those having 2 to 20 carbon atoms, preferably those having 2 to 10 carbon atoms. Examples of alkynyl groups include ethynyl, propynyl, propargyl, 1-butynyl, 2-butynyl, 3-butynyl, 1-pentynyl, 2-pentynyl, 3,3-dimethyl-1-butynyl, 3-ethyl-3-methyl-1-pentynyl, 3,3-diisopropyl-1-pentynyl, phenylethynyl, phenylpropynyl, etc. Of the above, preferred are ethynyl, propynyl, propargyl, 1-butynyl, 2-butynyl, 3-butynyl, 1-pentynyl, and phenylethynyl. Additionally, the alkynyl group may be optionally substituted.

Aryl or an aromatic group—as used herein includes non-condensed and condensed systems. Aryl may be those having 6 to 30 carbon atoms, preferably those having 6 to 20 carbon atoms, and more preferably those having 6 to 12 carbon atoms. Examples of aryl groups include phenyl, biphenyl, terphenyl, triphenylene, tetraphenylene, naphthalene, anthracene, phenalene, phenanthrene, fluorene, pyrene, chrysene, perylene, and azulene, preferably phenyl, biphenyl, terphenyl, triphenylene, fluorene, and naphthalene. Additionally, the aryl may be optionally substituted. Examples of non-condensed aryl groups include phenyl, biphenyl-2-yl, biphenyl-3-yl, biphenyl-4-yl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-(2-phenylpropyl)phenyl, 4'-methylbiphenylyl, 4"-t-butyl-p-terphenyl-4-yl, o-cumenyl, m-cumenyl, p-cumenyl, 2,3-xylyl, 3,4-xylyl, 2,5-xylyl, mesityl, and m-quarterphenyl. Additionally, the aryl group may be optionally substituted.

Heterocyclic groups or heterocycle—as used herein include non-aromatic cyclic groups. Non-aromatic heterocyclic groups include saturated heterocyclic groups having 3 to 20 ring atoms and unsaturated non-aromatic heterocyclic groups having 3 to 20 ring atoms, where at least one ring atom is selected from the group consisting of a nitrogen atom, an oxygen atom, a sulfur atom, a selenium atom, a silicon atom, a phosphorus atom, a germanium atom, and a boron atom. Preferred non-aromatic heterocyclic groups are those having 3 to 7 ring atoms, each of which includes at least one hetero-atom such as nitrogen, oxygen, silicon, or sulfur. Examples of non-aromatic heterocyclic groups include oxiranyl, oxetanyl, tetrahydrofuranyl, tetrahydropyranyl, dioxolanyl, dioxanyl, aziridinyl, dihydropyrrolyl, tetrahydropyrrolyl, piperidinyl, oxazolidinyl, morpholinyl, piperazinyl, oxepinyl, thiepinyl, azepinyl, and tetrahydrosilolyl. Additionally, the heterocyclic group may be optionally substituted.

Heteroaryl—as used herein, includes non-condensed and condensed hetero-aromatic groups having 1 to 5 hetero-atoms, wherein at least one hetero-atom is selected from the group consisting of a nitrogen atom, an oxygen atom, a sulfur atom, a selenium atom, a silicon atom, a phosphorus atom, a germanium atom, and a boron atom. A hetero-aromatic group is also referred to as heteroaryl. Heteroaryl may be those having 3 to 30 carbon atoms, preferably those having 3 to 20 carbon atoms, and more preferably those having 3 to 12 carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridoindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indenoazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Alkoxy—as used herein, is represented by —O-alkyl, —O-cycloalkyl, —O-heteroalkyl, or —O-heterocyclic group. Examples and preferred examples of alkyl, cycloalkyl, heteroalkyl, and heterocyclic groups are the same as those described above. Alkoxy groups may be those having 1 to 20 carbon atoms, preferably those having 1 to 6 carbon atoms. Examples of alkoxy groups include methoxy, ethoxy, propoxy, butoxy, pentyloxy, hexyloxy, cyclopropyloxy, cyclobutyloxy, cyclopentyloxy, cyclohexyloxy, tetrahydrofuranyloxy, tetrahydropyranyloxy, methoxypropyloxy, ethoxyethyloxy, methoxymethyloxy, and ethoxymethyloxy. Additionally, the alkoxy group may be optionally substituted.

Aryloxy—as used herein, is represented by —O-aryl or —O-heteroaryl. Examples and preferred examples of aryl and heteroaryl are the same as those described above. Aryloxy groups may be those having 6 to 30 carbon atoms, preferably those having 6 to 20 carbon atoms. Examples of aryloxy groups include phenoxy and biphenyloxy. Additionally, the aryloxy group may be optionally substituted.

Arylalkyl—as used herein, contemplates alkyl substituted with an aryl group. Arylalkyl may be those having 7 to 30 carbon atoms, preferably those having 7 to 20 carbon atoms, and more preferably those having 7 to 13 carbon atoms. Examples of arylalkyl groups include benzyl, 1-phenylethyl, 2-phenylethyl, 1-phenylisopropyl, 2-phenylisopropyl, phenyl-t-butyl, alpha-naphthylmethyl, 1-alpha-naphthylethyl, 2-alpha-naphthylethyl, 1-alpha-naphthylisopropyl, 2-alpha-naphthylisopropyl, beta-naphthylmethyl, 1-beta-naphthylethyl, 2-beta-naphthylethyl, 1-beta-naphthylisopropyl, 2-beta-naphthylisopropyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl, and 1-chloro-2-phenylisopropyl. Of the above, preferred are benzyl, p-cyanobenzyl, m-cyanobenzyl, o-cyanobenzyl, 1-phenylethyl, 2-phenyl ethyl, 1-phenylisopropyl, and 2-phenylisopropyl. Additionally, the arylalkyl group may be optionally substituted.

Alkylsilyl—as used herein, contemplates a silyl group substituted with an alkyl group. Alkylsilyl groups may be those having 3 to 20 carbon atoms, preferably those having 3 to 10 carbon atoms. Examples of alkylsilyl groups include trimethylsilyl, triethylsilyl, methyldiethylsilyl, ethyldimethylsilyl, tripropylsilyl, tributylsilyl, triisopropylsilyl, methyldiisopropylsilyl, dimethylisopropylsilyl, tri-t-butylsilyl, triisobutylsilyl, dimethyl t-butylsilyl, and methyl di-t-butylsilyl. Additionally, the alkylsilyl group may be optionally substituted.

Arylsilyl—as used herein, contemplates a silyl group substituted with at least one aryl group. Arylsilyl groups may be those having 6 to 30 carbon atoms, preferably those having 8 to 20 carbon atoms. Examples of arylsilyl groups include triphenylsilyl, phenyldibiphenylylsilyl, diphenylbiphenylsilyl, phenyldiethylsilyl, diphenylethylsilyl, phenyldimethylsilyl, diphenylmethylsilyl, phenyldiisopropylsilyl, diphenylisopropylsilyl, diphenylbutylsilyl, diphenylisobutylsilyl, diphenyl t-butylsilyl, tri-t-butylsilyl, dimethyl t-butylsilyl, methyl di-t-butylsilyl. Additionally, the arylsilyl group may be optionally substituted.

The term "aza" in azadibenzofuran, aza-dibenzothiophene, etc. means that one or more of the C—H groups in the respective aromatic fragment are replaced by a nitrogen atom. For example, azatriphenylene encompasses dibenzo[f,h]quinoxaline, dibenzo[f,h]quinoline and other analogues with two or more nitrogens in the ring system. One of ordinary skill in the art can readily envision other nitrogen analogs of the aza-derivatives described above, and all such analogs are intended to be encompassed by the terms as set forth herein.

In the present disclosure, unless otherwise defined, when any term of the group consisting of substituted alkyl, substituted cycloalkyl, substituted heteroalkyl, a substituted heterocyclic group, substituted arylalkyl, substituted alkoxy, substituted aryloxy, substituted alkenyl, substituted alkynyl, substituted aryl, substituted heteroaryl, substituted alkylsilyl, substituted arylsilyl, substituted amino, substituted acyl, substituted carbonyl, a substituted carboxylic acid group, a substituted ester group, substituted sulfinyl, substituted sulfonyl and substituted phosphino is used, it means that any group of alkyl, cycloalkyl, heteroalkyl, arylalkyl, alkoxy, aryloxy, alkenyl, alkynyl, aryl, heteroaryl, alkylsilyl, arylsilyl, amino, acyl, carbonyl, carboxylic acid group, ester group, sulfinyl, sulfonyl and phosphino may be substituted with one or more groups selected from the group consisting of deuterium, halogen, an unsubstituted alkyl group having 1 to 20 carbon atoms, an unsubstituted cycloalkyl group having 3 to 20 ring carbon atoms, an unsubstituted heteroalkyl group having 1 to 20 carbon atoms, an unsubstituted heterocyclic group having 3 to 20 ring atoms, an unsubstituted arylalkyl group having 7 to 30 carbon atoms, an unsubstituted alkoxy group having 1 to 20 carbon atoms, an unsubstituted aryloxy group having 6 to 30 carbon atoms, an unsubstituted alkenyl group having 2 to 20 carbon atoms, an unsubstituted alkynyl group having 2 to 20 carbon atoms, an unsubstituted aryl group having 6 to 30 carbon atoms, an unsubstituted heteroaryl group having 3 to 30 carbon atoms, an unsubstituted alkylsilyl group having 3 to 20 carbon atoms, an unsubstituted arylsilyl group having 6 to 20 carbon atoms, an unsubstituted amino group having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In the compounds mentioned in the present disclosure, the hydrogen atoms can be partially or fully replaced by deuterium. Other atoms such as carbon and nitrogen can also be replaced by their other stable isotopes. The replacement by other stable isotopes in the compounds may be preferred due to its enhancements of device efficiency and stability.

In the compounds mentioned in the present disclosure, multiple substitutions refer to a range that includes a double substitution, up to the maximum available substitutions. When a substitution in the compounds mentioned in the present disclosure represents multiple substitutions (including di, tri, tetra substitutions etc.), that means the substituent may exist at a plurality of available substitution positions on its linking structure, the substituents present at a plurality of available substitution positions may be the same structure or different structures.

In the compounds mentioned in the present disclosure, adjacent substituents in the compounds cannot connect to form a ring unless otherwise explicitly defined, for example, adjacent substituents can be optionally joined to form a ring. In the compounds mentioned in the present disclosure, adjacent substituents can be optionally joined to form a ring, including both the case where adjacent substituents can be joined to form a ring, and the case where adjacent substituents are not joined to form a ring. When adjacent substituents can be optionally joined to form a ring, the ring formed may be monocyclic or polycyclic, as well as alicyclic, heteroalicyclic, aromatic or heteroaromatic. In such expression, adjacent substituents may refer to substituents bonded to the same atom, substituents bonded to carbon atoms which are directly bonded to each other, or substituents bonded to carbon atoms which are more distant from each other. Preferably, adjacent substituents refer to substituents bonded to the same carbon atom and substituents bonded to carbon atoms which are directly bonded to each other.

The expression that adjacent substituents can be optionally joined to form a ring is also intended to mean that two substituents bonded to the same carbon atom are joined to each other via a chemical bond to form a ring, which can be exemplified by the following formula:

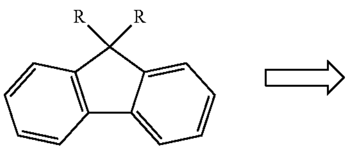

-continued

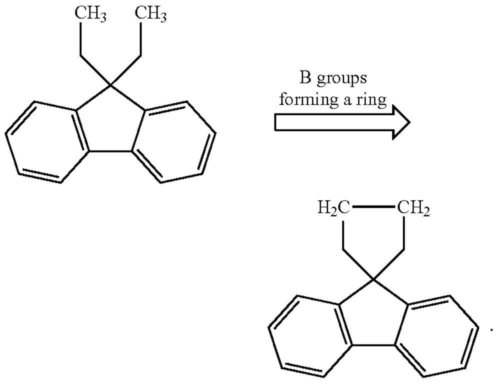

The expression that adjacent substituents can be optionally joined to form a ring is also intended to mean that two substituents bonded to carbon atoms which are directly bonded to each other are joined to each other via a chemical bond to form a ring, which can be exemplified by the following formula:

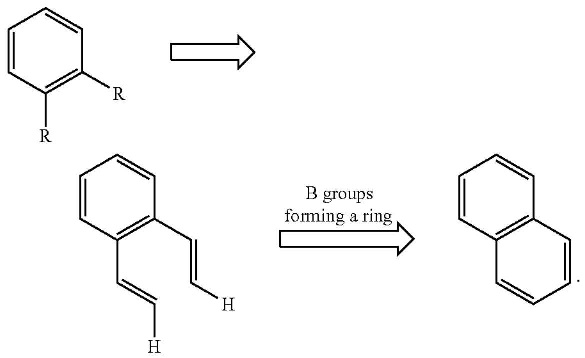

Furthermore, the expression that adjacent substituents can be optionally joined to form a ring is also intended to mean that, in the case where one of the two substituents bonded to carbon atoms which are directly bonded to each other represents hydrogen, the second substituent is bonded at a position at which the hydrogen atom is bonded, thereby forming a ring. This is exemplified by the following formula:

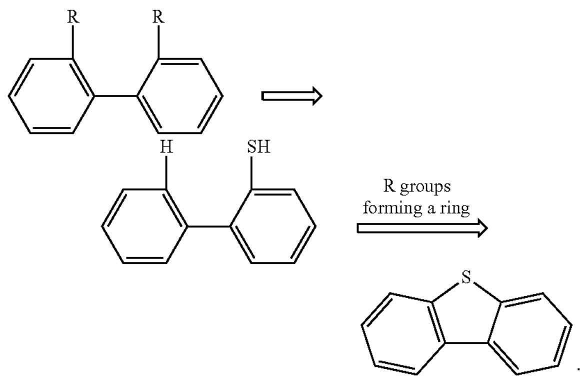

According to an embodiment of the present disclosure, disclosed is an electroluminescent device comprising:

an anode, a cathode, and an organic layer disposed between the anode and the cathode, wherein the organic layer at least comprises a first compound and a second compound;

the first compound has a structure of H-L-E;

H has a structure represented by Formula 1:

Formula 1

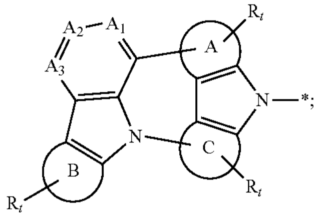

in Formula 1, $A_1$, $A_2$ and $A_3$ are, at each occurrence identically or differently, selected from N or CR, and the ring A, the ring B and the ring C are, at each occurrence identically or differently, selected from a carbocyclic ring having 5 to 18 carbon atoms or a heterocyclic ring having 3 to 18 carbon atoms;

$R_f$ represents, at each occurrence identically or differently, mono-substitution, multiple substitutions or non-substitution;

E has a structure represented by Formula 2:

Formula 2

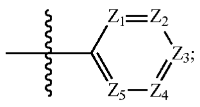

in Formula 2, at least one of $Z_1$ to $Z_5$ is N, and the rest of $Z_1$ to $Z_5$ are each independently selected from $CR_z$;

wherein L is selected from a single bond, substituted or unsubstituted arylene having 6 to 30 carbon atoms, substituted or unsubstituted heteroarylene having 3 to 30 carbon atoms or a combination thereof;

R, $R_f$ and $R_z$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;

adjacent substituents R, $R_f$ can be optionally joined to form a ring;

the second compound is a metal complex having a general formula of $M(L_a)_m(L_b)_n(L_c)_q$;

the M is selected from a metal with a relative atomic mass greater than 40;

$L_a$, $L_b$ and $L_c$ are a first ligand, a second ligand and a third ligand coordinated to the M, respectively; $L_a$, $L_b$ and $L_c$ can be optionally joined to form a multidentate ligand; for example, any two of $L_a$, $L_b$ and $L_c$ may be joined to form a tetradentate ligand; in another example, $L_a$, $L_b$ and $L_c$ may be joined to each other to form a hexadentate ligand; in another example, none of $L_a$, $L_b$ and $L_c$ are joined so that no multidentate ligand is formed;

$L_a$, $L_b$ and $L_c$ may be the same or different; m is 1, 2 or 3, n is 0, 1 or 2, q is 0 or 1, and m+n+q equals to the oxidation state of the M; when m is greater than or equal to 2, the multiple $L_a$ may be the same or different; when n is equal to 2, the two $L_b$ may be the same or different;

$L_a$ has a structure represented by Formula 3:

Formula 3

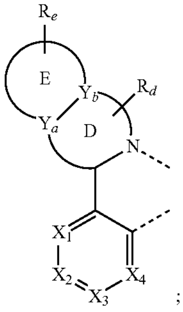

;

wherein, the ring D is selected from a five-membered heteroaromatic ring or a six-membered heteroaromatic ring;

the ring E is selected from a five-membered unsaturated carbocyclic ring, a benzene ring, a five-membered heteroaromatic ring or a six-membered heteroaromatic ring;

the ring D and the ring E are fused via $Y_a$ and $Y_b$;

$Y_a$ and $Y_b$ are, at each occurrence identically or differently, selected from C or N;

$R_d$ and $R_e$ represent, at each occurrence identically or differently, mono-substitution, multiple substitutions or non-substitution;

$X_1$ to $X_4$ are, at each occurrence identically or differently, selected from $CR_x$ or N;

$R_d$, $R_e$ and $R_x$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;

adjacent substituents $R_d$, $R_e$, $R_x$ can be optionally joined to form a ring;

$L_b$ and $L_c$ are each independently selected from any one of the following structures:

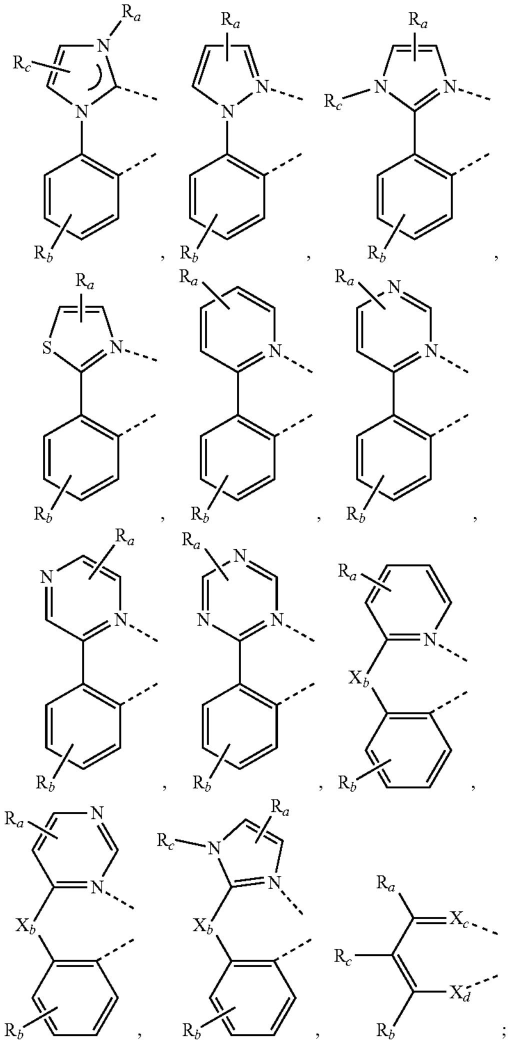

;

$R_a$, $R_b$ and $R_c$ represent, at each occurrence identically or differently, mono-substitution, multiple substitutions or non-substitution;

$X_b$ is selected from the group consisting of: O, S, Se, $NR_{N1}$ and $CR_{C1}R_{C2}$;

$X_c$ and $X_d$ are each independently selected from the group consisting of: O, S, Se and $NR_{N2}$;

$R_a$, $R_b$, $R_c$, $R_{N1}$, $R_{N2}$, $R_{C1}$ and $R_{C2}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;

in structures of $L_b$ and $L_c$, adjacent substituents $R_a$, $R_b$, $R_c$, $R_{N1}$, $R_{N2}$, $R_{C1}$ and $R_{C2}$ can be optionally joined to form a ring;

and, the following case is not comprised: the first compound is

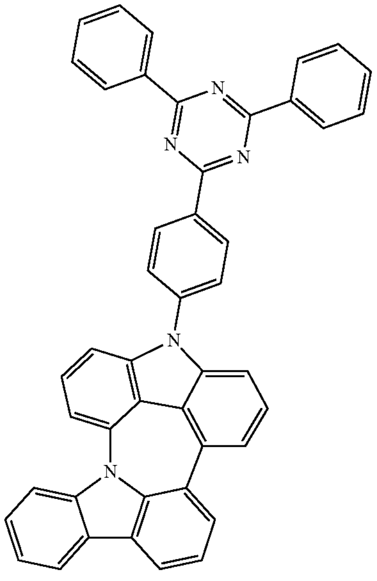 [SMILES: c1ccc(-c2nc(-c3ccccc3)nc(-c3ccc(-n4c5cccc6c7cccc8c9ccccc9n(c9cccc4c9c65)c78)cc3)n2)cc1]

while the second compound is

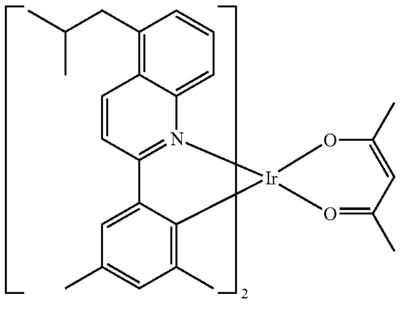
.

In the present disclosure, the expression that adjacent substituents R, $R_f$ can be optionally joined to form a ring is intended to mean that in the presence of substituents R and $R_f$, any one or more of groups of adjacent substituents, such as adjacent substituents R, adjacent substituents $R_f$, and substituents R and $R_f$, can be joined to form a ring. Obviously, in the presence of substituents R and $R_f$, it is possible that none of these groups of substituents are joined to form a ring.

In the present disclosure, the expression that adjacent substituents $R_d$, $R_e$, $R_x$ can be optionally joined to form a ring is intended to mean that in the presence of substituents $R_d$, $R_e$ and $R_x$, any one or more of groups of adjacent substituents, such as adjacent substituents $R_d$, adjacent substituents $R_e$, adjacent substituents $R_x$, adjacent substituents $R_d$ and $R_e$, adjacent substituents $R_d$ and $R_x$, and adjacent substituents $R_e$ and $R_x$, can be joined to form a ring. Obviously, in the presence of substituents $R_d$, $R_e$ and $R_x$, it is possible that none of these groups of substituents are joined to form a ring.

In the present disclosure, the expression that in the structures of $L_b$ and $L_c$, adjacent substituents $R_a$, $R_b$, $R_c$, $R_{N1}$, $R_{N2}$, $R_{C1}$ and $R_{C2}$ can be optionally joined to form a ring is intended to mean that any one or more of groups of adjacent substituents, such as two substituents $R_a$, two substituents $R_b$, two substituents $R_a$ and $R_b$, substituents $R_a$ and $R_c$, substituents $R_b$ and $R_c$, substituents $R_a$ and $R_{N1}$, substituents $R_b$ and $R_{N1}$, substituents $R_a$ and $R_{C1}$, substituents $R_a$ and $R_{C2}$, substituents $R_b$ and $R_{C1}$, substituents $R_b$ and $R_{C2}$, substituents $R_a$ and $R_{N2}$, substituents $R_b$ and $R_{N2}$, and substituents $R_{C1}$ and $R_{C2}$, may be joined to form a ring. Obviously, it is possible that none of these substituents are joined to form a ring.

According to an embodiment of the present disclosure, wherein in Formula 1, the ring A, the ring B and the ring C are, at each occurrence identically or differently, selected from an aromatic ring having 6 to 18 carbon atoms or a heteroaromatic ring having 3 to 18 carbon atoms.

According to an embodiment of the present disclosure, wherein in Formula 1, the ring A, the ring B and the ring C are, at each occurrence identically or differently, selected from an aromatic ring having 6 to 12 carbon atoms or a heteroaromatic ring having 3 to 12 carbon atoms.

According to an embodiment of the present disclosure, wherein in Formula 1, the ring A, the ring B and the ring C are, at each occurrence identically or differently, selected from a five-membered carbocyclic ring, a benzene ring, a five-membered heteroaromatic ring or a six-membered heteroaromatic ring.

According to an embodiment of the present disclosure, wherein in the first compound, H has a structure represented by Formula 1-a:

Formula 1-a

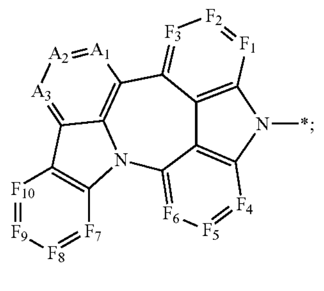

wherein $A_1$ to $A_3$ are, at each occurrence identically or differently, selected from N or CR, and $F_1$ to $F_{10}$ are, at each occurrence identically or differently, selected from $CR_f$ or N;

R and $R_f$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;

adjacent substituents R, $R_f$ can be optionally joined to form a ring.

According to an embodiment of the present disclosure, wherein in the first compound, R and $R_f$ are, at each occurrence identically or differently, selected from the group consisting of: hydrogen, deuterium, halogen, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted amino having 0 to 20 carbon atoms, a cyano group, an isocyano group, a hydroxyl group, a sulfanyl group and combinations thereof;

adjacent substituents R, $R_f$ can be optionally joined to form a ring.

According to an embodiment of the present disclosure, wherein in the first compound, at least one of R and $R_f$ is selected from deuterium, substituted or unsubstituted aryl having 6 to 30 carbon atoms or substituted or unsubstituted heteroaryl having 3 to 30 carbon atoms.

According to an embodiment of the present disclosure, wherein in the first compound, at least one of R and $R_f$ is selected from deuterium, phenyl, biphenyl or pyridyl.

According to an embodiment of the present disclosure, wherein in the first compound, for adjacent substituents R in $A_1$ to $A_3$, adjacent substituents $R_f$ in $F_1$ to $F_3$, adjacent substituents $R_f$ in $F_4$ to $F_6$, and adjacent substituents $R_f$ in $F_7$ to $F_{10}$, at least one group of these groups of adjacent substituents is joined to form a ring.

According to an embodiment of the present disclosure, wherein in the first compound, the H is selected from the group consisting of the following structures:

H-1

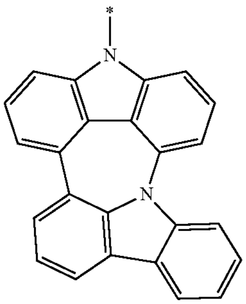

,

H-2

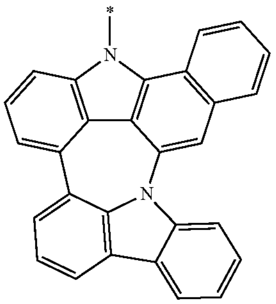

,

H-3

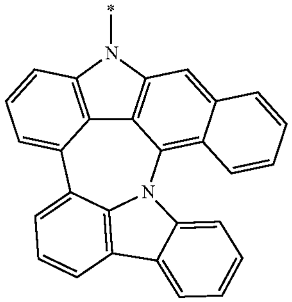

,

H-4

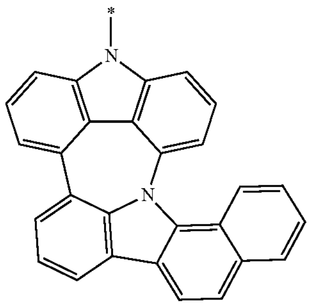

,

H-5

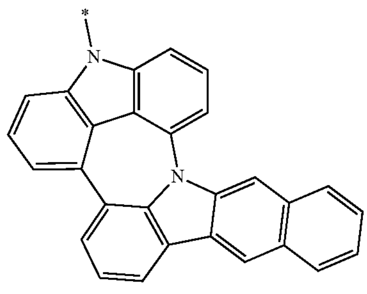

,

-continued
H-6
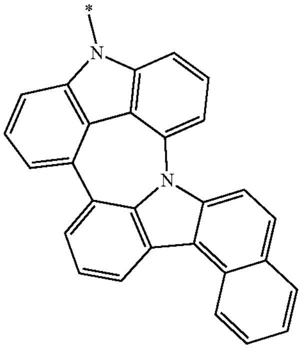
,
H-7
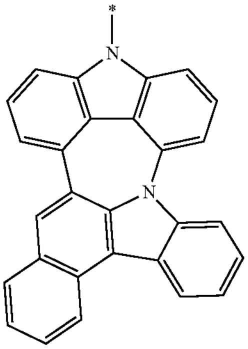
,
H-8
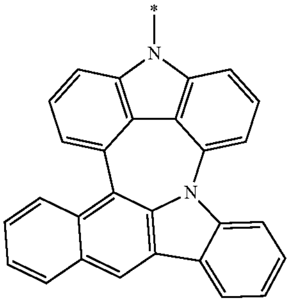
,
H-9
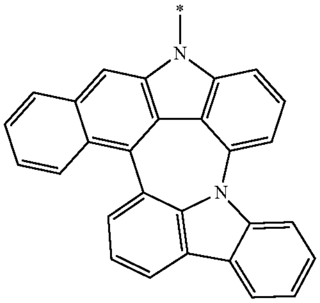
,
H-10
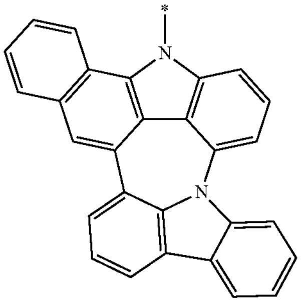
,
-continued
H-11
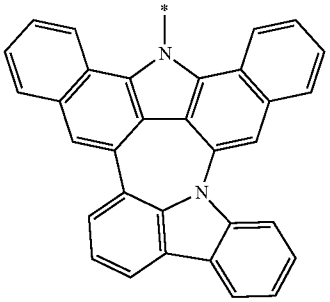
,
H-12
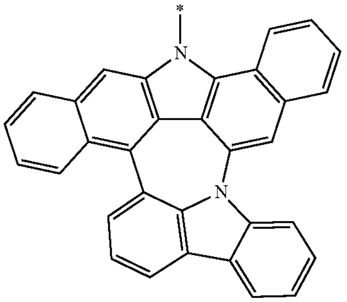
,
H-13
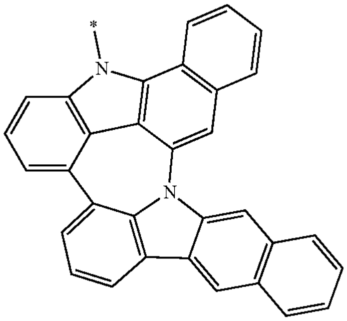
,
H-14
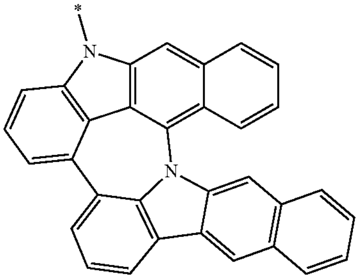
,
H-15
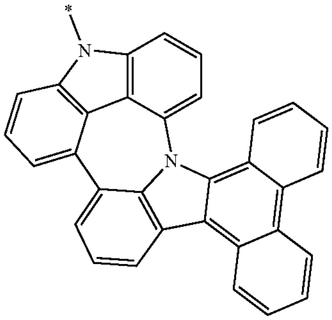
, -continued
H-16
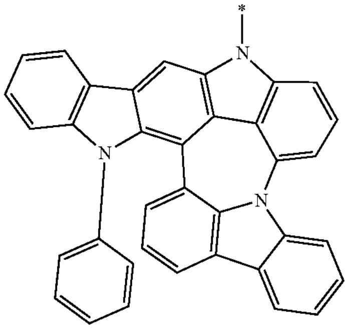
,
H-17
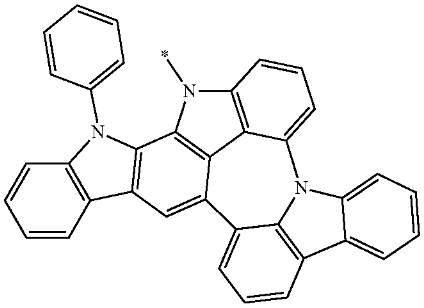
,
H-18
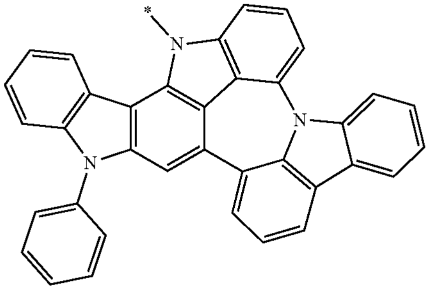
,
H-19
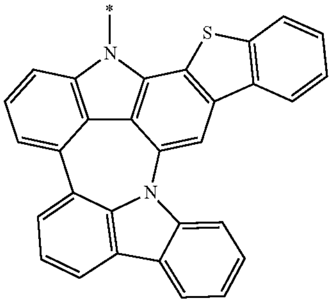
,
H-20
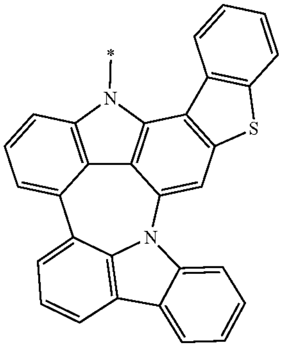
,
-continued
H-21
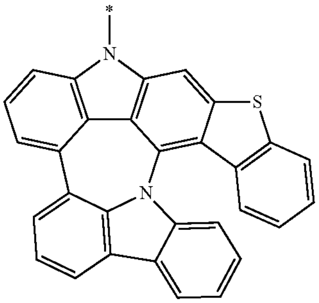
,
H-22
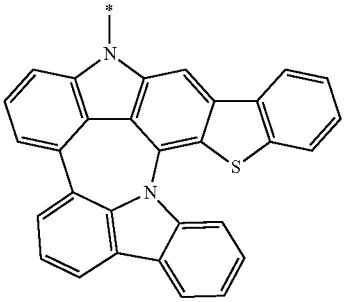
,
H-23
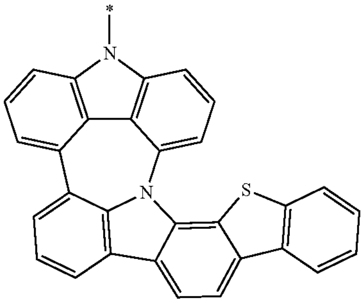
,
H-24
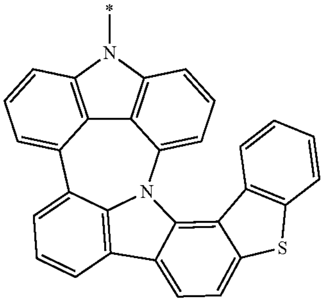
,
H-25
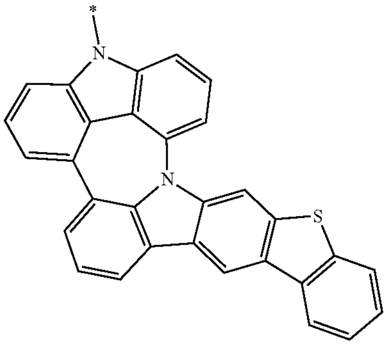
, -continued
H-26
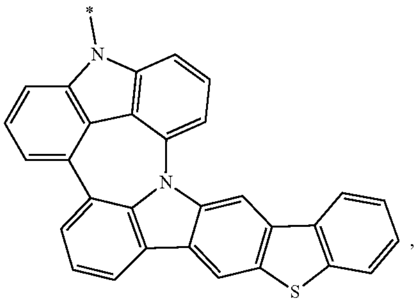,
H-27
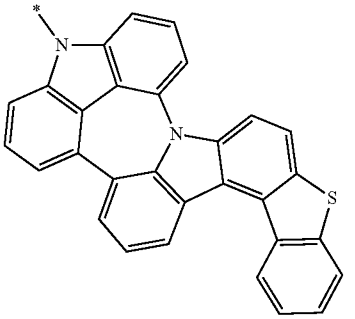,
H-28
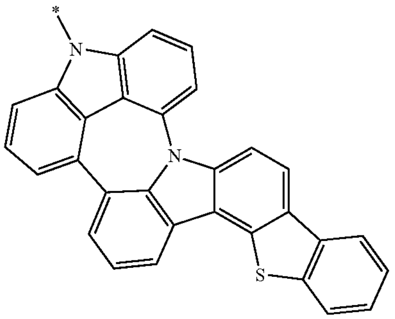,
H-29
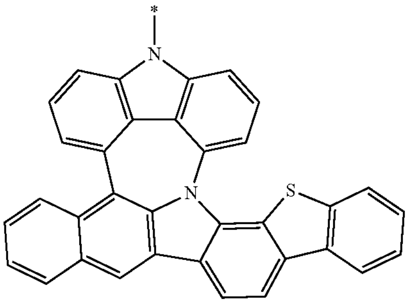,
H-30
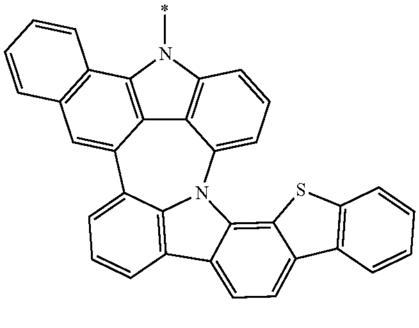,
-continued
H-31
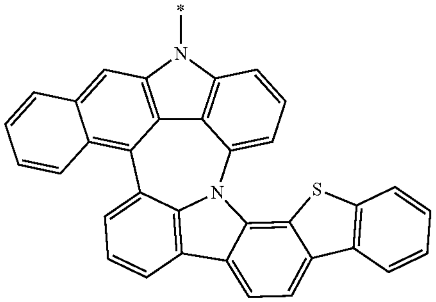,
H-32
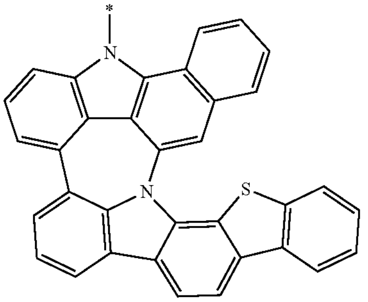,
H-33
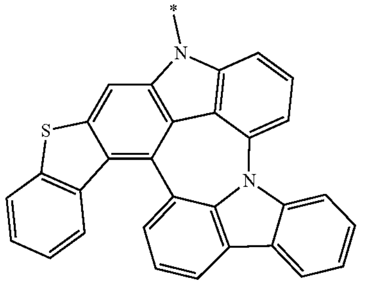,
H-34
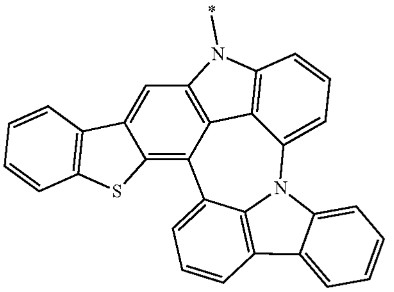,
H-35
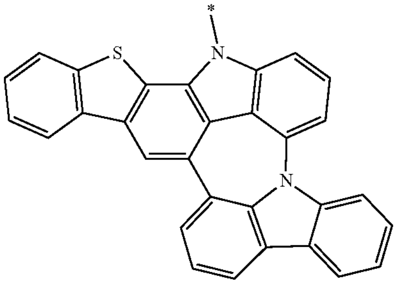, H-36
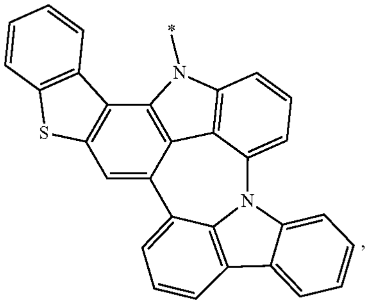
H-37
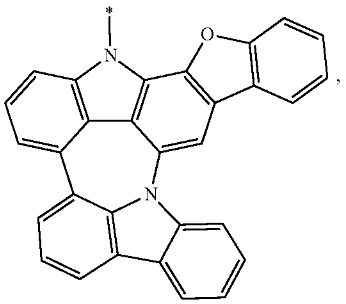
H-38
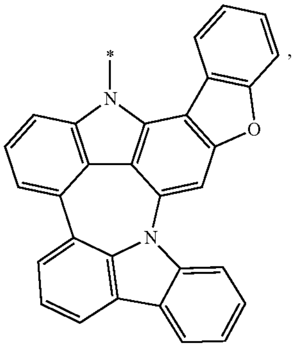
H-39
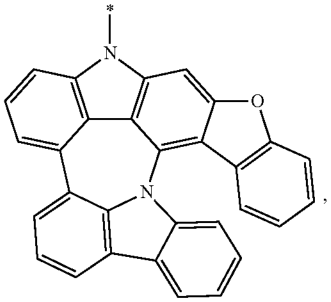
H-40
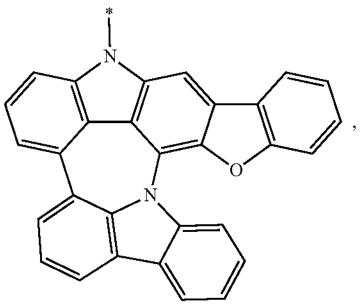
H-41
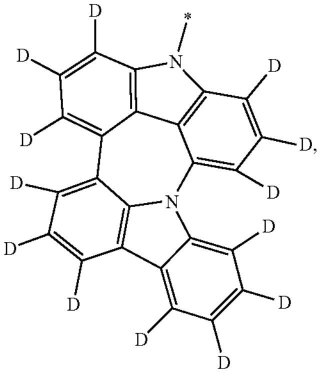
H-42
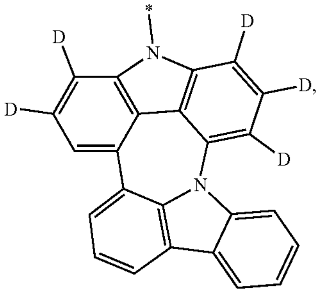
H-43
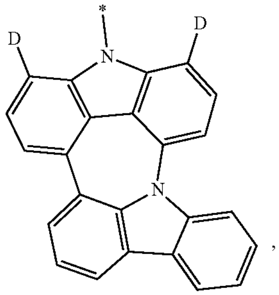
H-44
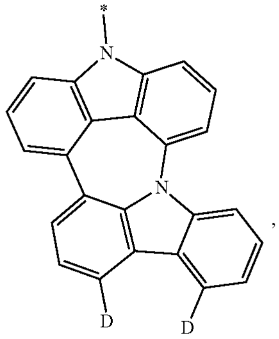

-continued
H-45
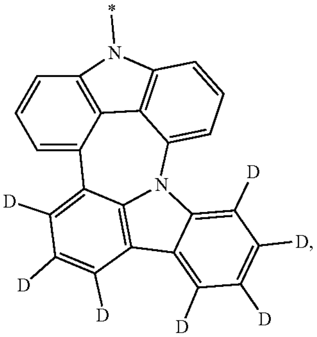
H-46
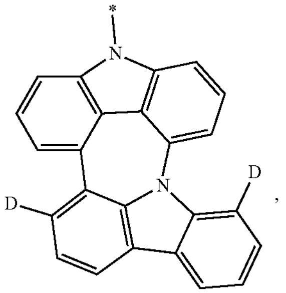
H-47
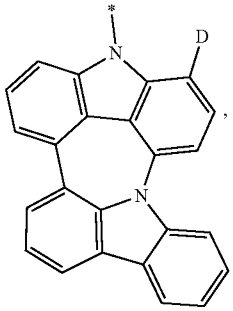
H-48
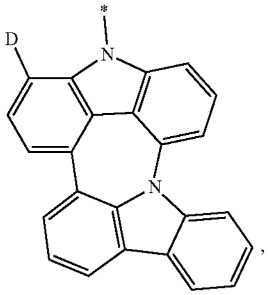
H-49
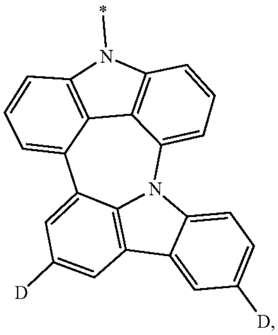
-continued
H-50
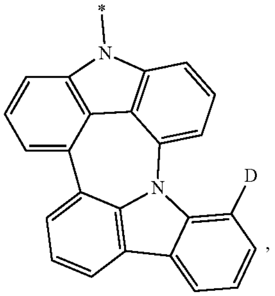
H-51
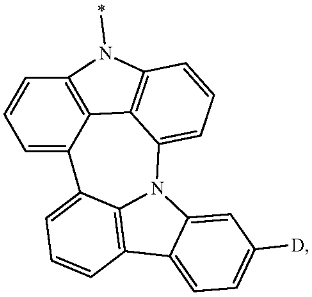
H-52
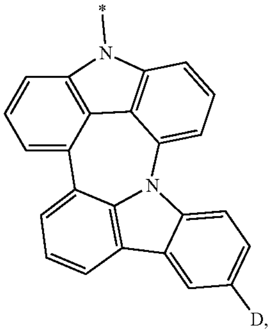
H-53
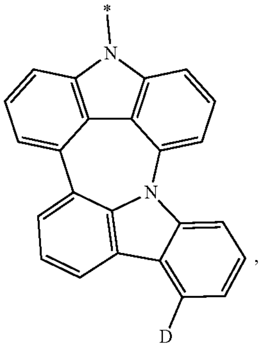
H-54
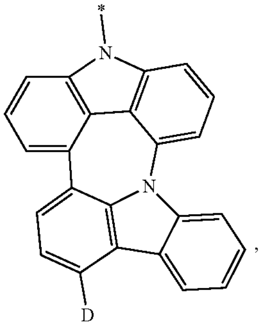

-continued

H-55

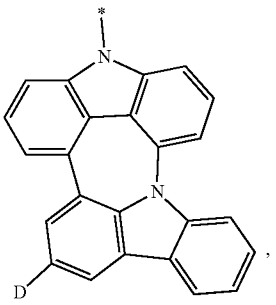

H-56

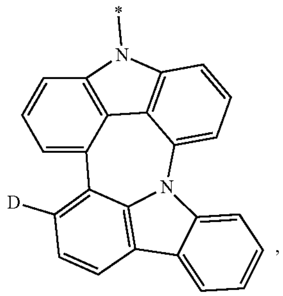

H-57

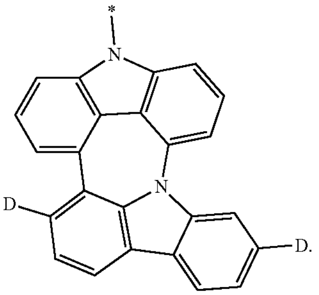

According to an embodiment of the present disclosure, wherein hydrogens in the structures of H-1 to H-57 can be partially or fully substituted with deuterium.

According to an embodiment of the present disclosure, wherein in the first compound, the E has a structure represented by any one of Formula 2-a to Formula 2-h:

Formula 2-a

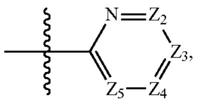

Formula 2-b

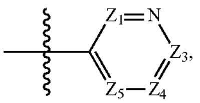

Formula 2-c

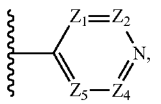

Formula 2-d

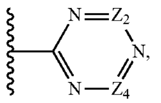

-continued

Formula 2-e

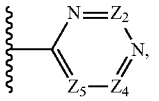

Formula 2-f

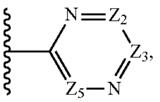

Formula 2-g

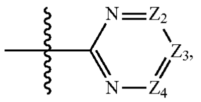

Formula 2-h

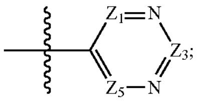

wherein $Z_1$ to $Z_5$ are, at each occurrence identically or differently, selected from $CR_z$;

wherein $R_z$ is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof.

According to a preferred embodiment of the present disclosure, wherein the $R_z$ is, at each occurrence identically or differently, selected from the group consisting of: hydrogen, deuterium, halogen, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms and combinations thereof.

According to a preferred embodiment of the present disclosure, wherein the $R_z$ is, at each occurrence identically or differently, selected from the group consisting of: hydrogen, deuterium, phenyl, naphthyl, biphenyl, terphenyl, fluorenyl, dibenzofuranyl, dibenzothienyl, pyridyl and combinations thereof.

According to an embodiment of the present disclosure, wherein in the first compound, the E is selected from substituted or unsubstituted triazinyl.

According to an embodiment of the present disclosure, wherein in the first compound, the E is selected from the group consisting of the following structures:
E-1
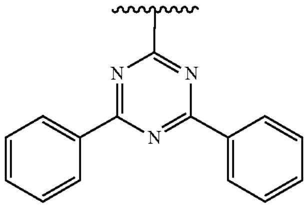
E-2
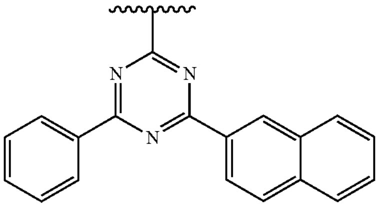
,
E-3
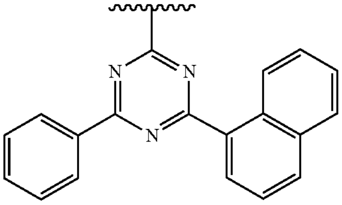
,
E-4
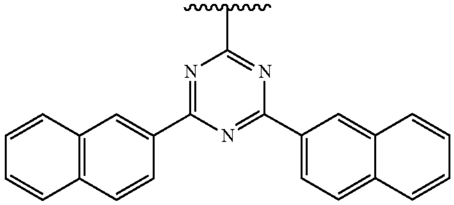
,
E-5
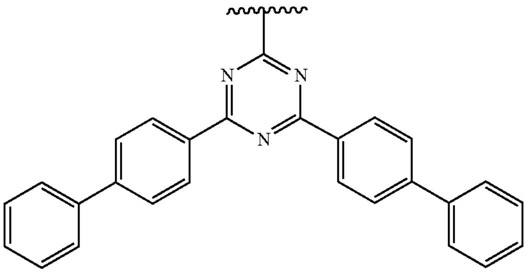
,
E-6
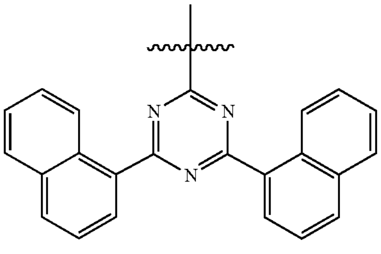
,
-continued
E-7
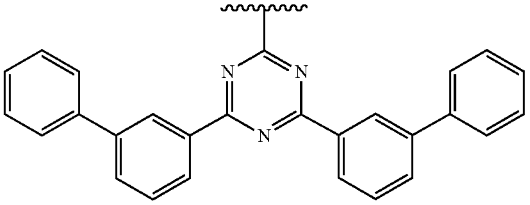
,
E-8
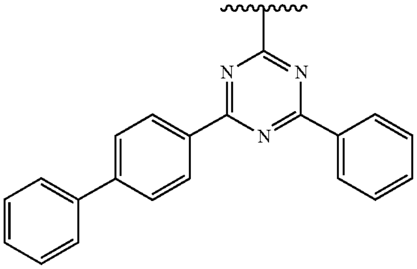
,
E-9
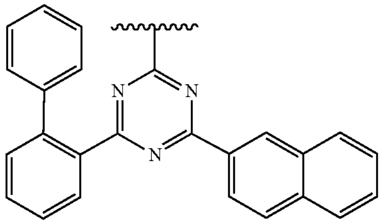
,
E-10
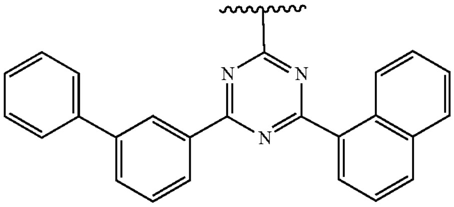
,
E-11
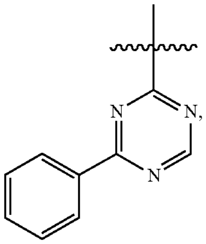
,
E-12
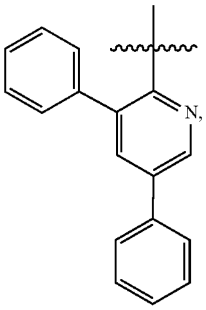
, -continued
E-13
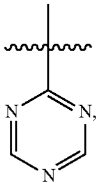,
E-14
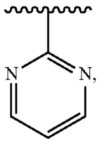,
E-15
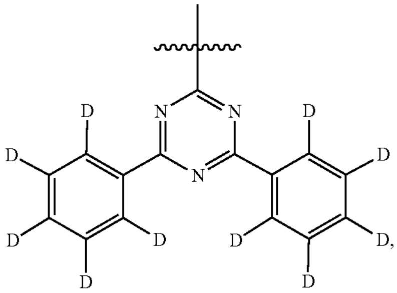,
E-16
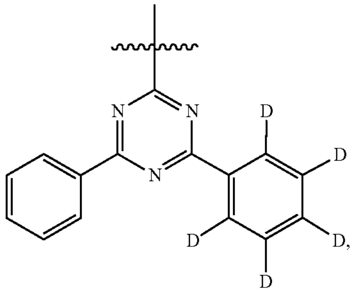,
E-17
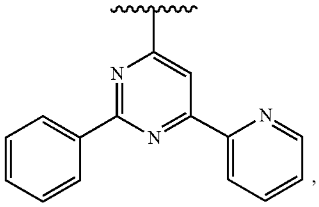,
E-18
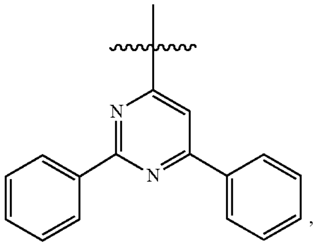,
-continued
E-19
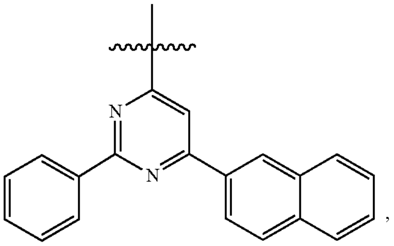,
E-20
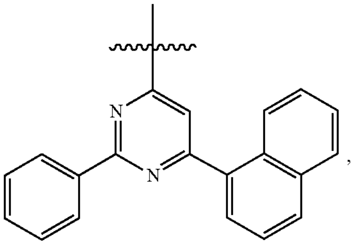,
E-21
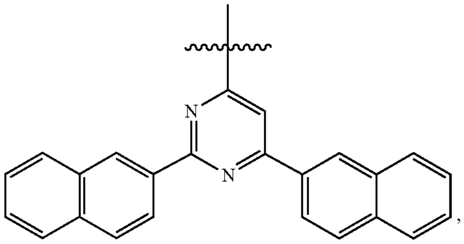,
E-22
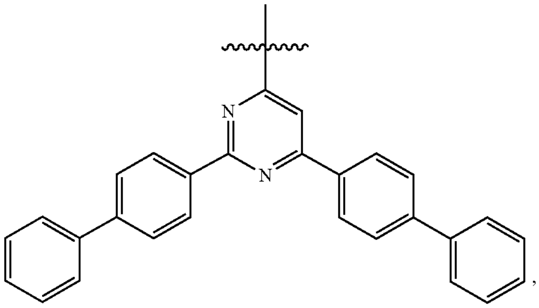,
E-23
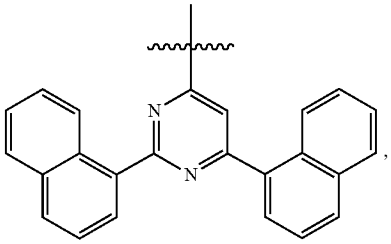,
E-24
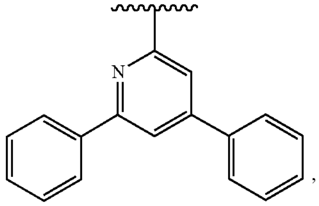, -continued
E-25
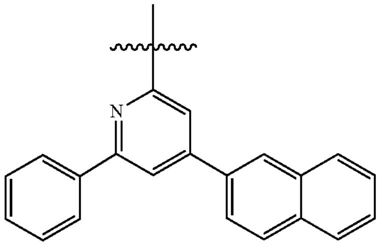
,
E-26
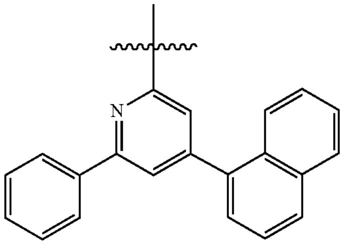
,
E-27
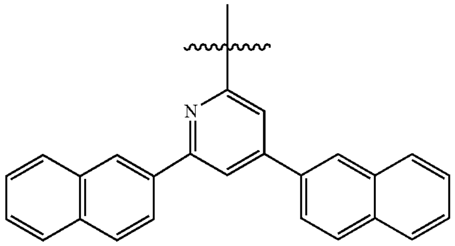
,
E-28
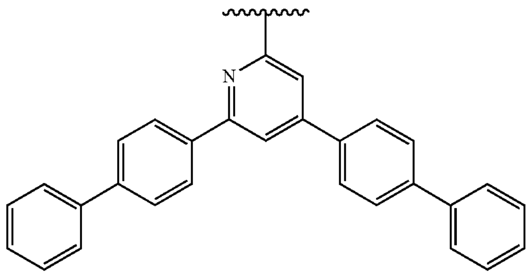
,
E-29
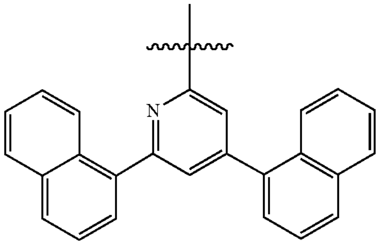
,
E-30
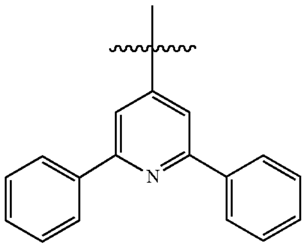
,
-continued
E-31
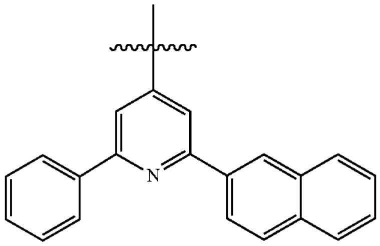
,
E-32
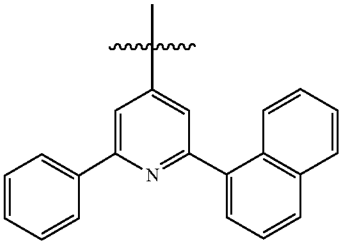
,
E-33
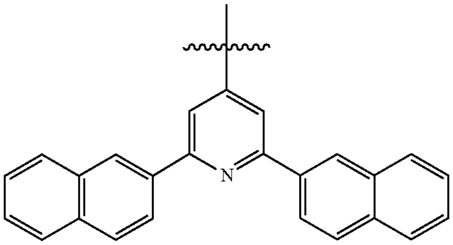
,
E-34
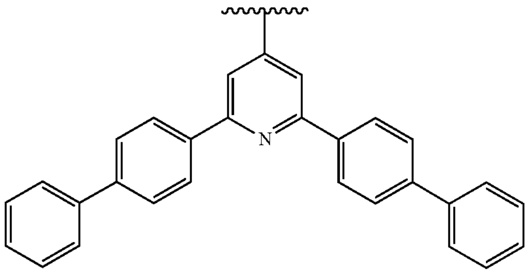
,
E-35
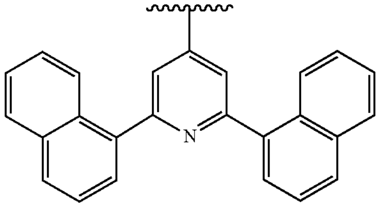
,
E-36
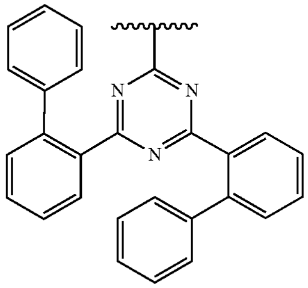
, -continued
E-37
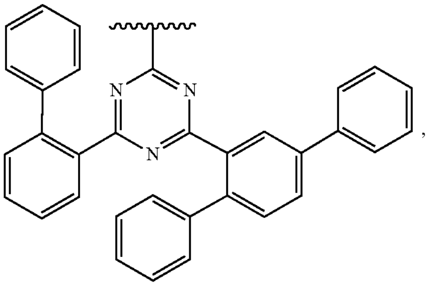
E-38
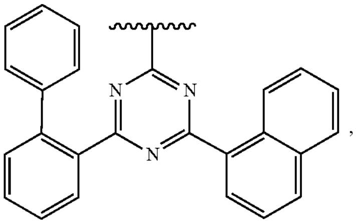
E-39
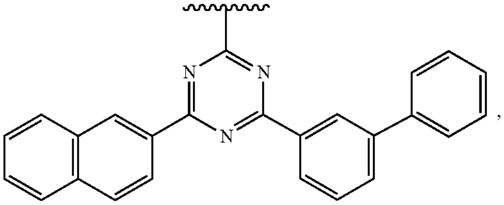
E-40
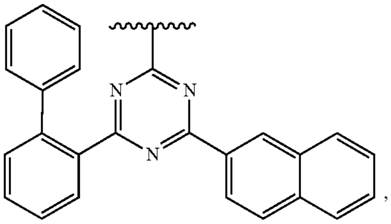
E-41
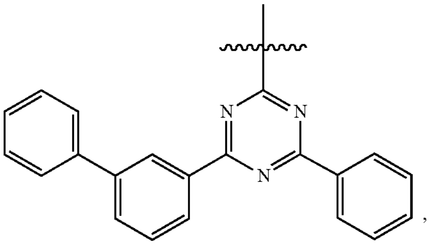
E-42
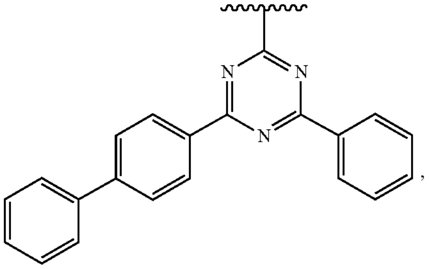
-continued
E-43
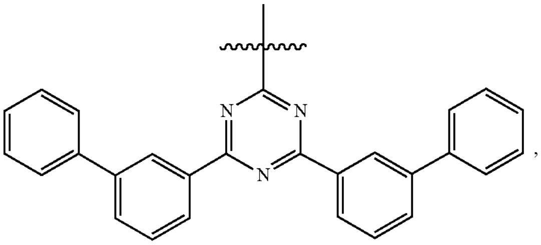
E-44
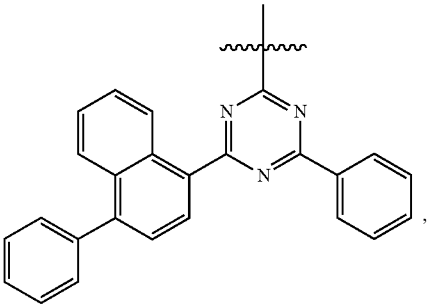
E-45
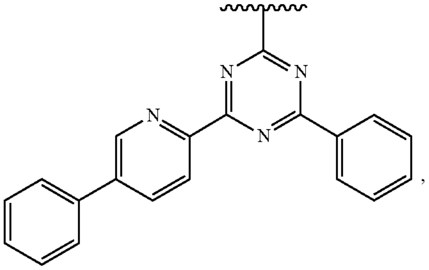
E-46
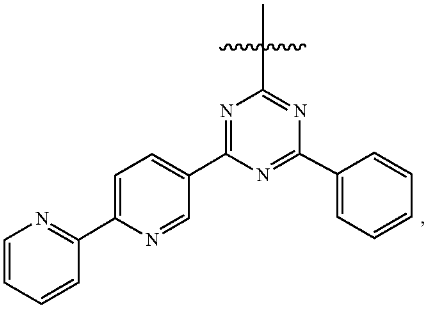
E-47
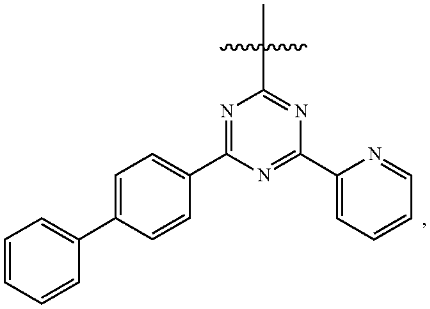

-continued
E-48
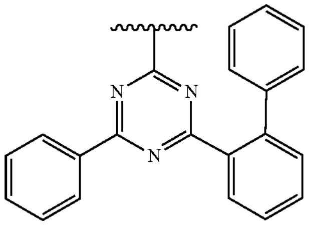
,
E-49
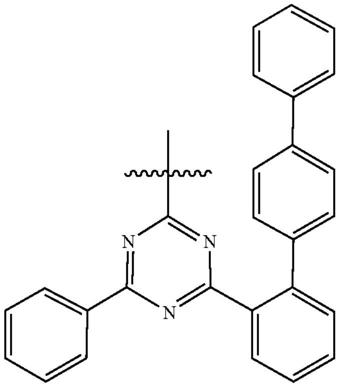
,
E-50
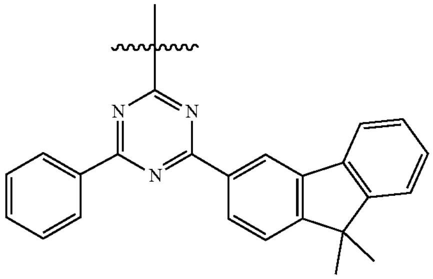
,
E-51
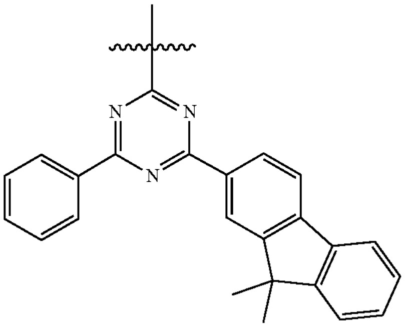
,
E-52
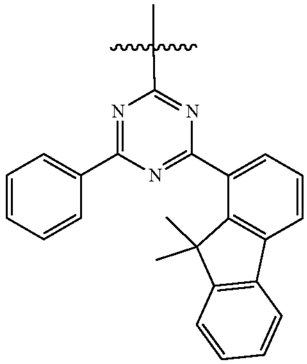
,
-continued
E-53
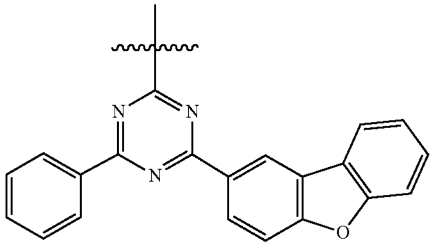
,
E-54
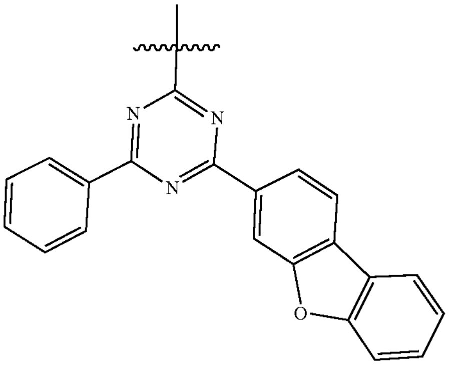
,
E-55
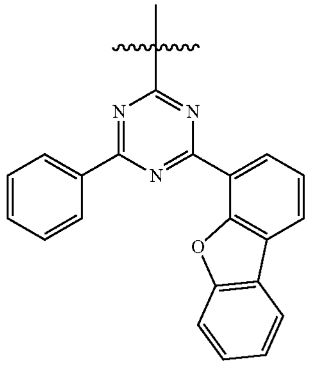
,
E-56
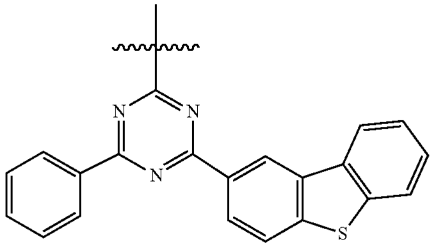
,
E-57
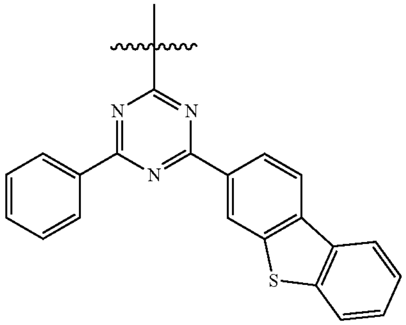
, E-58
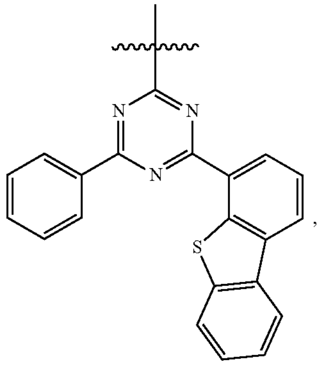
E-59
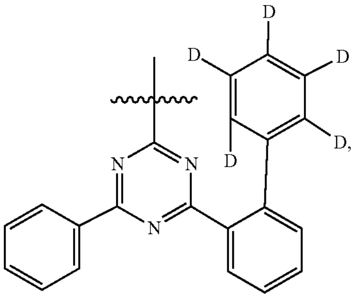
E-60
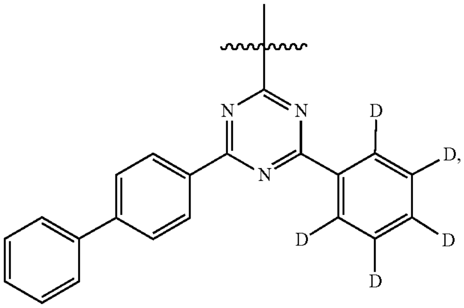
E-61
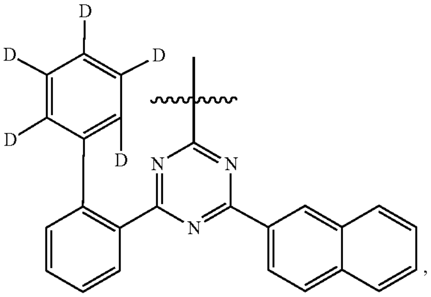
E-62
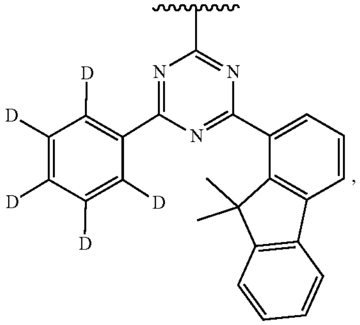
E-63
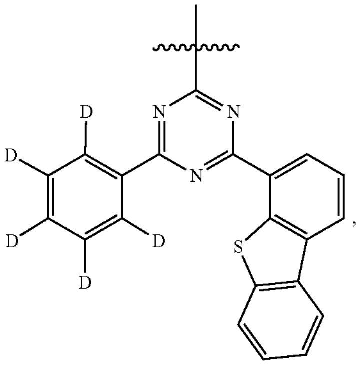
E-64
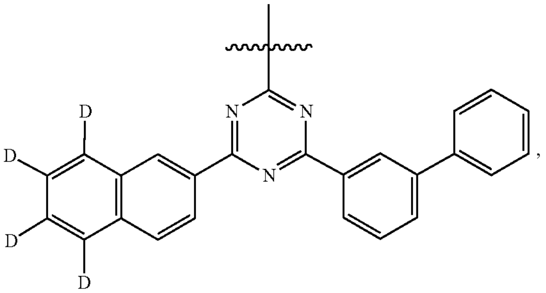
E-65
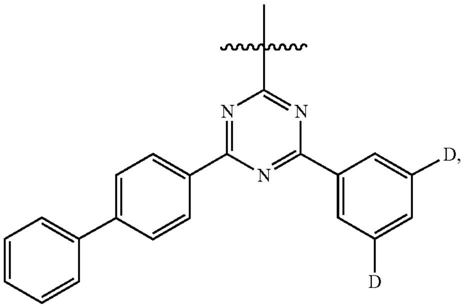

-continued

E-66

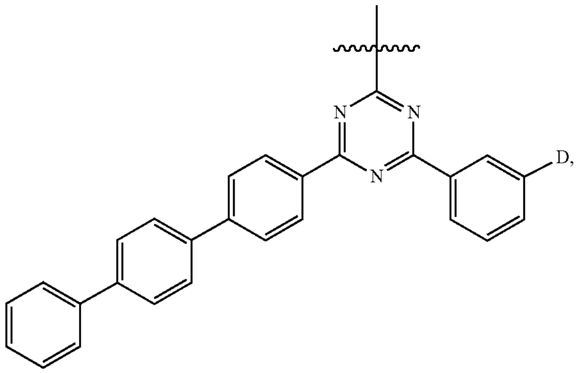

E-67

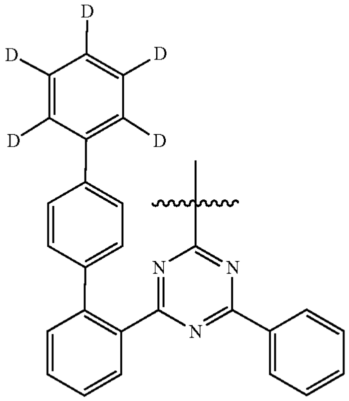

,

E-68

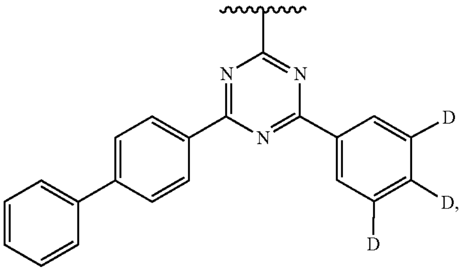

E-69

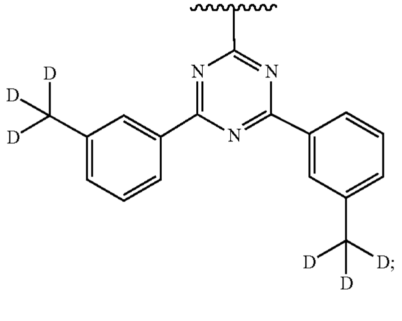

wherein in the above structures, "〰" represents the position where the structure is joined to the structure of L.

According to an embodiment of the present disclosure, wherein hydrogens in the structures of E-1 to E-69 can be partially or fully substituted with deuterium.

According to an embodiment of the present disclosure, wherein in the first compound, the L is selected from a single bond or substituted or unsubstituted arylene having 6 to 30 carbon atoms.

According to an embodiment of the present disclosure, wherein in the first compound, the L is selected from the group consisting of: a single bond, phenylene, naphthylene, biphenylene, terphenylene, triphenylenylene, phenanthrylene and fluorenylidene.

According to an embodiment of the present disclosure, wherein in the first compound, the L is selected from the group consisting of the following structures:

L-0 a single bond,

L-1

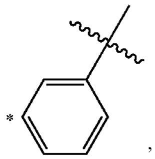

,

L-2

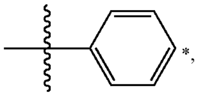

L-3

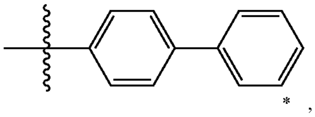

L-4

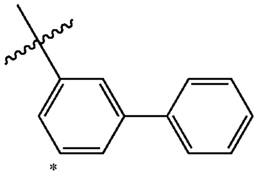

,

L-5

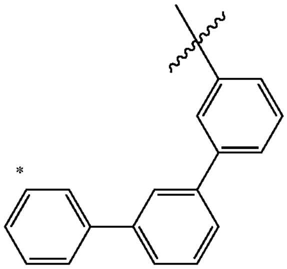

,

L-6

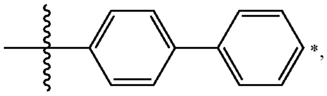

L-7

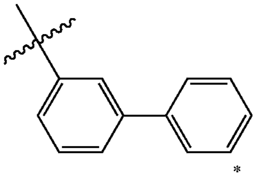

-continued
L-8
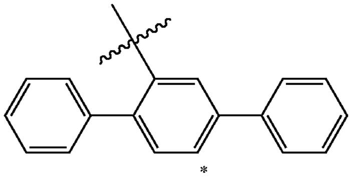
,
L-9
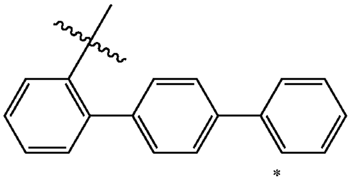
,
L-10
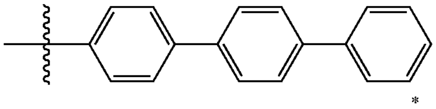
,
L-11
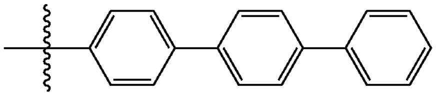
,
L-12
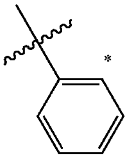
,
L-13
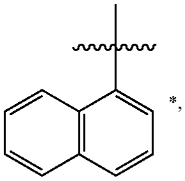
,
L-14
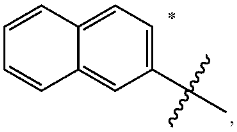
,
L-15
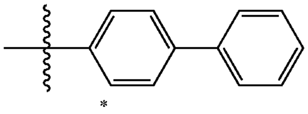
,
L-16
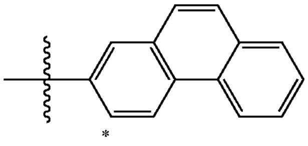
,
-continued
L-17
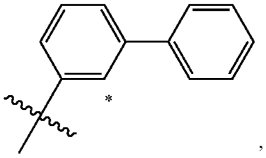
,
L-18
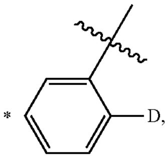
,
L-19
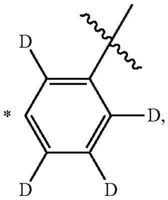
,
L-20
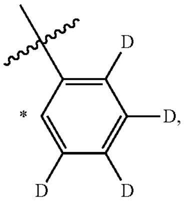
,
L-21
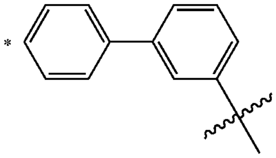
,
L-22
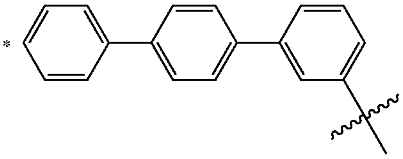
,
L-23
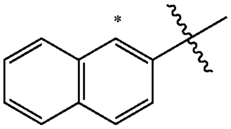
,
L-24
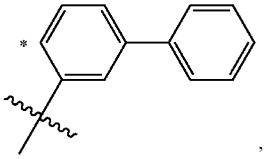
,
L-25
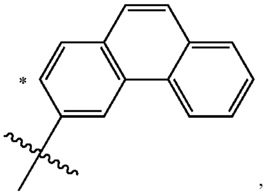
, -continued

L-26

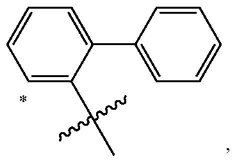

,

L-27

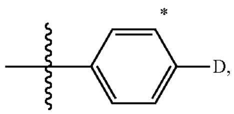

L-28

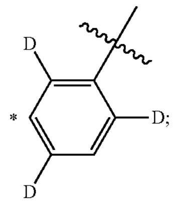

wherein in the above structures, "*" represents the position where the structure is joined to the structure of H, and " ∿∿ " represents the position where the structure is joined to the structure of E.

According to an embodiment of the present disclosure, wherein hydrogens in the structures of L-1 to L-28 can be partially or fully substituted with deuterium.

According to an embodiment of the present disclosure, wherein the first compound is selected from the group consisting of Compound 1 to Compound 520, wherein the specific structures of Compound 1 to Compound 520 are referred to claim 9.

According to an embodiment of the present disclosure, wherein in the second compound, the metal M is selected from Ir, Rh, Re, Os, Pt, Au or Cu.

According to an embodiment of the present disclosure, wherein in the second compound, the M is selected from Ir, Pt or Os.

According to an embodiment of the present disclosure, wherein in the second compound, the M is Ir.

According to an embodiment of the present disclosure, wherein in the second compound, the $L_a$ has a structure represented by any one of Formula 3-1 to Formula 3-5:

Formula 3-1

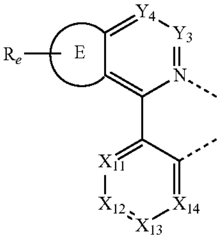

-continued

Formula 3-2

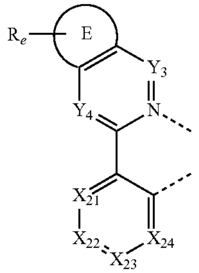

Formula 3-3

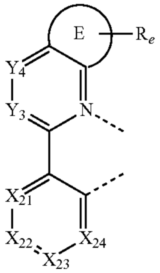

Formula 3-4

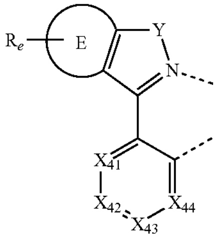

Formula 3-5

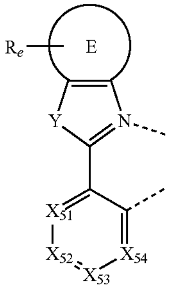

;

wherein, the ring E is selected from a five-membered unsaturated carbocyclic ring, a benzene ring, a five-membered heteroaromatic ring or a six-membered heteroaromatic ring;

$R_e$ represents, at each occurrence identically or differently, mono-substitution, multiple substitutions or non-substitution;

$X_{11}$ to $X_{14}$ are, at each occurrence identically or differently, selected from $CR_{x1}$ or N; $X_{21}$ to $X_{24}$ are, at each occurrence identically or differently, selected from $CR_{x2}$ or N; $X_{31}$ to $X_{34}$ are, at each occurrence identically or differently, selected from $CR_{x3}$ or N; $X_{41}$ to $X_{44}$ are, at each occurrence identically or differently, selected from $CR_{x4}$ or N; and $X_{51}$ to $X_{54}$ are, at each occurrence identically or differently, selected from $CR_{x5}$ or N;

Y is, at each occurrence identically or differently, selected from O, S, Se, $NR_{d1}$, $CR_{d1}R_{d1}$ or $SiR_{d1}R_{d1}$; wherein in the presence of two $R_{d1}$, the two $R_{d1}$ may be the same or different; for example, when Y is selected from $CR_{d1}R_{d1}$, the two $R_{d1}$ may be the same or different; in another example, when Y is selected from $SiR_{d1}R_{d1}$, the two $R_{d1}$ may be the same or different;

preferably, Y is, at each occurrence identically or differently, selected from O or S;

$Y_3$ and $Y_4$ are, at each occurrence identically or differently, selected from $CR_d$ or N;

$R_{x1}$, $R_{x2}$, $R_{x3}$, $R_{x4}$, $R_{x5}$, $R_{d1}$, $R_d$ and $R_e$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;

adjacent substituents $R_{x1}$, $R_{x2}$, $R_{x4}$, $R_{x5}$, $R_{d1}$, $R_d$ and $R_e$ can be optionally joined to form a ring;

when $R_{x3}$ is selected from substituted or unsubstituted alkyl having 1 to 20 carbon atoms, substituted or unsubstituted cycloalkyl having 3 to 20 ring carbon atoms, substituted or unsubstituted arylalkyl having 7 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms or substituted or unsubstituted amino having 0 to 20 carbon atoms, adjacent substituents $R_{x3}$ can be optionally joined to form a ring.

In the present disclosure, the expression that adjacent substituents $R_{x1}$, $R_{x2}$, $R_{x4}$, $R_{x5}$, $R_{d1}$, $R_d$ and $R_e$ can be optionally joined to form a ring is intended to mean that in the presence of substituents $R_{x1}$, $R_{x2}$, $R_{x4}$, $R_{x5}$, $R_e$, $R_d$ or $R_{d1}$, any one or more of groups of adjacent substituents, such as adjacent substituents $R_{x1}$, adjacent substituents $R_{x2}$, adjacent substituents $R_{x4}$, adjacent substituents $R_{x5}$, adjacent substituents $R_{d1}$, substituents $R_{x1}$ and $R_d$, substituents $R_{x1}$ and $R_e$, substituents $R_{x2}$ and $R_d$, substituents $R_{x4}$ and $R_e$, substituents $R_{x5}$ and $R_{d1}$, substituents $R_{d1}$ and $R_e$, and substituents $R_d$ and $R_e$, can be joined to form a ring. Obviously, it is possible that none of these substituents are joined to form a ring.

In the present disclosure, the expression that when $R_{x3}$ is selected from the group of substituents, adjacent substituents $R_{x3}$ can be optionally joined to form a ring is intended to mean that only when substituent $R_{x3}$ is present and $R_{x3}$ is selected from the group consisting of alkyl, cycloalkyl, arylalkyl, alkenyl, aryl, heteroaryl, alkylsilyl, arylsilyl and amino, can adjacent substituents $R_{x3}$ be joined to form a ring; and when substituent $R_{x3}$ is selected from substituents that are not in the above group of substituents, adjacent substituents $R_{x3}$ cannot be joined to form a ring. Obviously, when substituent $R_{x3}$ is selected from the above group of substituents, it is possible that adjacent substituents $R_{x3}$ are not joined to form a ring.

According to an embodiment of the present disclosure, wherein in the second compound, the $L_a$ has a structure represented by any one of Formula 3-6 to Formula 3-13:

Formula 3-6

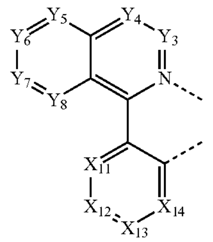

Formula 3-7

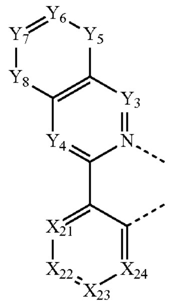

Formula 3-8

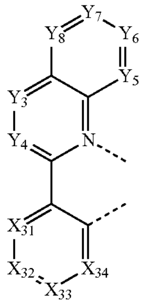

Formula 3-9

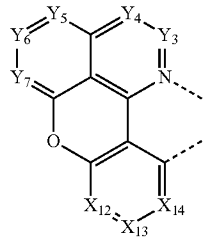

Formula 3-10

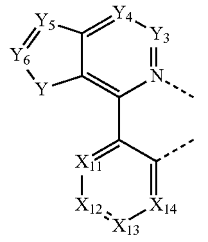

-continued

Formula 3-11

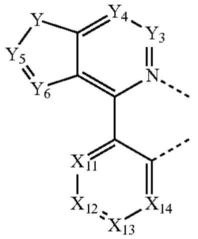

Formula 3-12

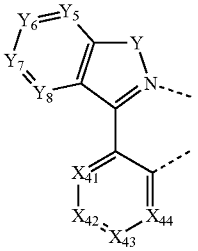

Formula 3-13

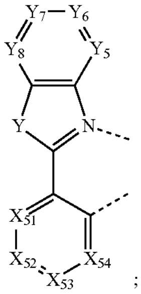

;

wherein $X_{11}$ to $X_{14}$ are, at each occurrence identically or differently, selected from $CR_{x1}$ or N; $X_{21}$ to $X_{24}$ are, at each occurrence identically or differently, selected from $CR_{x2}$ or N; $X_{31}$ to $X_{34}$ are, at each occurrence identically or differently, selected from $CR_{x3}$ or N; $X_{41}$ to $X_{44}$ are, at each occurrence identically or differently, selected from $CR_{x4}$ or N; and $X_{51}$ to $X_{54}$ are, at each occurrence identically or differently, selected from $CR_{x5}$ or N;

$Y_3$ and $Y_4$ are, at each occurrence identically or differently, selected from $CR_d$ or N;

$Y_5$, $Y_6$, $Y_7$ and $Y_8$ are, at each occurrence identically or differently, selected from $CR_e$ or N;

Y is, at each occurrence identically or differently, selected from O, S, Se, $NR_{d1}$, $CR_{d1}R_{d1}$ or $SiR_{d1}R_{d1}$; wherein in the presence of two $R_{d1}$, the two $R_{d1}$ may be the same or different; for example, when Y is selected from $CR_{d1}R_{d1}$, the two $R_{d1}$ may be the same or different; in another example, when Y is selected from $SiR_{d1}R_{d1}$, the two $R_{d1}$ may be the same or different;

$R_{x1}$, $R_{x2}$, $R_{x3}$, $R_{x4}$, $R_{x5}$, $R_{d1}$, $R_d$ and $R_e$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;

adjacent substituents $R_{x1}$, $R_{x2}$, $R_{x4}$, $R_{x5}$, $R_{d1}$, $R_d$ and $R_e$ can be optionally joined to form a ring;

when $R_{x3}$ is selected from substituted or unsubstituted alkyl having 1 to 20 carbon atoms, substituted or unsubstituted cycloalkyl having 3 to 20 ring carbon atoms, substituted or unsubstituted arylalkyl having 7 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms or substituted or unsubstituted amino having 0 to 20 carbon atoms, adjacent substituents $R_{x3}$ can be optionally joined to form a ring.

According to an embodiment of the present disclosure, wherein the $L_a$ has a structure represented by any one of Formula 3-6 to Formula 3-13, wherein the Y is, at each occurrence identically or differently, selected from O or S.

According to an embodiment of the present disclosure, wherein the $L_a$ has a structure represented by Formula 3-6, Formula 3-7, Formula 3-9, Formula 3-10, Formula 3-11, Formula 3-12 or Formula 3-13.

According to an embodiment of the present disclosure, wherein the $L_a$ has a structure represented by Formula 3-6 or Formula 3-9.

According to an embodiment of the present disclosure, wherein in Formula 3-6 to Formula 3-11, at least one of $Y_3$ and $Y_4$ is N.

According to an embodiment of the present disclosure, wherein in Formula 3-6, Formula 3-7, Formula 3-9, Formula 3-10 and Formula 3-11, $Y_4$ is N; and in Formula 3-8, $Y_3$ is N.

According to an embodiment of the present disclosure, wherein in Formula 3-6 to Formula 3-13, $Y_3$ and $Y_4$ are, at each occurrence identically or differently, selected from $CR_d$, and $Y_5$, $Y_6$, $Y_7$ and $Y_8$ are, at each occurrence identically or differently, selected from $CR_e$.

According to an embodiment of the present disclosure, wherein in Formula 3-6 to Formula 3-13, $Y_3$ and/or $Y_4$ are/is selected from $CR_d$, and the $R_d$ is, at each occurrence identically or differently, selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof.

According to an embodiment of the present disclosure, wherein in Formula 3-6 to Formula 3-13, $Y_3$ and/or $Y_4$ are/is selected from $CR_d$, and the $R_d$ is, at each occurrence identically or differently, selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms and combinations thereof.

According to an embodiment of the present disclosure, wherein in Formula 3-6 to Formula 3-13, at least one or two of $Y_5$ to $Y_8$ are selected from $CR_e$, and the $R_e$ is, at each occurrence identically or differently, selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof.

According to an embodiment of the present disclosure, wherein in Formula 3-6 to Formula 3-13, at least one or two of $Y_5$ to $Y_8$ are selected from $CR_e$, and the $R_e$ is, at each occurrence identically or differently, selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms and combinations thereof.

According to an embodiment of the present disclosure, wherein in Formula 3-6 and Formula 3-9, $Y_6$ is selected from $CR_e$; in Formula 3-8, $Y_4$ is selected from $CR_d$ and/or at least one of $Y_6$ to $Y_8$ is selected from $CR_e$; in Formula 3-10 and Formula 3-11, at least one of $Y_5$ and $Y_6$ is $CR_e$; and the $R_d$ and $R_e$ are, at each occurrence identically or differently, selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof.

According to an embodiment of the present disclosure, wherein in Formula 3-6 and Formula 3-9, $Y_6$ is selected from $CR_e$; in Formula 3-8, $Y_4$ is selected from $CR_d$ and/or at least one of $Y_6$ to $Y_8$ is selected from $CR_e$; in Formula 3-10 and Formula 3-11, at least one of $Y_5$ and $Y_6$ is $CR_e$; and the $R_d$ and $R_e$ are, at each occurrence identically or differently, selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms and combinations thereof.

According to an embodiment of the present disclosure, wherein in Formula 3-10 and Formula 3-11, at least one of $Y_5$ and $Y_6$ is selected from $CR_e$, and the $R_e$ is, at each occurrence identically or differently, selected from the group consisting of: substituted or unsubstituted alkyl having 1 to 20 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof.

According to an embodiment of the present disclosure, wherein in Formula 3-10 and Formula 3-11, $Y_5$ and $Y_6$ are each independently selected from $CR_e$, and two $R_e$ are joined to form a five-membered aromatic ring, a benzene ring, a five-membered heteroaromatic ring or a six-membered heteroaromatic ring.

According to an embodiment of the present disclosure, wherein in Formula 3-6 to Formula 3-13, at least one or two of $X_{11}$ to $X_{14}$ are selected from $CR_{x1}$, at least one or two of $X_{21}$ to $X_{24}$ are selected from $CR_{x2}$, at least one or two of $X_{31}$ to $X_{34}$ are selected from $CR_{x3}$, at least one or two of $X_{41}$ to $X_{44}$ are selected from $CR_{x4}$, at least one or two of $X_{51}$ to $X_{54}$ are selected from $CR_{x5}$, and the $R_{x1}$, $R_{x2}$, $R_{x3}$, $R_{x4}$ and $R_{x5}$ are, at each occurrence identically or differently, selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof.

According to an embodiment of the present disclosure, wherein in Formula 3-6 to Formula 3-13, at least one or two of $X_{11}$ to $X_{14}$ are selected from $CR_{x1}$, at least one or two of $X_{21}$ to $X_{24}$ are selected from $CR_{x2}$, at least one or two of $X_{31}$ to $X_{34}$ are selected from $CR_{x3}$, at least one or two of $X_{41}$ to $X_{44}$ are selected from $CR_{x4}$, at least one or two of $X_{51}$ to $X_{54}$ are selected from $CR_{x5}$, and the $R_{x1}$, $R_{x2}$, $R_{x3}$, $R_{x4}$ and $R_{x5}$ are, at each occurrence identically or differently, selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms and combinations thereof.

According to an embodiment of the present disclosure, wherein in Formula 3-6 to Formula 3-13, $X_{12}$ and/or $X_{14}$ are/is selected from $CR_{x1}$, $X_{22}$ and/or $X_{24}$ are/is selected from $CR_{x2}$, $X_{32}$ and/or $X_{34}$ are/is selected from $CR_{x3}$, $X_{42}$ and/or $X_{44}$ are/is selected from $CR_{x4}$, $X_{52}$ and/or $X_{54}$ are/is selected from $CR_{x5}$, and the $R_{x1}$, $R_{x2}$, $R_{x3}$, $R_{x4}$ and $R_{x5}$ are, at each occurrence identically or differently, selected from the group consisting of: substituted or unsubstituted alkyl having 1 to 10 carbon atoms, substituted or unsubstituted cycloalkyl having 3 to 10 ring carbon atoms, substituted or unsubstituted aryl having 6 to 20 carbon atoms, substituted or unsubstituted heteroaryl having 3 to 20 carbon atoms, substituted or unsubstituted alkylsilyl having 3 to 20 carbon atoms, substituted or unsubstituted arylsilyl having 6 to 20 carbon atoms and combinations thereof.

According to an embodiment of the present disclosure, wherein in Formula 3-6 to Formula 3-13, $X_{12}$ and/or $X_{14}$ are/is selected from $CR_{x1}$, $X_{22}$ and/or $X_{24}$ are/is selected from $CR_{x2}$, $X_{32}$ and/or $X_{34}$ are/is selected from $CR_{x3}$, $X_{42}$ and/or $X_{44}$ are/is selected from $CR_{x4}$, $X_{52}$ and/or $X_{54}$ are/is selected from $CR_{x5}$, and the $R_{x1}$, $R_{x2}$, $R_{x3}$, $R_{x4}$ and $R_{x5}$ are, at each occurrence identically or differently, selected from the group consisting of: substituted or unsubstituted alkyl having 1 to 10 carbon atoms, substituted or unsubstituted cycloalkyl having 3 to 10 ring carbon atoms and combinations thereof.

According to an embodiment of the present disclosure, wherein in Formula 3-6 to Formula 3-13, Xie and $X_{14}$ are each independently selected from $CR_{x1}$, $X_{22}$ and $X_{24}$ are each independently selected from $CR_{x2}$, $X_{32}$ and $X_{34}$ are each independently selected from $CR_{x3}$, $X_{42}$ and $X_{44}$ are each independently selected from $CR_{x4}$, $X_{52}$ and $X_{54}$ are each independently selected from $CR_{x5}$, and the $R_{x1}$, $R_{x2}$, $R_{x3}$, $R_{x4}$ and $R_{x5}$ are, at each occurrence identically or differently, selected from the group consisting of: deuterium, methyl, ethyl, propyl, isopropyl, n-butyl, isobutyl, t-butyl, cyclopentyl, cyclohexyl, deuterated methyl, deuterated ethyl, deuterated propyl, deuterated isopropyl, deuterated n-butyl, deuterated isobutyl, deuterated t-butyl, deuterated cyclopentyl, deuterated cyclohexyl and combinations thereof.

According to an embodiment of the present disclosure, wherein in the second compound, the $L_a$ is, at each occurrence identically or differently, selected from the group consisting of $L_{a-1}$ to $L_{a-387}$, wherein the specific structures of $L_{a-1}$ to $L_{a-387}$ are referred to claim 22.

According to an embodiment of the present disclosure, wherein in the second compound, the $L_b$ has a structure represented by Formula 4:

Formula 4

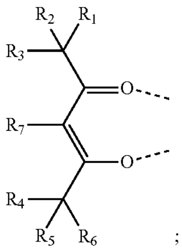

;

$R_1$ to $R_7$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof According to an embodiment of the present disclosure, wherein in the second compound, the $L_b$ has the structure represented by Formula 4, wherein at least one or two of $R_1$ to $R_3$ are, at each occurrence identically or differently, selected from substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms or a combination thereof and/or at least one or two of $R_4$ to $R_6$ are selected from substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms or a combination thereof.

According to an embodiment of the present disclosure, wherein in the second compound, the $L_b$ has the structure represented by Formula 4, wherein at least two of $R_1$ to $R_3$ are, at each occurrence identically or differently, selected from substituted or unsubstituted alkyl having 2 to 20 carbon atoms, substituted or unsubstituted cycloalkyl having 3 to 20 ring carbon atoms, substituted or unsubstituted heteroalkyl having 2 to 20 carbon atoms or a combination thereof; and/or at least two of $R_4$ to $R_6$ are, at each occurrence identically or differently, selected from substituted or unsubstituted alkyl having 2 to 20 carbon atoms, substituted or unsubstituted cycloalkyl having 3 to 20 ring carbon atoms, substituted or unsubstituted heteroalkyl having 2 to 20 carbon atoms or a combination thereof.

According to an embodiment of the present disclosure, wherein in the second compound, the $L_b$ is, at each occurrence identically or differently, selected from the group consisting of $L_{b1}$ to $L_{b322}$, wherein the specific structures of $L_{b1}$ to $L_{b322}$ are referred to claim 24.

According to an embodiment of the present disclosure, wherein the second compound has a structure of $Ir(L_a)_2(L_b)$, wherein $L_a$ is, at each occurrence identically or differently, selected from any one or any two of the group consisting of $L_{a-1}$ to $L_{a-387}$, and $L_b$ is selected from any one of the group consisting of $L_{b1}$ to $L_{b322}$.

According to an embodiment of the present disclosure, wherein the second compound is selected from the group consisting of Compound 2-1 to Compound 2-34, Compound 2-39 to Compound 2-70, Compound 2-75 to Compound 2-106, Compound 2-111 to Compound 2-142, Compound 2-147 to Compound 2-178, Compound 2-183 to Compound 2-214, Compound 2-217 to Compound 2-227, Compound 2-229 to Compound 2-241, Compound 2-243 to Compound 2-255, Compound 2-257 to Compound 2-269, Compound 2-271 to Compound 2-283, Compound 2-285 to Compound 2-297 and Compound 2-299 to Compound 2-300, wherein the specific structures of Compound 2-1 to Compound 2-34, Compound 2-39 to Compound 2-70, Compound 2-75 to Compound 2-106, Compound 2-111 to Compound 2-142, Compound 2-147 to Compound 2-178, Compound 2-183 to Compound 2-214, Compound 2-217 to Compound 2-227, Compound 2-229 to Compound 2-241, Compound 2-243 to Compound 2-255, Compound 2-257 to Compound 2-269, Compound 2-271 to Compound 2-283, Compound 2-285 to Compound 2-297 and Compound 2-299 to Compound 2-300 are referred to claim 25.

According to an embodiment of the present disclosure, wherein the organic layer is a light-emitting layer, the first compound is a host material, and the second compound is a light-emitting material.

According to an embodiment of the present disclosure, wherein the electroluminescent device emits red light.

According to an embodiment of the present disclosure, wherein the electroluminescent device emits white light.

According to another embodiment of the present disclosure, further disclosed is a display assembly comprising an electroluminescent device. The specific structure of the electroluminescent device is as shown in any one of the embodiments described above.

According to another embodiment of the present disclosure, further disclosed is a compound combination comprising a first compound and a second compound;

the first compound has a structure of H-L-E;

H has a structure represented by Formula 1:

Formula 1

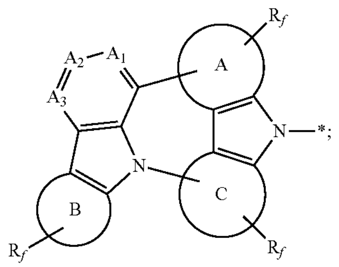

in Formula 1, $A_1$, $A_2$ and $A_3$ are, at each occurrence identically or differently, selected from N or CR, and the ring A, the ring B and the ring C are, at each occurrence identically or differently, selected from a carbocyclic ring having 5 to 18 carbon atoms or a heterocyclic ring having 3 to 18 carbon atoms;

$R_f$ represents, at each occurrence identically or differently, mono-substitution, multiple substitutions or non-substitution;

E has a structure represented by Formula 2:

Formula 2

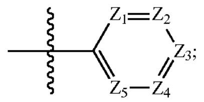

in Formula 2, at least one of $Z_1$ to $Z_5$ is N, and the rest of $Z_1$ to $Z_5$ are each independently selected from $CR_z$;

L is selected from a single bond, substituted or unsubstituted arylene having 6 to 30 carbon atoms, substituted or unsubstituted heteroarylene having 3 to 30 carbon atoms or a combination thereof;

R, $R_f$ and $R_z$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;

adjacent substituents R, $R_f$ can be optionally joined to form a ring;

the second compound is a metal complex having a general formula of $M(L_a)_m(L_b)_n(L_c)_q$;

wherein the M is selected from a metal with a relative atomic mass greater than 40;

$L_a$, $L_b$ and $L_c$ are a first ligand, a second ligand and a third ligand coordinated to the M, respectively; $L_a$, $L_b$ and $L_c$ can be optionally joined to form a multidentate ligand;

$L_a$, $L_b$ and $L_c$ may be the same or different; m is 1, 2 or 3, n is 0, 1 or 2, q is 0 or 1, and m+n+q equals to the oxidation state of the M; when m is greater than or equal to 2, the multiple $L_a$ may be the same or different; when n is equal to 2, the two $L_b$ may be the same or different;

$L_a$ has a structure represented by Formula 3:

Formula 3

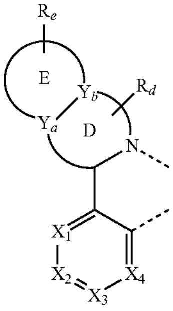

;

wherein, the ring D is selected from a five-membered heteroaromatic ring or a six-membered heteroaromatic ring;

the ring E is selected from a five-membered unsaturated carbocyclic ring, a benzene ring, a five-membered heteroaromatic ring or a six-membered heteroaromatic ring;

the ring D and the ring E are fused via $Y_a$ and $Y_b$;

$Y_a$ and $Y_b$ are, at each occurrence identically or differently, selected from C or N;

$R_d$ and $R_e$ represent, at each occurrence identically or differently, mono-substitution, multiple substitutions or non-substitution;

$X_1$ to $X_4$ are, at each occurrence identically or differently, selected from $CR_x$ or N;

$R_d$, $R_e$ and $R_x$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;

adjacent substituents $R_d$, $R_e$, $R_x$ can be optionally joined to form a ring;

$L_b$ and $L_c$ are each independently selected from any one of the following structures:

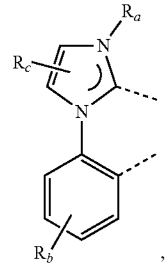
,
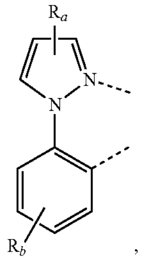
,
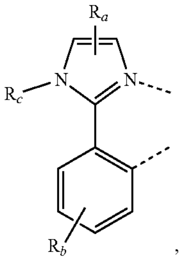
,
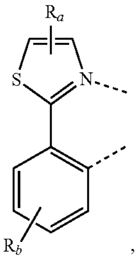
,
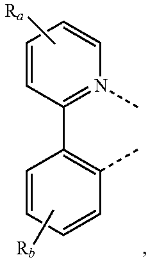
,
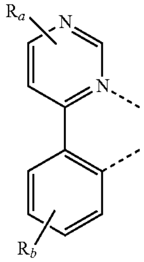
,
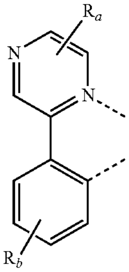
,
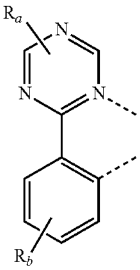
,
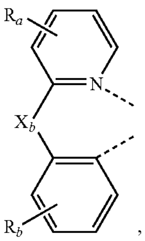
,
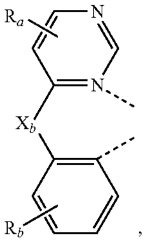
,
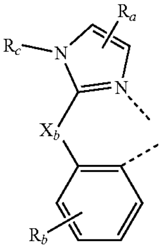
,
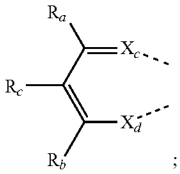
;

$R_a$, $R_b$ and $R_c$ represent, at each occurrence identically or differently, mono-substitution, multiple substitutions or non-substitution;

$X_b$ is selected from the group consisting of: O, S, Se, $NR_{N1}$ and $CR_{C1}R_{C2}$;

$X_c$ and $X_d$ are each independently selected from the group consisting of: O, S, Se and $NR_{N2}$;

$R_a$, $R_b$, $R_c$, $R_{N1}$, $R_{N2}$, $R_{C1}$ and $R_{C2}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;

in structures of $L_b$ and $L_c$, adjacent substituents $R_a$, $R_b$, $R_c$, $R_{N1}$, $R_{N2}$, $R_{C1}$ and $R_{C2}$ can be optionally joined to form a ring;

and, the following case is not comprised: the first compound is

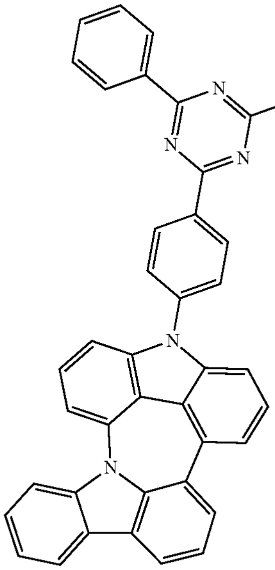

while the second compound is

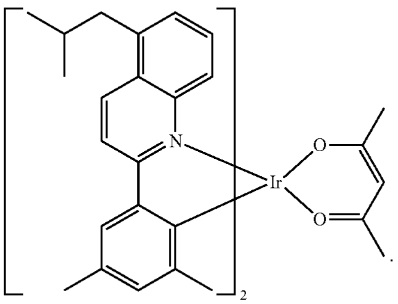

Combination with Other Materials

The materials described in the present disclosure for a particular layer in an organic light emitting device can be used in combination with various other materials present in the device. The combinations of these materials are described in more detail in U.S. Pat. App. No. 20160359122 at paragraphs 0132-0161, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

The materials described herein as useful for a particular layer in an organic light emitting device may be used in combination with a variety of other materials present in the device. For example, compounds disclosed herein may be used in combination with a wide variety of hosts, transport layers, blocking layers, injection layers, electrodes and other layers that may be present. The combination of these materials is described in detail in paragraphs 0080-0101 of U.S. Pat. App. No. 20150349273, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

In the embodiments of material synthesis, all reactions were performed under nitrogen protection unless otherwise stated. All reaction solvents were anhydrous and used as received from commercial sources. Synthetic products were structurally confirmed and tested for properties using one or more conventional equipment in the art (including, but not limited to, nuclear magnetic resonance instrument produced by BRUKER, liquid chromatograph produced by SHIMADZU, liquid chromatograph-mass spectrometry produced by SHIMADZU, gas chromatograph-mass spectrometry produced by SHIMADZU, differential Scanning calorimeters produced by SHIMADZU, fluorescence spectrophotometer produced by SHANGHAI LENGGUANG TECH., electrochemical workstation produced by WUHAN CORRTEST, and sublimation apparatus produced by ANHUI BEQ, etc.) by methods well known to the persons skilled in the art. In the embodiments of the device, the characteristics of the device were also tested using conventional equipment in the art (including, but not limited to, evaporator produced by ANGSTROM ENGINEERING, optical testing system produced by SUZHOU FATAR, life testing system produced by SUZHOU FATAR, and ellipsometer produced by BEIJING ELLITOP, etc.) by methods well known to the persons skilled in the art. As the persons skilled in the art are aware of the above-mentioned equipment use, test methods and other related contents, the inherent data of the sample can be obtained with certainty and without influence, so the above related contents are not further described in this present disclosure.

Material Synthesis

Methods selected in the present disclosure for preparing a first compound and a second compound are not limited herein. Typically, the following compounds are taken as examples without limitations, and synthesis routes and preparation methods thereof are described below.

Synthesis Example 1: Synthesis of Compound 1-1

Step 1: Synthesis of Intermediate 1

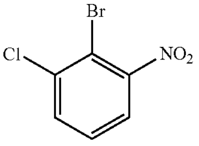

+

-continued

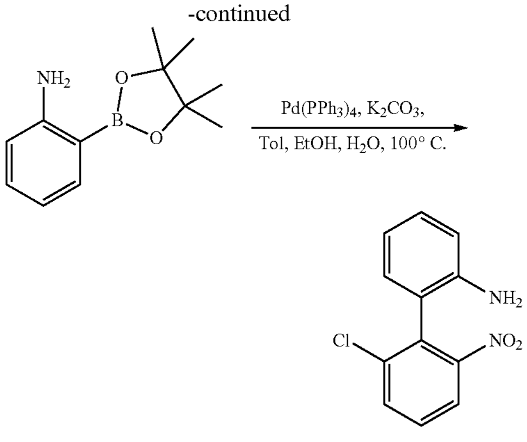

1

Under nitrogen protection, 2-bromo-3-chloronitrobenzene (100 g, 425.5 mmol), 2-aminophenylboronic acid pinacol ester (102 g, 468.1 mmol), tetrakis(triphenylphosphine) palladium (4.9 g, 4.25 mmol), potassium carbonate (115 g, 852 mmol), toluene (1000 mL), water (200 mL) and ethanol (200 mL) were added to a three-necked flask and reacted at 100° C. for 48 h. After the reaction was complete, the reaction solution was cooled to room temperature, concentrated to remove solvents, and added with distilled water. The mixture was extracted with ethyl acetate. The organic phases were washed with water, dried over anhydrous magnesium sulfate, concentrated to remove the solvent, and purified through column chromatography (PE/EA=4:1) to obtain Intermediate 1 as a yellow oil (90 g, yield: 85%).

Step 2: Synthesis of Intermediate 2

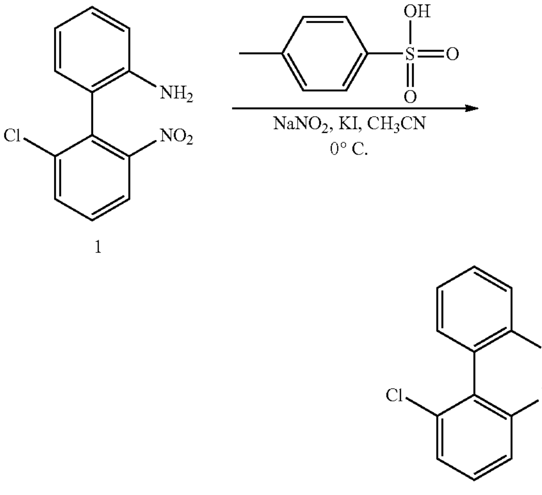

2

Intermediate 1 (90 g, 363 mmol) and acetonitrile (1000 mL) were put into a three-necked flask, respectively. p-Toluenesulfonic acid (193.2 g, 1088 mmol) was added portionwise at 0° C. and stirred for 30 min. At this temperature, an aqueous solution of a mixture of sodium nitrite (69 g, 726 mmol) and potassium iodide (150.6 g, 907 mmol) was slowly added dropwise. After the dropwise addition was complete, the mixture was slowly warmed to room temperature and reacted for 12 h. After the reaction was complete, a saturated aqueous solution of sodium thiosulfate was added dropwise to quench the reaction. The reaction solution was concentrated and diluted with water. The mixed solution was extracted three times with ethyl acetate. The organic phases were dried over anhydrous sodium sulfate and concentrated to remove solvents. The mixture was isolated through column chromatography (PE/DCM=10/1) to obtain Intermediate 2 as a yellow solid (85 g, yield: 65%).

Step 3: Synthesis of Intermediate 4

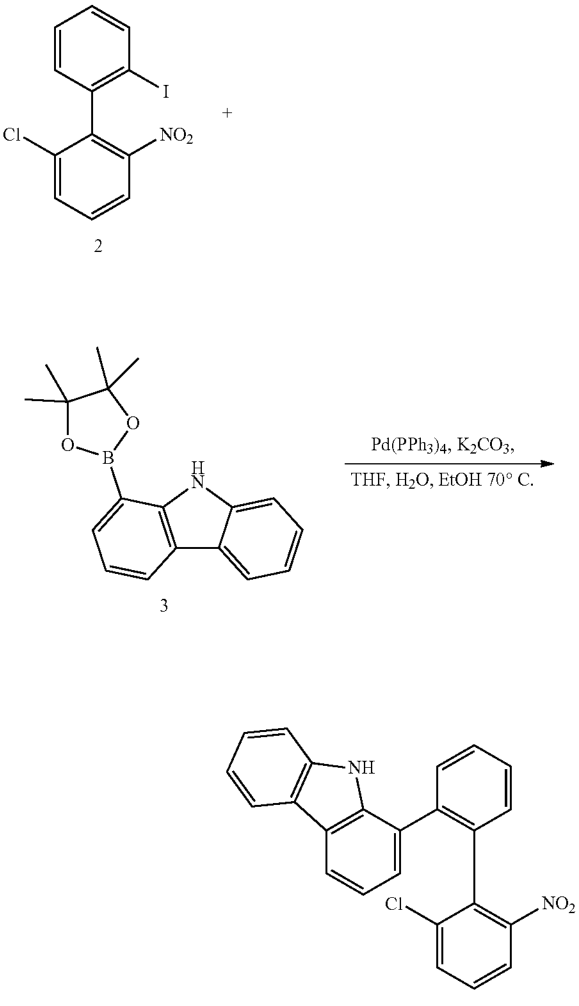

2 3 4

Under nitrogen protection, Intermediate 2 (20 g, 55.7 mmol), Intermediate 3 (24.5 g, 83.6 mmol), tetrakis(triphenylphosphine)palladium (1.9 g, 1.67 mmol), potassium carbonate (15.4 g, 111.4 mmol), tetrahydrofuran (500 mL), water (100 mL) and ethanol (100 mL) were added to a three-necked flask and reacted at 70° C. for 48 h. After the reaction was complete, the reaction solution was cooled to room temperature, concentrated to remove solvents, and added with distilled water. The mixture was extracted with ethyl acetate. The organic phases were washed with water, dried over anhydrous magnesium sulfate, concentrated to remove the solvent, and purified through column chromatography (PE/EA=4:1) to obtain Intermediate 4 as a yellow solid (12 g, yield: 55%).

Step 4: Synthesis of Intermediate 5

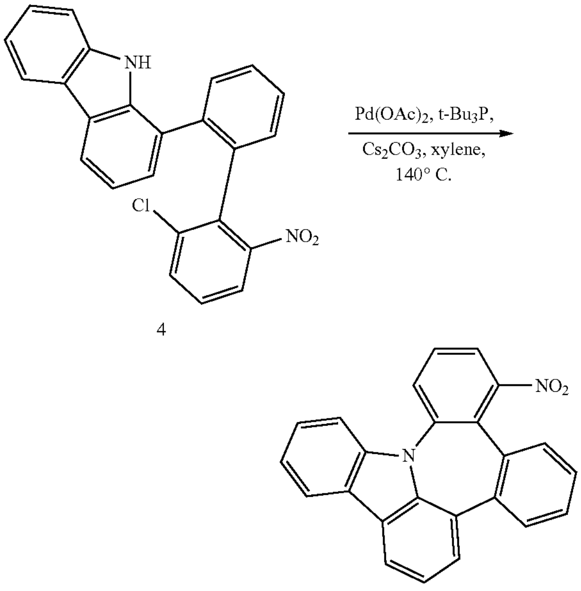

4

5

Under nitrogen protection, Intermediate 4 (12 g, 30.15 mmol), palladium acetate (338 mg, 1.5 mmol), tri-tert-butylphosphine (606 mg, 3.0 mmol), cesium carbonate (20 g, 60.3 mmol) and xylene (230 mL) were added to a three-necked flask and reacted at 140° C. for 10 h. After the reaction was complete, the reaction solution was cooled to room temperature, concentrated to remove solvents, and added with distilled water. The mixture was extracted with ethyl acetate. The organic phases were washed with water, dried over anhydrous magnesium sulfate, concentrated to remove the solvent, and purified through column chromatography (PE/EA=6:1) to obtain Intermediate 5 as a yellow solid (9 g, yield: 80%).

Step 5: Synthesis of Intermediate 6

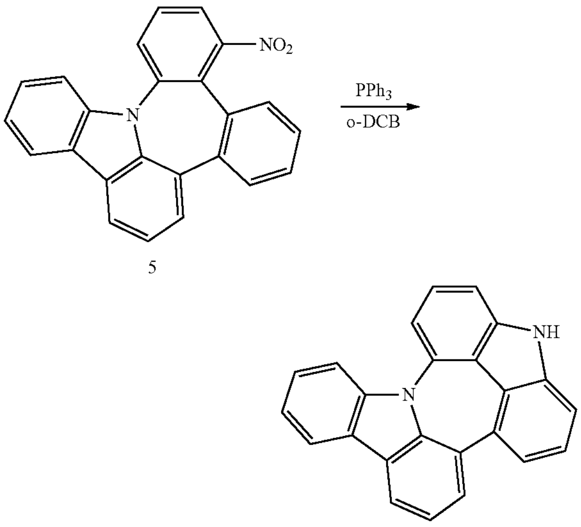

5

6

Under nitrogen protection, Intermediate 5 (9 g, 24.9 mmol), triphenylphosphine (19.6 g, 74.7 mmol) and o-dichlorobenzene (o-DCB) (100 mL) were added to a three-necked flask and reacted at 200° C. for 12 h. After the reaction was complete, the reaction solution was concentrated to remove the solvent, and the crude product was isolated through column chromatography to obtain Intermediate 6 as a yellow solid (7 g, yield: 85%). $^1$H NMR (400 MHz, DMSO-$d_6$) δ 11.41 (s, 1H), 8.20 (d, J=7.7 Hz, 1H), 8.14 (d, J=8.4 Hz, 1H), 8.03 (d, J=7.5 Hz, 1H), 7.91 (d, J=7.8 Hz, 1H), 7.58-7.46 (m, 2H), 7.41 (d, J=7.9 Hz, 1H), 7.39-7.31 (m, 4H), 7.28 (t, J=7.7 Hz, 1H), 7.15 (d, J=7.7 Hz, 1H).

Step 6: Synthesis of Compound 1-1

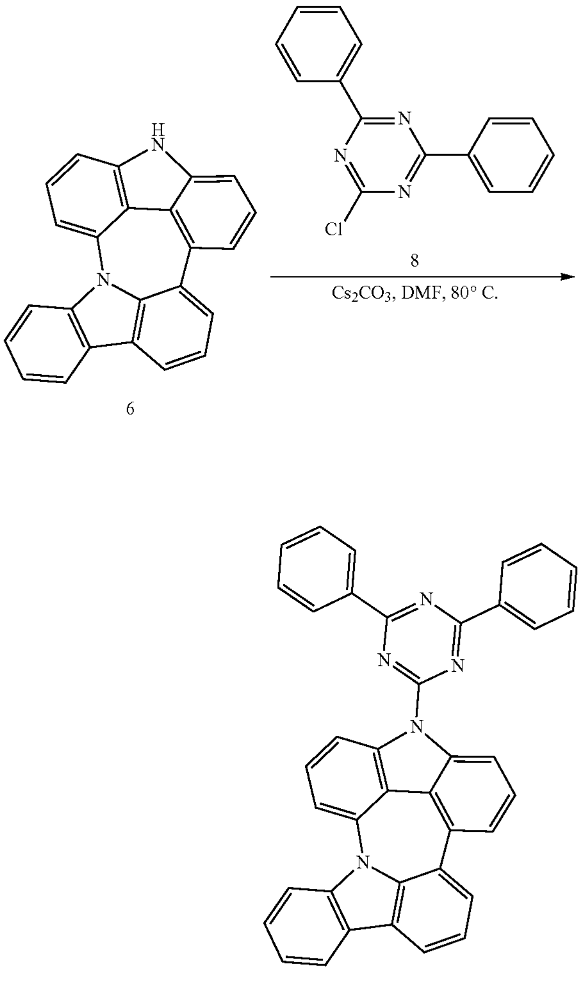

8

6

1-1

Under nitrogen protection, Intermediate 6 (2 g, 6.06 mmol), Intermediate 8 (1.8 g, 6.6 mmol), cesium carbonate (3.9 g, 12.12 mmol) and DMF (60 mL) were added to a three-necked flask and reacted at 80° C. for 5 h. After the reaction was complete, the reaction solution was cooled to room temperature, added with distilled water and filtered to obtain a solid. The crude product was washed three times (with THF/Tol=1:1) to obtain Compound 1-1 as a yellow solid (2.4 g, yield: 72%). The structure of the compound was confirmed as the target product with a molecular weight of 561.2.

Synthesis Example 2: Synthesis of Compound 1-2

Step 1: Synthesis of Compound 1-2

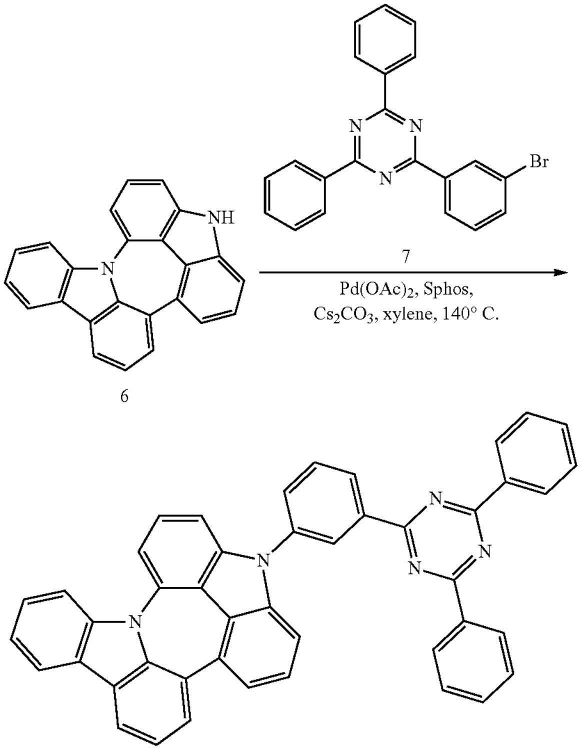

6

7

1-2

Under nitrogen protection, Intermediate 6 (3 g, 9.1 mmol), Intermediate 7 (3.87 g, 10 mmol), palladium acetate (40 mg, 0.02 mmol), 2-bicyclohexylphosphine-2',6'-dimethoxybiphenyl (147 mg, 0.04 mmol), cesium carbonate (5.9 g, 18.2 mmol) and xylene (100 ml) were added to a three-necked flask and reacted at 140° C. for 10 h. After the reaction was complete, the reaction solution was cooled to room temperature, concentrated to remove solvents, and added with distilled water. The mixture was extracted with ethyl acetate. The organic phases were washed with water and concentrated to remove the solvent. The crude product was washed with toluene, tetrahydrofuran and acetone to obtain Compound 1-2 as a yellow solid (3 g, yield: 51%). The structure of the compound was confirmed as the target product with a molecular weight of 637.2.

Those skilled in the art will appreciate that the above preparation methods are merely exemplary. Those skilled in the art can obtain other structures of the first compound and the second compound selected by the present disclosure through the modifications of the preparation methods. Alternatively, the other structures of the first compound and the second compound can be obtained with reference to Chinese Patent Application Nos. CN2020102702502 and CN2020102850167, which is not repeated herein.

The method for preparing an electroluminescent device is not limited. The preparation method in the following example is merely an example and not to be construed as a limitation. Those skilled in the art can make reasonable improvements on the preparation method in the following example based on the related art. Exemplarily, the proportions of various materials in a light-emitting layer are not particularly limited. Those skilled in the art can reasonably select the proportions within a certain range based on the related art. For example, based on the total weight of the materials in the light-emitting layer, the first compound accounts for 80%-99% and the second compound accounts for 1%-20%; or, preferably, the second compound accounts for 1%-10%.

Device Example 1

First, a glass substrate having an Indium Tin Oxide (ITO) anode with a thickness of 120 nm was cleaned and then treated with oxygen plasma and UV ozone. After the treatment, the substrate was dried in a nitrogen-filled glovebox to remove moisture and then mounted on a substrate holder and placed in a vacuum chamber. Organic layers specified below were sequentially deposited through vacuum thermal evaporation on the ITO anode at a rate of 0.01 to 5 Å/s and at a vacuum degree of about $10^{-8}$ torr. Compound HI was used as a hole injection layer (HIL) with a thickness of 100 Å. Compound HT was used as a hole transporting layer (HTL) with a thickness of 400 Å. Compound EB was used as an electron blocking layer (EBL) with a thickness of 50 Å. Then, Compound 1-1 as a host and Compound 2-2 as a dopant were co-deposited as an emissive layer (EML) with a thickness of 400 Å. Compound HB was used as a hole blocking layer (HBL) with a thickness of 50 Å. On the HBL, Compound ET and 8-hydroxyquinolinolato-lithium (Liq) were co-deposited as an electron transporting layer (ETL) with a thickness of 350 Å. Finally, 8-hydroxyquinolinolato-lithium (Liq) with a thickness of 10 Å was deposited as an electron injection layer (EIL), and Al with a thickness of 1200 Å was deposited as a cathode. The device was transferred back to the glovebox and encapsulated with a glass lid to complete the device.

Device Example 2

The implementation mode in Device Example 2 was the same as that in Device Example 1, except that Compound 1-1 was replaced with Compound 1-2 as the host in the emissive layer (EML).

Device Example 3

The implementation mode in Device Example 3 was the same as that in Device Example 1, except that Compound 2-2 was replaced with Compound 2-125 as the dopant in the emissive layer (EML).

Device Example 4

The implementation mode in Device Example 4 was the same as that in Device Example 2, except that Compound 2-2 was replaced with Compound 2-125 as the dopant in the emissive layer (EML).

Device Example 5

The implementation mode in Device Example 5 was the same as that in Device Example 2, except that Compound 2-2 was replaced with Compound 2-43 as the dopant in the emissive layer (EML).

Device Example 6

The implementation mode in Device Example 6 was the same as that in Device Example 2, except that Compound 2-2 was replaced with Compound 2-1 as the dopant in the emissive layer (EML).

Device Comparative Example 1

The implementation mode in Device Comparative Example 1 was the same as that in Device Example 1, except that Compound 2-2 was replaced with Compound RD-A as the dopant in the emissive layer (EML).

Device Comparative Example 2

The implementation mode in Device Comparative Example 2 was the same as that in Device Example 2, except that Compound 2-2 was replaced with Compound RD-A as the dopant in the emissive layer (EML).

Device Comparative Example 3

The implementation mode in Device Comparative Example 3 was the same as that in Device Example 1, except that Compound 1-1 was replaced with Compound CBP as the host in the emissive layer (EML).

Device Comparative Example 4

The implementation mode in Device Comparative Example 4 was the same as that in Device Comparative Example 3, except that Compound 2-2 was replaced with Compound RD-A as the dopant in the emissive layer (EML).

Device Comparative Example 5

The implementation mode in Device Comparative Example 5 was the same as that in Device Comparative Example 3, except that Compound 2-2 was replaced with Compound 2-43 as the dopant in the emissive layer (EML).

Device Comparative Example 6

The implementation mode in Device Comparative Example 6 was the same as that in Device Comparative Example 3, except that Compound 2-2 was replaced with Compound 2-1 as the dopant in the emissive layer (EML).

Device Comparative Example 8

The implementation mode in Device Comparative Example 8 was the same as that in Device Example 5, except that Compound 1-2 was replaced with Compound A as the host in the emissive layer (EML).

The structures and thicknesses of layers of the devices are shown in the following table. A layer using more than one material is obtained by doping different compounds at their weight ratios as recorded.

TABLE 1

Device structures in device examples and device comparative examples

| | | | | EML (400 Å) | | | |
|---|---|---|---|---|---|---|---|
| Device ID | HIL | HTL | EBL | Host | Dopant | HBL | ETL |
| Example 1 | Compound HI (100 Å) | Compound HT (400 Å) | Compound EB (50 Å) | Compound 1-1 (98%) | Compound 2-2 (2%) | Compound HB (50 Å) | Compound ET: Liq (40: 60) (350 Å) |
| Example 2 | Compound HI (100 Å) | Compound HT (400 Å) | Compound EB (50 Å) | Compound 1-2 (98%) | Compound 2-2 (2%) | Compound HB (50 Å) | Compound ET: Liq (40: 60) (350 Å) |
| Example 3 | Compound HI (100 Å) | Compound HT (400 Å) | Compound EB (50 Å) | Compound 1-1 (98%) | Compound 2-125 (2%) | Compound HB (50 Å) | Compound ET: Liq (40: 60) (350 Å) |
| Example 4 | Compound HI (100 Å) | Compound HT (400 Å) | Compound EB (50 Å) | Compound 1-2 (98%) | Compound 2-125 (2%) | Compound HB (50 Å) | Compound ET: Liq (40: 60) (350 Å) |
| Example 5 | Compound HI (100 Å) | Compound HT (400 Å) | Compound EB (50 Å) | Compound 1-2 (98%) | Compound 2-43 (2%) | Compound HB (50 Å) | Compound ET: Liq (40: 60) (350 Å) |
| Example 6 | Compound HI (100 Å) | Compound HT (400 Å) | Compound EB (50 Å) | Compound 1-2 (98%) | Compound 2-1 (2%) | Compound HB (50 Å) | Compound ET: Liq (40: 60) (350 Å) |
| Comparative Example 1 | Compound HI (100 Å) | Compound HT (400 Å) | Compound EB (50 Å) | Compound 1-1 (98%) | Compound RD-A (2%) | Compound HB (50 Å) | Compound ET: Liq (40: 60) (350 Å) |
| Comparative Example 2 | Compound HI (100 Å) | Compound HT (400 Å) | Compound EB (50 Å) | Compound 1-2 (98%) | Compound RD-A (2%) | Compound HB (50 Å) | Compound ET: Liq (40: 60) (350 Å) |
| Comparative Example 3 | Compound HI (100 Å) | Compound HT (400 Å) | Compound EB (50 Å) | Compound CBP (98%) | Compound 2-2 (2%) | Compound HB (50 Å) | Compound ET: Liq (40: 60) (350 Å) |

TABLE 1-continued

Device structures in device examples and device comparative examples

| | | | | EML (400 Å) | | | |
|---|---|---|---|---|---|---|---|
| Device ID | HIL | HTL | EBL | Host | Dopant | HBL | ETL |
| Comparative Example 4 | Compound HI (100 Å) | Compound HT (400 Å) | Compound EB (50 Å) | Compound CBP (98%) | Compound RD-A (2%) | Compound HB (50 Å) | Compound ET: Liq (40: 60) (350 Å) |
| Comparative Example 5 | Compound HI (100 Å) | Compound HT (400 Å) | Compound EB (50 Å) | Compound CBP (98%) | Compound 2-43 (2%) | Compound HB (50 Å) | Compound ET: Liq (40: 60) (350 Å) |
| Comparative Example 6 | Compound HI (100 Å) | Compound HT (400 Å) | Compound EB (50 Å) | Compound CBP (98%) | Compound 2-1 (2%) | Compound HB (50 Å) | Compound ET: Liq (40: 60) (350 Å) |
| Comparative Example 8 | Compound HI (100 Å) | Compound HT (400 Å) | Compound EB (50 Å) | Compound A (98%) | Compound 2-43 (2%) | Compound HB (50 Å) | Compound ET: Liq (40: 60) (350 Å) |

The structures of the materials used in the devices are shown as follows:

Compound HI

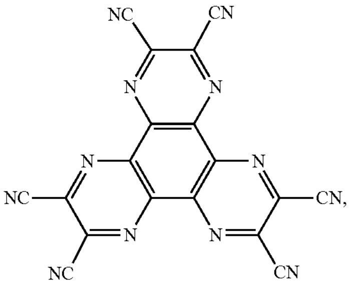

,

Compound HT

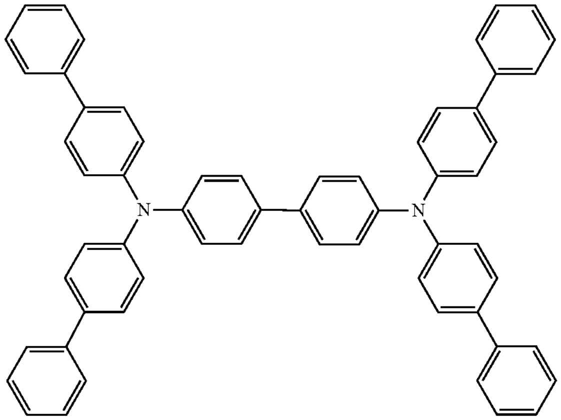

,

-continued

Compound EB

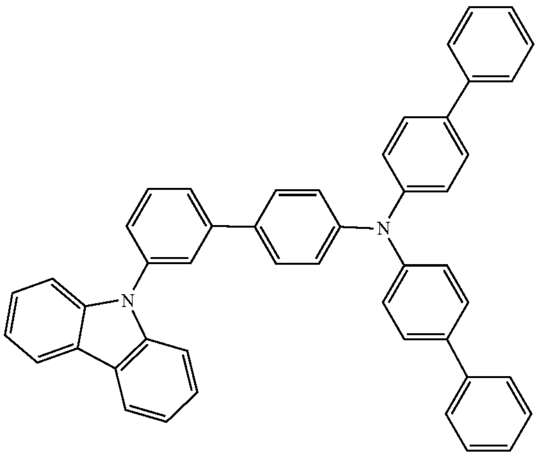

,

Compound 2-125

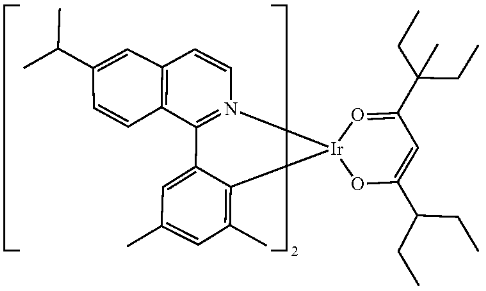

,

-continued
Compound 2-2
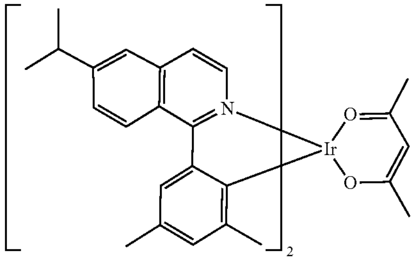
,
Compound 2-43
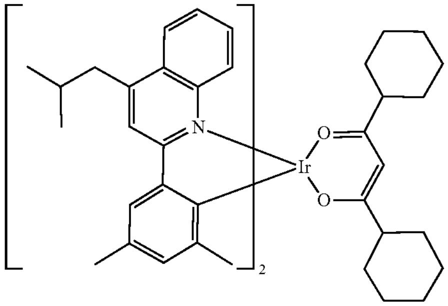
,
Compound 2-1
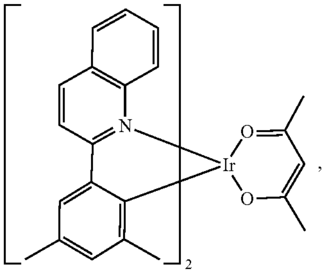
,
Compound RD-A
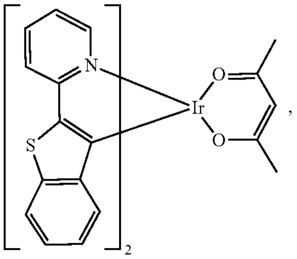
,
Compound HB
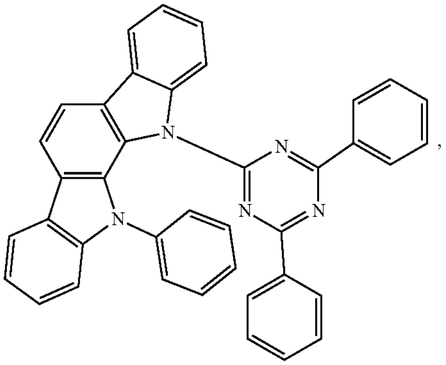
,
-continued
Compound ET
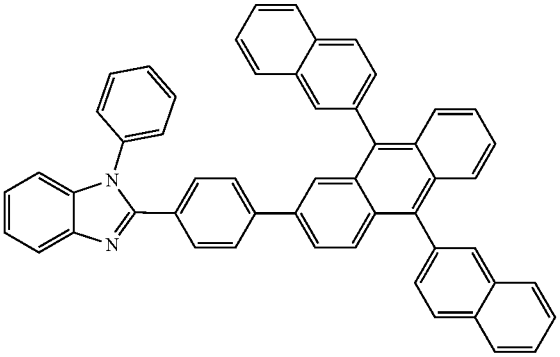
,
Liq
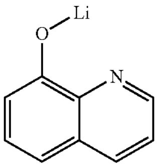
,
Compound A
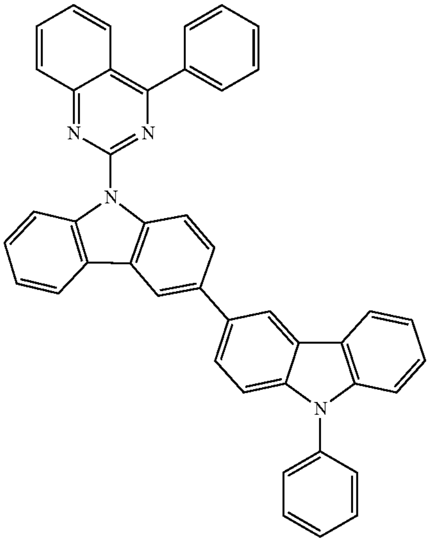
,
1-1
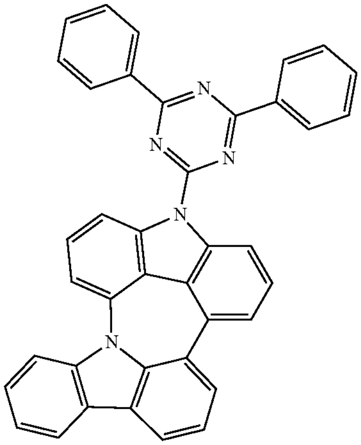
, -continued 1-2

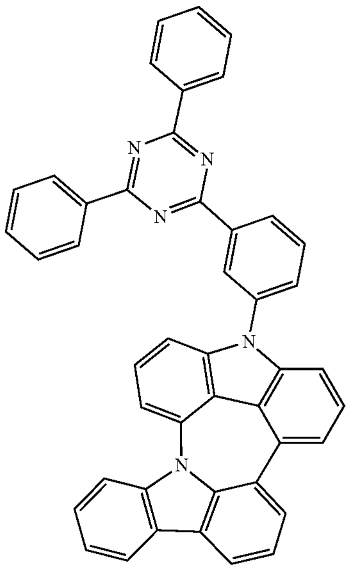

,

CBP

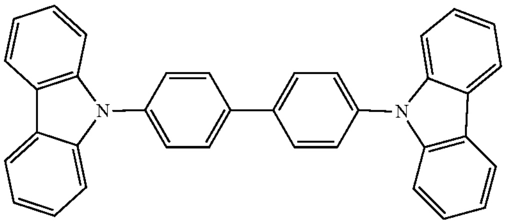

.

The voltage (V), power efficiency (PE) and lifetime (LT97) of Device Examples 1-6 and Device Comparative Examples 1-6 and 8, which were measured at 15 $mA/cm^2$, are listed in Table 2.

TABLE 2

| Device data | | | |
|---|---|---|---|
| | At 15 $mA/cm^2$ | | |
| Device ID | Voltage [V] | PE [lm/W] | LT97 [hrs] |
| Example 1 | 3.5 | 14 | 169 |
| Example 2 | 3.4 | 17 | 1524 |
| Example 3 | 3.6 | 16 | 499.4 |
| Example 4 | 3.6 | 18 | 2069 |
| Example 5 | 3.6 | 29 | 874 |
| Example 6 | 3.5 | 18 | 1222.2 |
| Comparative Example 1 | 3.5 | 4 | 4 |
| Comparative Example 2 | 3.6 | 6 | 13 |
| Comparative Example 3 | 8.6 | 4 | 7 |
| Comparative Example 4 | 8.3 | 1 | 4 |
| Comparative Example 5 | 8.2 | 8 | 6.4 |
| Comparative Example 6 | 9.1 | 5 | 6.4 |
| Comparative Example 8 | 4.4 | 27 | 854 |

DISCUSSION

As shown in Table 2, the device comparative examples in the present disclosure were set with reference to device experiments disclosed in the related art (such as KR1020150077220A), using a host material (such as Compound CBP) commonly used in the related art (such as KR1020150077220A), and a current commercial host material, Compound A, and a phosphorescent light-emitting material (such as Compound RD-A) commonly used in the related art (such as KR1020150077220A) as comparative compounds.

It can be seen from the device data that Example 1 which uses a combination of the present disclosure (first compound 1-1 and second compound 2-2) as the emissive layer has the same voltage as Comparative Example 1 (which uses first compound 1-1 and RD-A as the emissive layer), but the power efficiency of Example 1 is 10 lm/W (2.5 times) higher than that of Comparative Example 1 and the lifetime of Example 1 is 165 hours (41.3 times) longer than that of Comparative Example 1, which are unexpectedly improved. Similarly, it can be seen that Example 2 which uses a combination of the present disclosure (first compound 1-2 and second compound 2-2) as the emissive layer has a driving voltage (3.4 V) that is 0.2 V lower than that (3.6 V) of Comparative Example 2 (which uses first compound 1-2 and RD-A as the emissive layer), and the power efficiency of Example 2 is 11 lm/W (2.0 times) higher than that of Comparative Example 2 and the lifetime of Example 2 is 1511 hours (116 times) longer than that of Comparative Example 2, which are surprisingly improved. In particular, the lifetime has been improved more than 100 times.

Example 3 which uses a combination of the present disclosure (first compound 1-1 and second compound 2-125) as the emissive layer has substantially the same voltage as Comparative Example 1 (which uses first compound 1-1 and RD-A as the emissive layer), but the power efficiency of Example 3 is 12 lm/W (3.0 times) higher than that of Comparative Example 1 and the lifetime of Example 3 is 495.4 hours (123.9 times) longer than that of Comparative Example 1, which are also surprisingly improved.

Example 4 which uses a combination of the present disclosure (first compound 1-2 and second compound 2-125) as the emissive layer has the same voltage as Comparative Example 2 (which uses first compound 1-2 and RD-A as the emissive layer), but the power efficiency of Example 4 is 12 lm/W (2.0 times) higher than that of Comparative Example 2 and the lifetime of Example 4 is 2056 hours (158.2 times) longer than that of Comparative Example 2, which are unexpectedly improved. In particular, the lifetime has been further improved and reaches 2069 hours.

These results show that the combination of the first compound and the second compound of the present disclosure can greatly improve device performance (driving voltage, power efficiency and lifetime), which far exceeds the device effects when the first compound selected by the present disclosure is used in combination with the phosphorescent light-emitting material that is used as the dopant in the related art. This indicates the superiority of the combination of the first compound and the second compound of the present disclosure. In particular, this also fully proves the unexpected effects due to the use of the first compound selected by the present disclosure as a red phosphorescent host material in combination with the second compound with a particular structure.

Example 1 which uses the combination of the present disclosure (first compound 1-1 and second compound 2-2)

as the emissive layer has a driving voltage (3.5 V) that is 5.1 V lower than that (8.6 V) of Comparative Example 3 (which uses CBP and second compound 2-2 as the emissive layer), and the power efficiency of Example 1 is 10 lm/W (2.5 times) higher than that of Comparative Example 3 and the lifetime of Example 1 is 162 hours (23.1 times) longer than that of Comparative Example 3, which are significantly improved.

Example 2 which uses the combination of the present disclosure (first compound 1-2 and second compound 2-2) as the emissive layer has a driving voltage (3.4 V) that is 5.2 V lower than that (8.6 V) of Comparative Example 3 (which uses CBP and second compound 2-2 as the emissive layer), and the power efficiency of Example 2 is 13 lm/W (3.3 times) higher than that of Comparative Example 3 and the lifetime of Example 2 is 1517 hours (216.7 times) longer than that of Comparative Example 3, which are significantly improved.

Example 5 which uses a combination of the present disclosure (first compound 1-2 and second compound 2-43) as the emissive layer has a driving voltage (3.6 V) that is 4.6 V lower than that (8.2 V) of Comparative Example 5 (which uses CBP and second compound 2-43 as the emissive layer), and the power efficiency of Example 5 is 21 lm/W (2.6 times) higher than that of Comparative Example 5 and the lifetime of Example 5 is 867.6 hours (135.6 times) longer than that of Comparative Example 5.

Example 6 which uses a combination of the present disclosure (first compound 1-2 and second compound 2-1) as the emissive layer has a driving voltage (3.5 V) that is 5.6 V lower than that (9.1 V) of Comparative Example 6 (which uses CBP and second compound 2-1 as the emissive layer), and the power efficiency of Example 6 is 13 lm/W (2.6 times) higher than that of Comparative Example 6 and the lifetime of Example 6 is 1215.8 hours (190 times) longer than that of Comparative Example 6.

These results show that the combination of the first compound and the second compound of the present disclosure can greatly improve device performance, which far exceeds the device effects when the second compound selected by the present disclosure is used as the dopant in combination with the compound in the related art as the host. This indicates the superiority of the combination of the first compound and the second compound of the present disclosure. In particular, this also fully proves the unexpected effects due to the use of the first compound selected by the present disclosure as the red phosphorescent host material in combination with the second compound with a particular structure.

Example 5 which uses the combination of the present disclosure (first compound 1-2 and second compound 2-43) as the emissive layer has a driving voltage (3.6 V) that is 0.8 V lower than that (4.4 V) of Comparative Example 8 which uses the current commercial host material, Compound A (using Compound A and second compound 2-43 as the emissive layer), and the power efficiency of Example 5 is 2 lm/W (7.4%) higher than that of Comparative Example 8 and the lifetime of Example 5 is 20 hours (2.3%) longer than that of Comparative Example 8. These data show that the material combination disclosed by the present disclosure can further improve the device performance based on the level of the commercial material, which is very rare.

These results show that the combination of the first compound and the second compound of the present disclosure can greatly improve the device performance and further improve the device performance based on the level of the current commercial host material. This further indicates the superiority of the combination of the first compound and the second compound of the present disclosure. In particular, this also fully proves the unexpected effects due to the use of the first compound selected by the present disclosure as the red phosphorescent host material in combination with the second compound with a particular structure.

In summary, the combination of the first compound and the second compound disclosed by the present disclosure, due to good matching in energy, can enable the device to exhibit excellent comprehensive performance, such as a lower driving voltage, higher efficiency and an ultra-long lifetime.

It is to be understood that various embodiments described herein are merely exemplary and not intended to limit the scope of the present disclosure. Therefore, it is apparent to those skilled in the art that the present disclosure as claimed may include variations of specific embodiments and preferred embodiments described herein. Many of the materials and structures described herein may be replaced with other materials and structures without departing from the spirit of the present disclosure. It is to be understood that various theories as to why the present disclosure works are not intended to be limitative.

What is claimed is:

1. An electroluminescent device, comprising:

an anode, a cathode, and an organic layer disposed between the anode and the cathode, wherein the organic layer comprises at least a first compound and a second compound;

the first compound has a structure of H-L-E;

H has a structure represented by Formula 1-a:

Formula 1-a

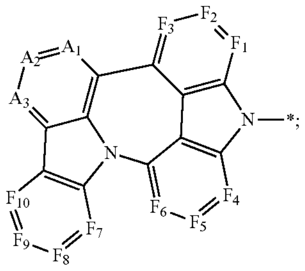

in Formula 1-a, $A_1$, $A_2$ and $A_3$ are, at each occurrence identically or differently, selected from CR, and $F_1$ to $F_{10}$ are, at each occurrence identically or differently, selected from $CR_f$; and E has a structure represented by Formula 2-d:

Formula 2-d

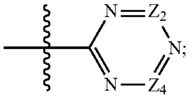

in Formula 2-d, $Z_2$ and $Z_4$ are each independently selected from $CR_z$;

L is selected from substituted or unsubstituted arylene having 6 to 30 carbon atoms, substituted or unsubstituted heteroarylene having 3 to 30 carbon atoms or a combination thereof;

R, $R_f$ and $R_z$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, a cyano group, a hydroxyl group, a sulfanyl group, and combinations thereof; and adjacent substituents R, $R_f$ can be optionally joined to form a ring;

the second compound is a metal complex having a general formula of $Ir(L_a)_2(L_b)$;

wherein, $L_a$ and $L_b$ are a first ligand and a second ligand coordinated to the Ir, respectively; $L_a$ and $L_b$ can be optionally joined to form a multidentate ligand;

the multiple $L_a$ may be the same or different;

the $L_a$ has a structure represented by Formula 3-1 or Formula 3-3:

Formula 3-1

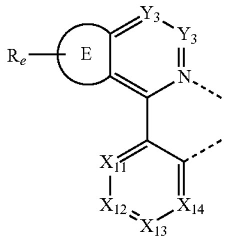

Formula 3-3

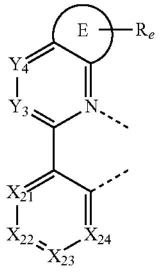

wherein, the ring E is selected from a benzene ring;

$R_e$ represents, at each occurrence identically or differently, mono-substitution, multiple substitutions or non-substitution;

$X_{11}$ to $X_{14}$ are, at each occurrence identically or differently, selected from $CR_{x1}$; $X_{31}$ to $X_{34}$ are, at each occurrence identically or differently, selected from $CR_{x3}$;

$Y_3$ and $Y_4$ are, at each occurrence identically or differently, selected from $CR_d$;

$R_{x1}$, $R_{x3}$, $R_d$ and $R_e$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, a cyano group, an isocyano group, a hydroxyl group, a sulfanyl group, and combinations thereof;

adjacent substituents $R_{x1}$, $R_d$ and $R_e$ can be optionally joined to form a ring;

when $R_{x3}$ is selected from substituted or unsubstituted alkyl having 1 to 20 carbon atoms, substituted or unsubstituted cycloalkyl having 3 to 20 ring carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, or substituted or unsubstituted amino having 0 to 20 carbon atoms, adjacent substituents $R_{x3}$ can be optionally joined to form a ring;

$L_b$ is selected from the following structure:

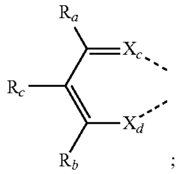

;

$R_a$, $R_b$ and $R_c$ represent, at each occurrence identically or differently, mono-substitution, multiple substitutions or non-substitution;

$X_c$ and $X_d$ are O;

$R_a$, $R_b$ and $R_c$, are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, a cyano group, and combinations thereof;

in structures of $L_b$, adjacent substituents $R_a$, $R_b$, $R_c$, can be optionally joined to form a ring; and, the following case is not comprised: the first compound is

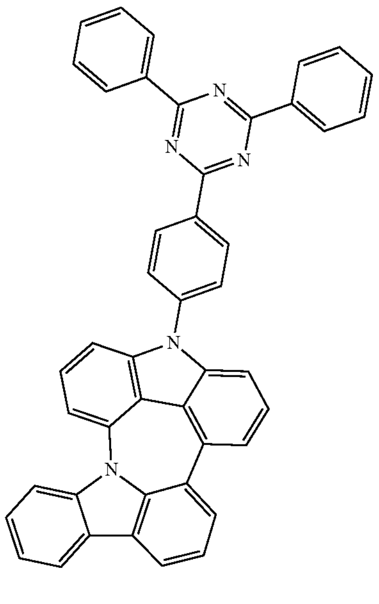 [SMILES: c1ccc(-c2nc(-c3ccccc3)nc(-c3ccc(-n4c5cccc6c7cccc8c9ccccc9n(c9cccc4c9c65)c78)cc3)n2)cc1]

while the second compound is

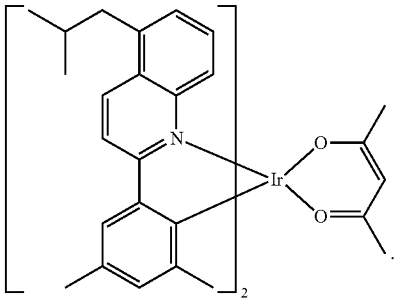

2. The electroluminescent device of claim 1, wherein the H has a structure represented by Formula 1-a:

Formula 1-a

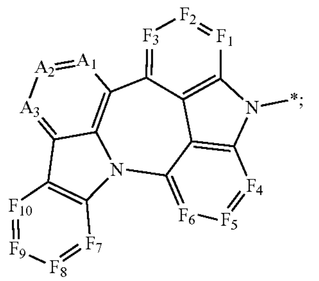

wherein $A_1$ to $A_3$ are, at each occurrence identically or differently, selected from CR, and $F_1$ to $F_{10}$ are, at each occurrence identically or differently, selected from $CR_f$; wherein R and $R_f$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, a cyano group, a hydroxyl group, a sulfanyl group, and combinations thereof;

adjacent substituents R, $R_f$ can be optionally joined to form a ring.

3. The electroluminescent device of claim 1, wherein the H is selected from the group consisting of the following structures:

H-1

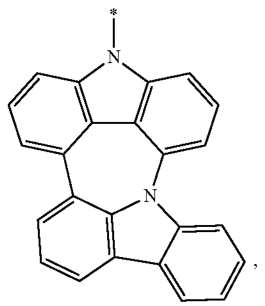

H-2

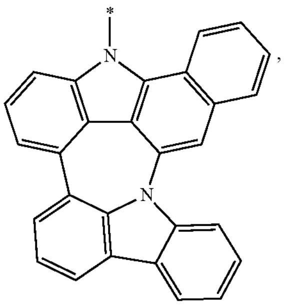

H-3

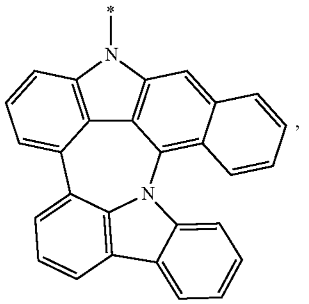

H-4

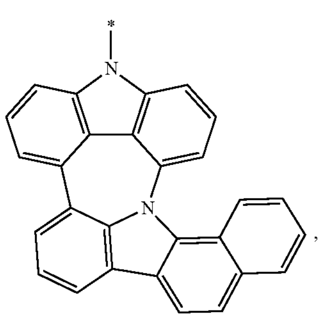

-continued
H-5
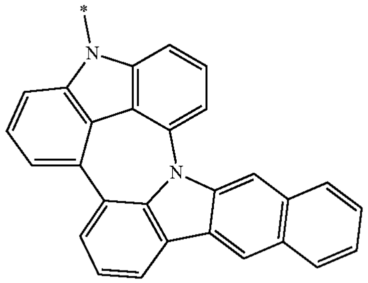
,
H-6
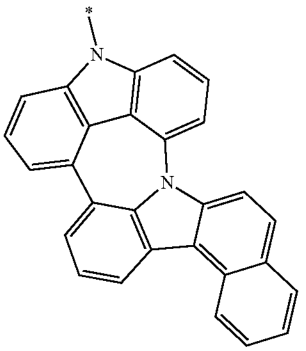
,
H-7
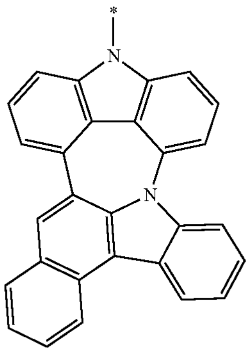
,
H-8
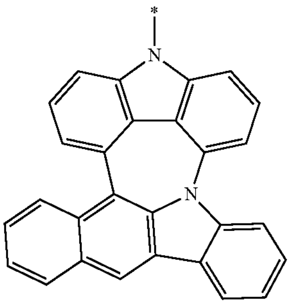
,
H-9
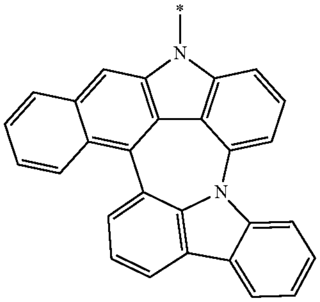
,
-continued
H-10
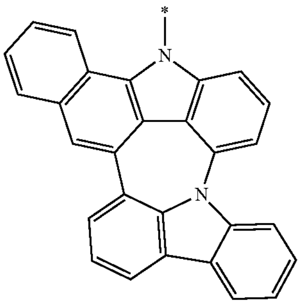
,
H-11
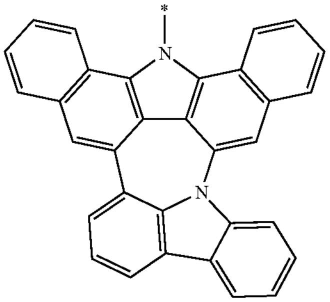
,
H-12
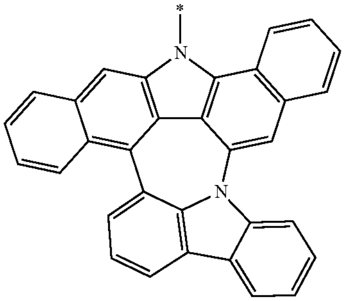
,
H-13
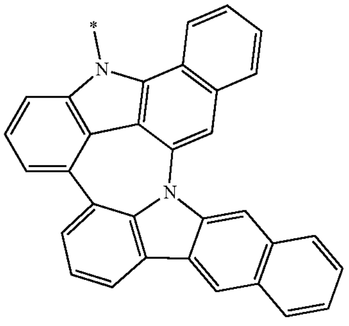
,
H-14
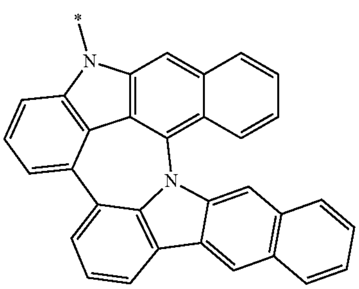
, -continued
H-15
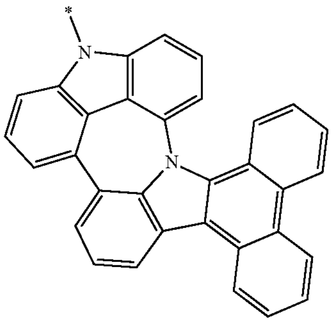
,
H-16
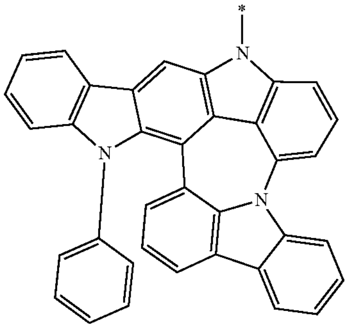
,
H-17
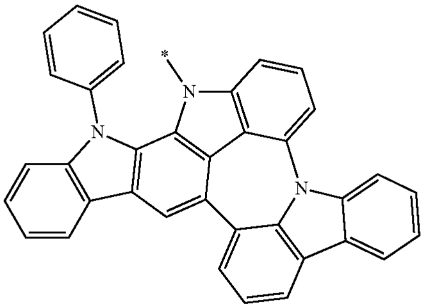
,
H-18
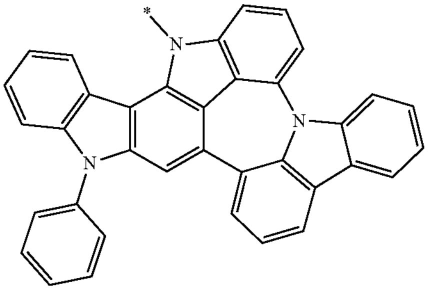
,
H-19
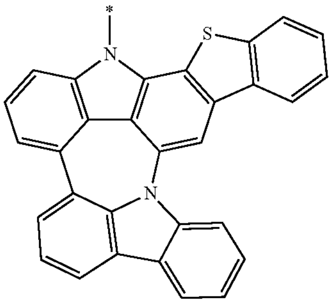
,
-continued
H-20
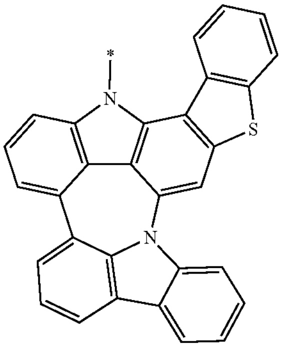
,
H-21
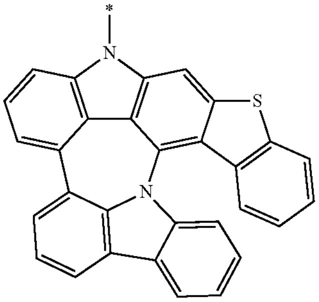
,
H-22
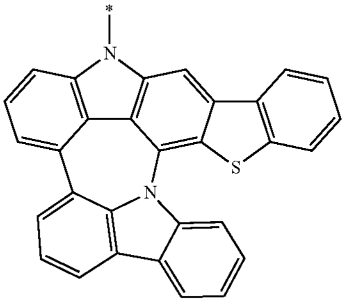
,
H-23
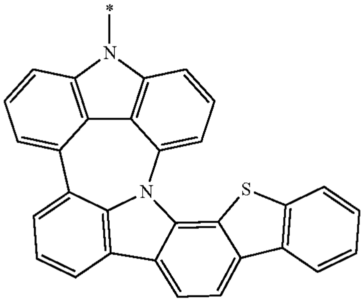
,
H-24
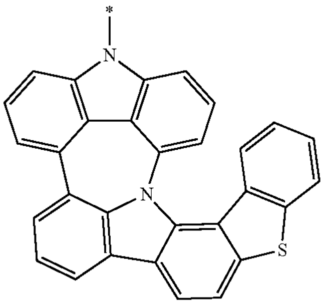
, -continued
H-25
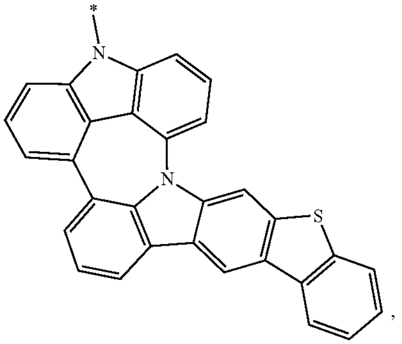
H-26
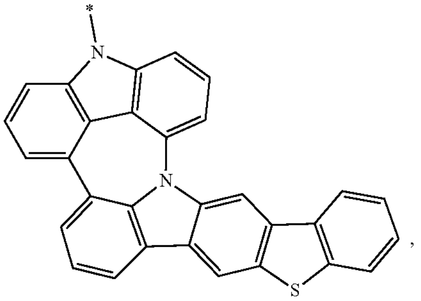
H-27
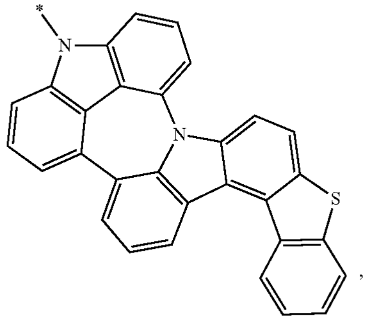
H-28
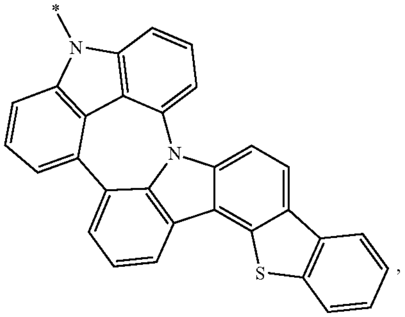
H-29
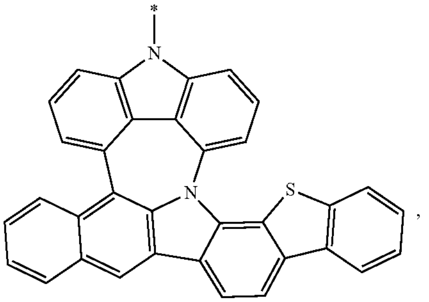
-continued
H-30
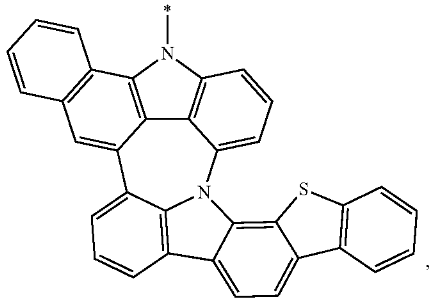
H-31
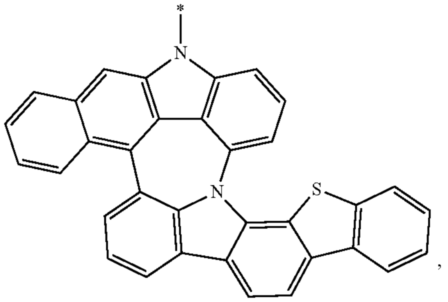
H-32
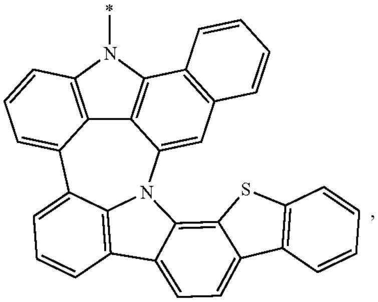
H-33
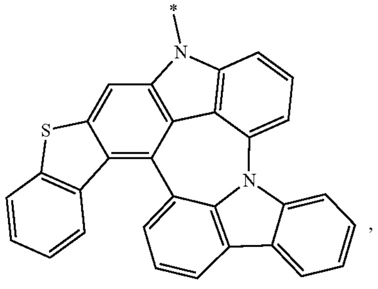
H-34
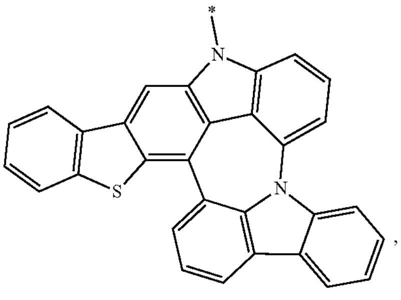

H-35
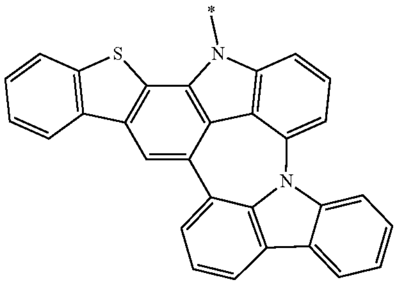
,
H-36
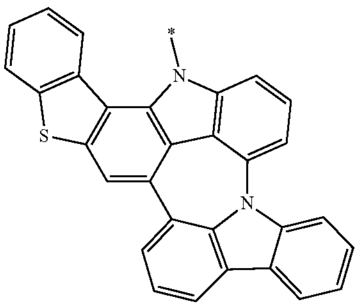
,
H-37
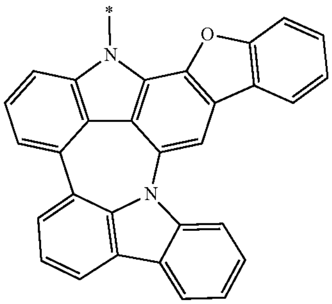
,
H-38
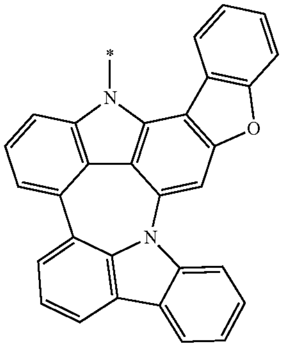
,
H-39
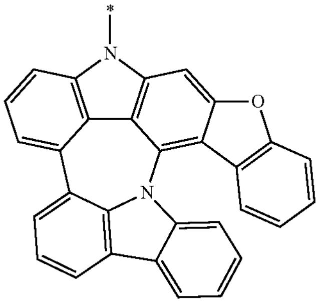
,
H-40
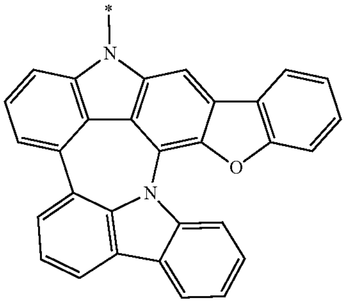
,
H-41
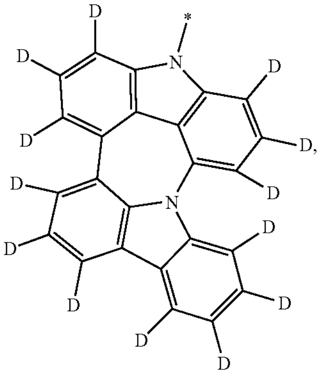
,
H-42
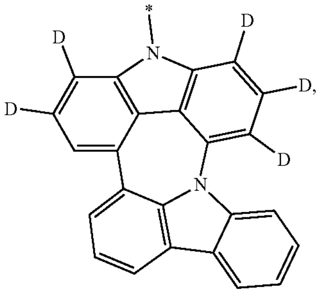
,
H-43
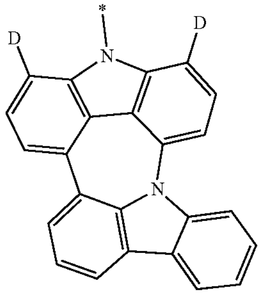
,
H-44
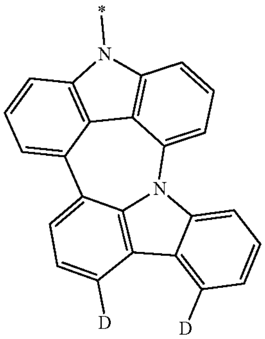
, -continued
H-45
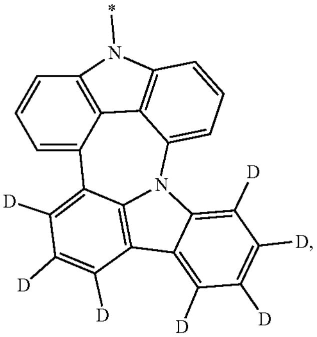
H-46
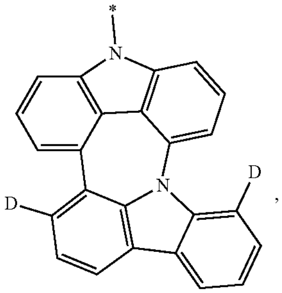
H-47
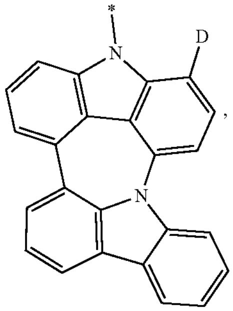
H-48
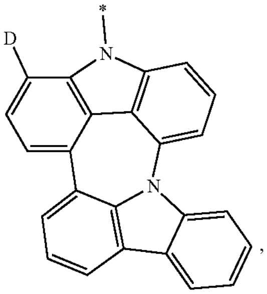
H-49
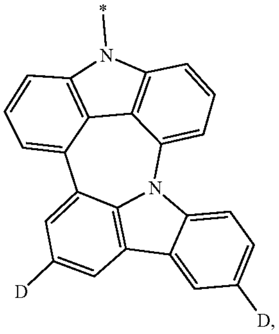
-continued
H-50
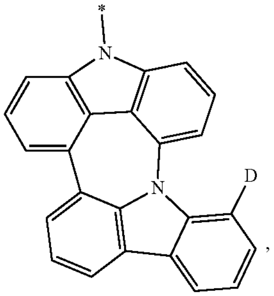
H-51
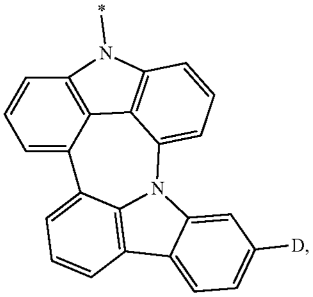
H-52
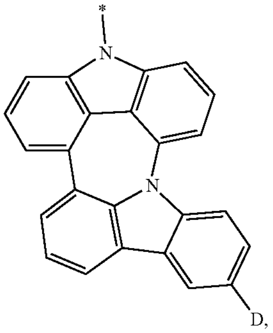
H-53
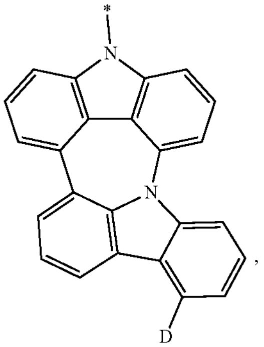
H-54
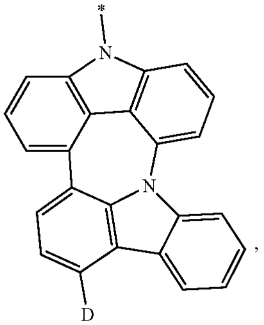

-continued
H-55
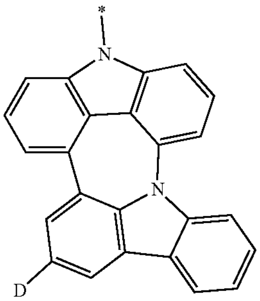
,
H-56
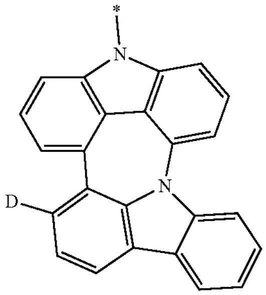
,
H-57
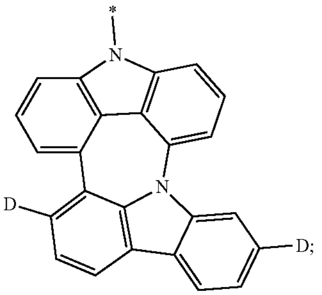
wherein optionally, hydrogens in the above structures can be partially or fully substituted with deuterium.
4. The electroluminescent device of claim 3, wherein the E is selected from the group consisting of the following structures:
E-1
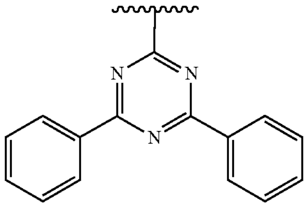
E-2
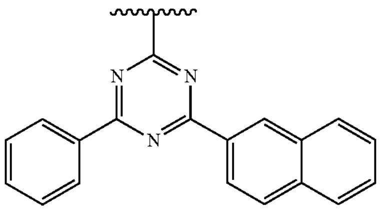
,
-continued
E-3
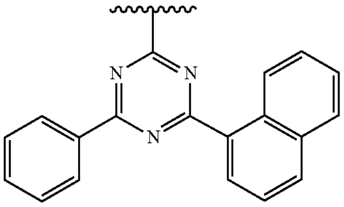
,
E-4
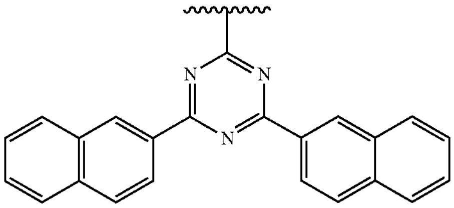
,
E-5
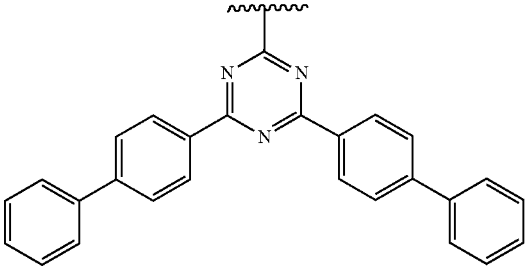
,
E-6
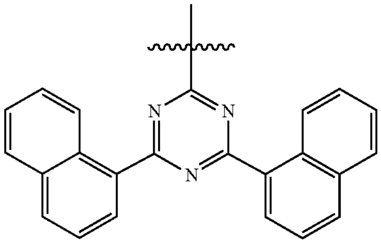
,
E-7
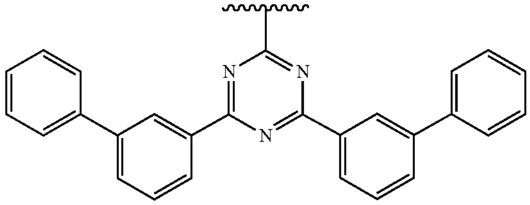
,
E-8
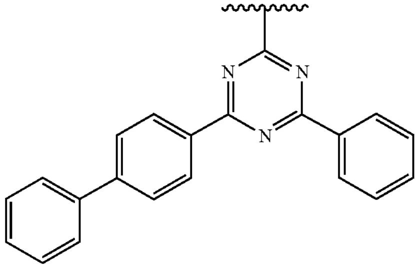
, -continued
E-9
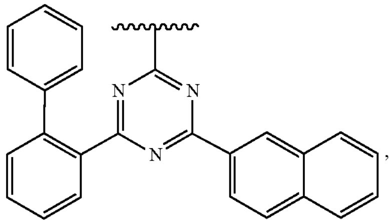
E-10
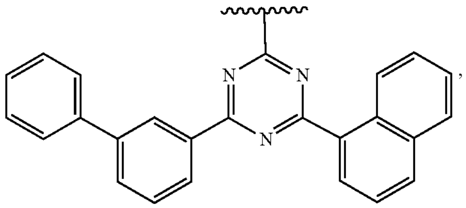
E-11
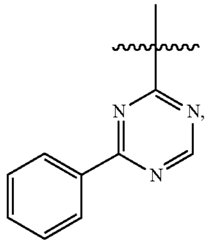
E-13
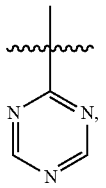
E-15
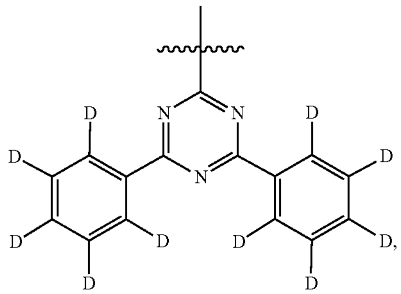
E-16
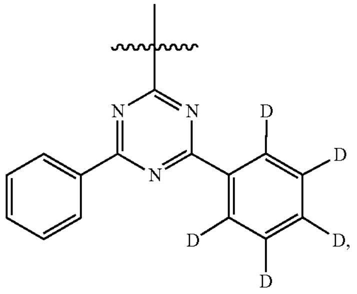
-continued
E-37
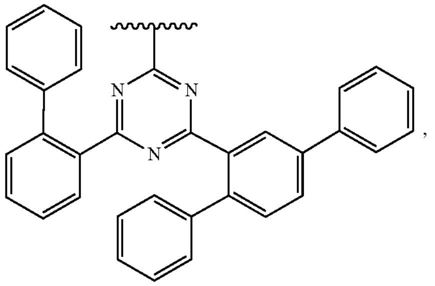
E-38
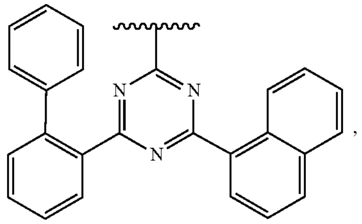
E-39
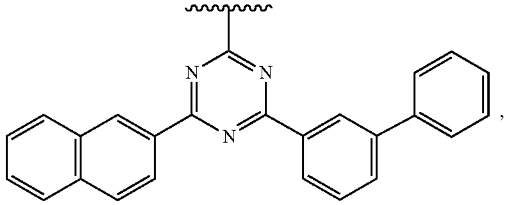
E-40
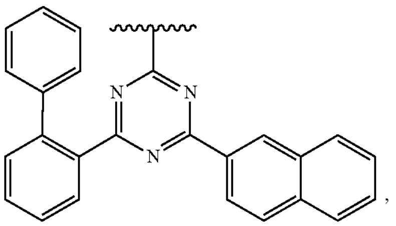
E-41
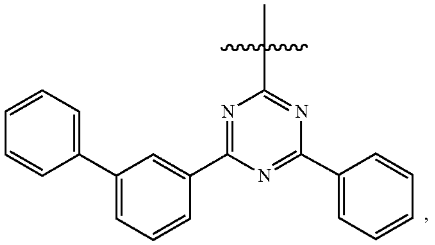
E-42
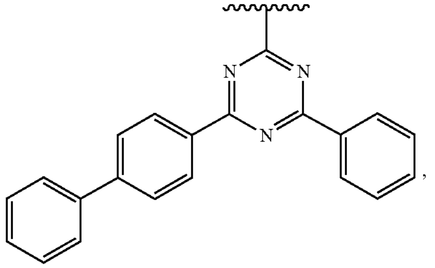

-continued
E-43
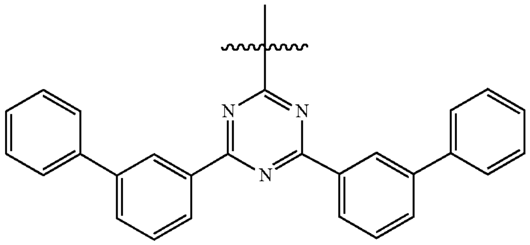,
E-44
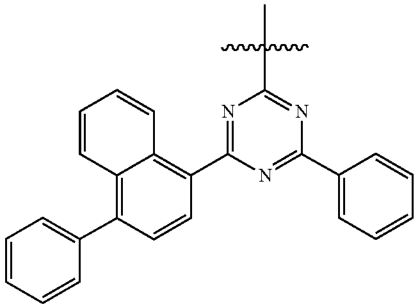,
E-45
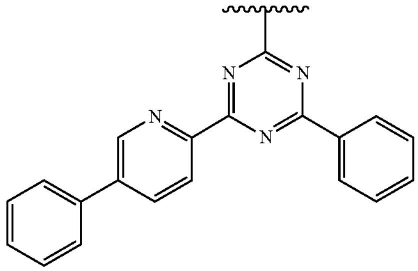,
E-46
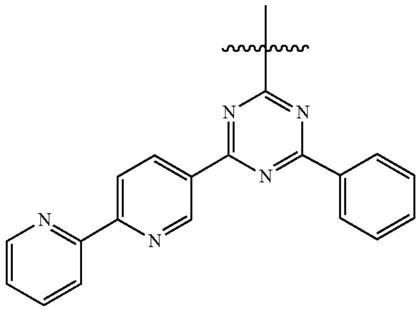,
E-47
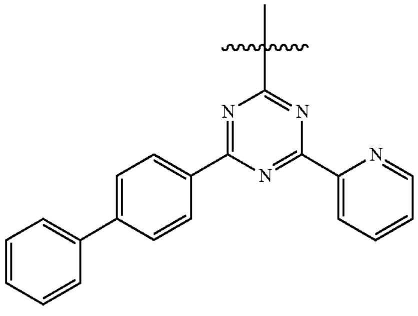,
-continued
E-48
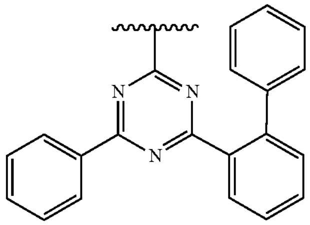,
E-49
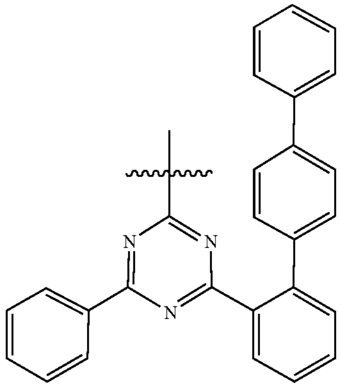,
E-50
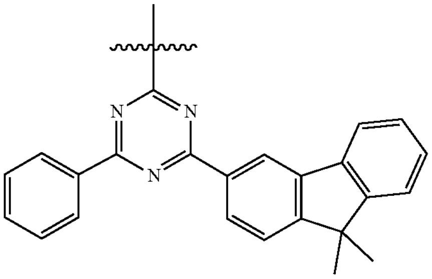,
E-51
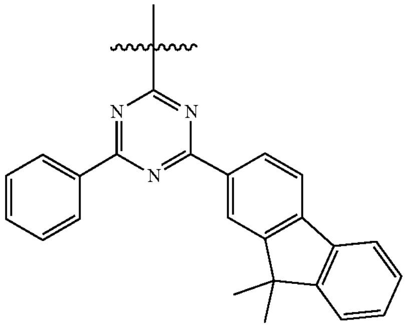,
E-52
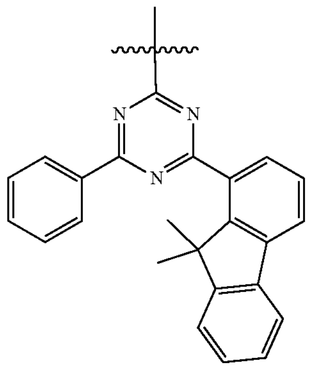, -continued
E-53
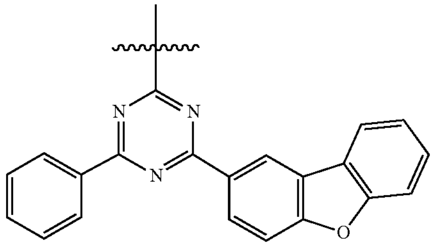
,
E-54
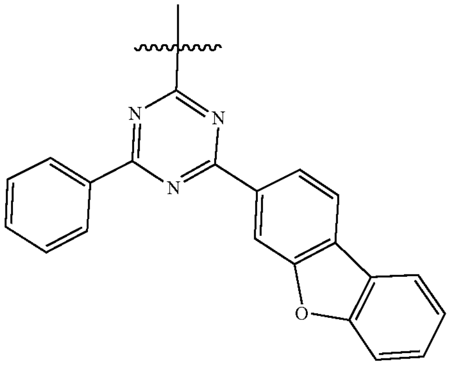
,
E-55
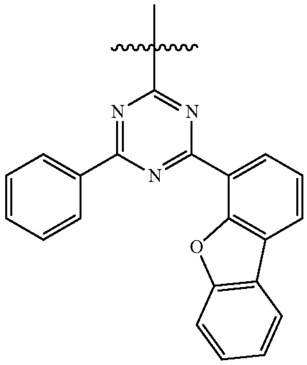
,
E-56
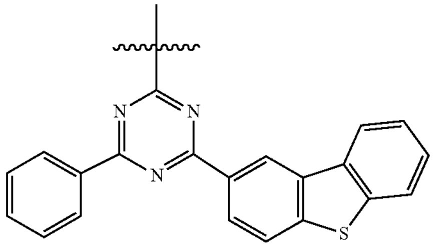
,
E-57
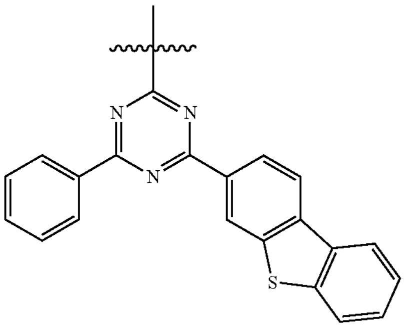
,
-continued
E-58
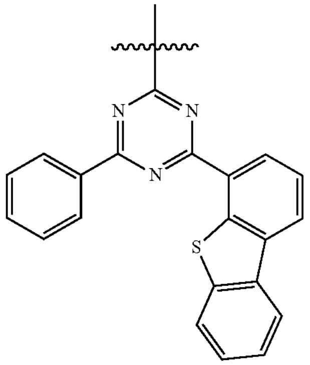
,
E-59
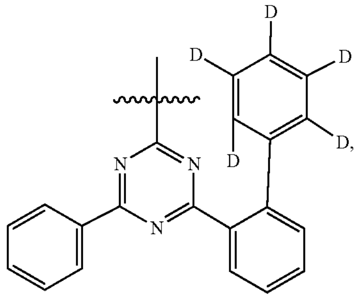
E-60
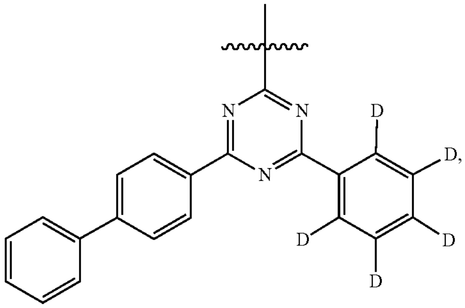
E-61
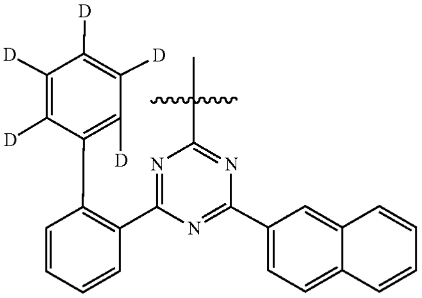
, -continued
E-62
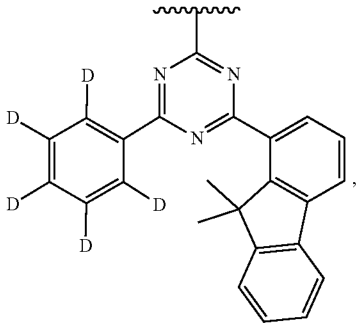
E-63
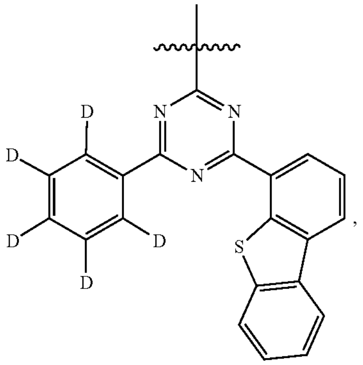
E-64
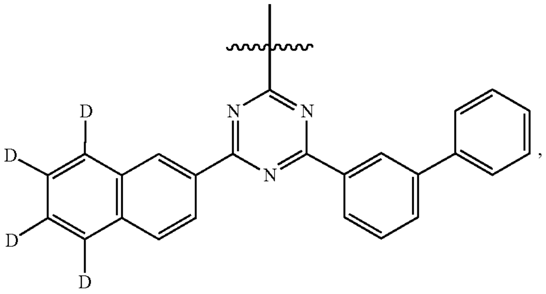
E-65
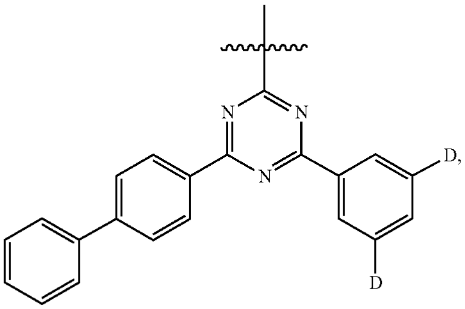
-continued
E-66
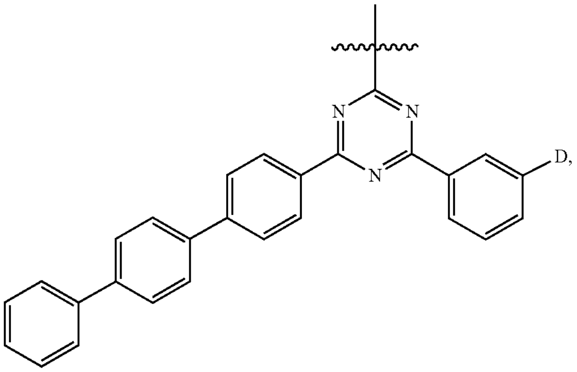
E-67
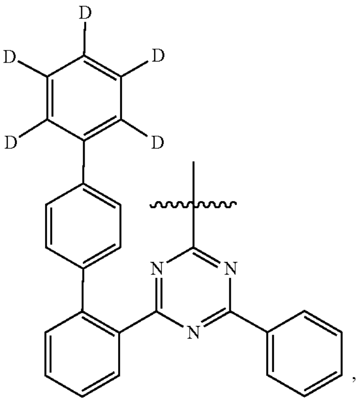
E-68
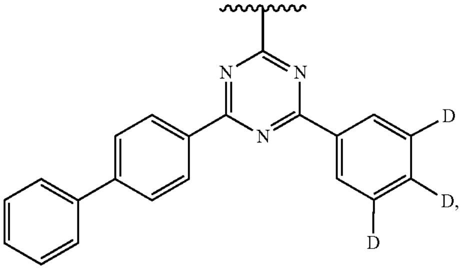
E-69
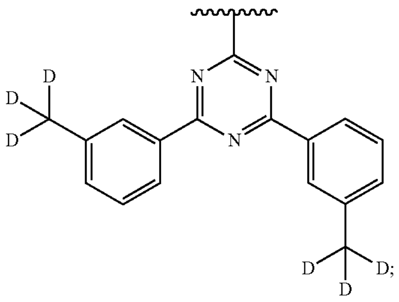
wherein in the above structures, represents the position where the structure is joined to the structure of L;
wherein optionally, hydrogens in the above structures can be partially or fully substituted with deuterium.

5. The electroluminescent device of claim 4, wherein the L is selected from the group consisting of the following structures:
L-0
a single bond,
L-1
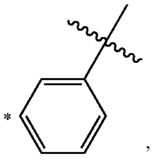
,
L-2
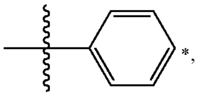
,
L-3
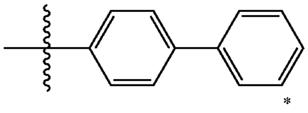
,
L-4
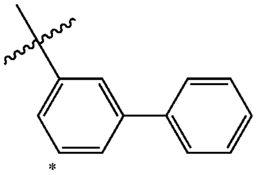
,
L-5
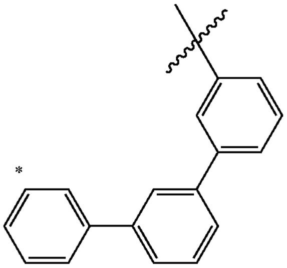
,
L-6
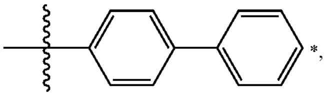
,
L-7
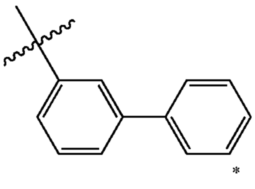
,
L-8
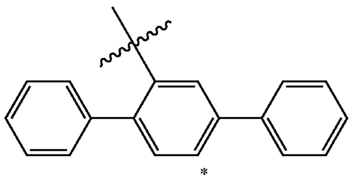
,
-continued
L-9
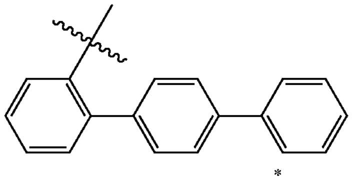
,
L-10
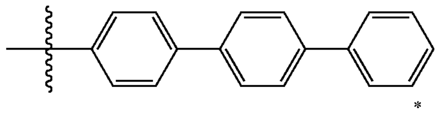
,
L-11
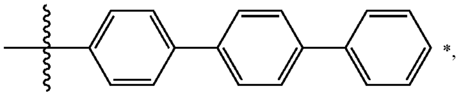
,
L-12
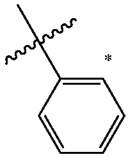
,
L-13
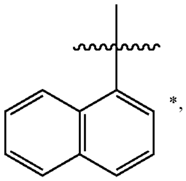
,
L-14
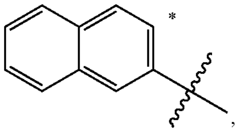
,
L-15
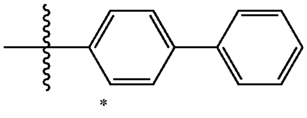
,
L-16
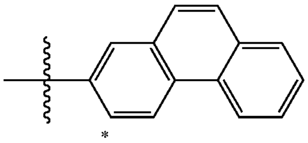
,
L-17
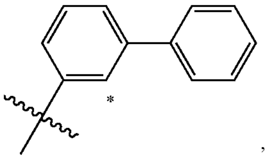
,
L-18
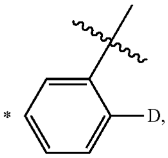
, -continued

L-19

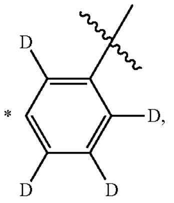

L-20

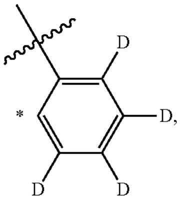

L-21

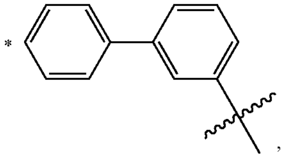

,

L-22

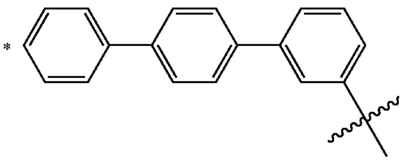

,

L-23

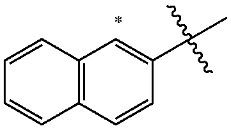

,

L-24

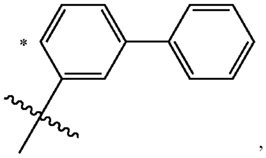

,

L-25

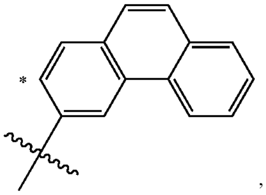

,

L-26

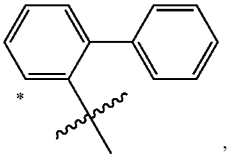

,

L-27

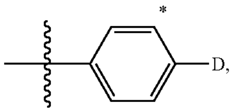

and

-continued

L-28

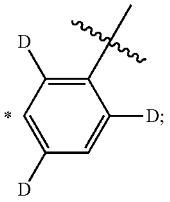

wherein in the above structures, "*" represents the position where the structure is joined to the structure of H, and ~ represents the position where the structure is joined to the structure of E;

wherein optionally, hydrogens in the above structures can be partially or fully substituted with deuterium.

6. The electroluminescent device of claim 5, wherein the first compound is selected from the group consisting of the following Compounds, wherein the Compounds have the structure of H-L-E, wherein H, L and E are respectively selected from structures in the following table:

| Compound No. | H | L | E |
|---|---|---|---|
| 1-2 | H-1 | L-1 | E-1 |
| 1-59 | H-1 | L-1 | E-2 |
| 1-60 | H-1 | L-1 | E-3 |
| 1-61 | H-1 | L-1 | E-4 |
| 1-62 | H-1 | L-1 | E-5 |
| 1-63 | H-1 | L-1 | E-6 |
| 1-64 | H-1 | L-1 | E-7 |
| 1-65 | H-1 | L-1 | E-8 |
| 1-66 | H-1 | L-1 | E-9 |
| 1-67 | H-1 | L-1 | E-10 |
| 1-68 | H-1 | L-1 | E-36 |
| 1-69 | H-1 | L-1 | E-37 |
| 1-70 | H-1 | L-1 | E-38 |
| 1-71 | H-1 | L-1 | E-39 |
| 1-72 | H-1 | L-1 | E-40 |
| 1-73 | H-1 | L-1 | E-41 |
| 1-74 | H-1 | L-1 | E-42 |
| 1-75 | H-1 | L-1 | E-43 |
| 1-76 | H-1 | L-1 | E-44 |
| 1-77 | H-1 | L-2 | E-15 |
| 1-78 | H-1 | L-2 | E-2 |
| 1-79 | H-1 | L-2 | E-3 |
| 1-80 | H-1 | L-2 | E-4 |
| 1-81 | H-1 | L-2 | E-5 |
| 1-82 | H-1 | L-2 | E-6 |
| 1-83 | H-1 | L-2 | E-7 |
| 1-84 | H-1 | L-2 | E-8 |
| 1-85 | H-1 | L-2 | E-9 |
| 1-86 | H-1 | L-2 | E-10 |
| 1-87 | H-1 | L-2 | E-45 |
| 1-88 | H-1 | L-2 | E-46 |
| 1-89 | H-1 | L-2 | E-47 |
| 1-90 | H-1 | L-2 | E-48 |
| 1-91 | H-1 | L-3 | E-49 |
| 1-92 | H-1 | L-3 | E-50 |
| 1-93 | H-1 | L-3 | E-51 |
| 1-94 | H-1 | L-3 | E-52 |
| 1-95 | H-1 | L-3 | E-53 |
| 1-96 | H-1 | L-3 | E-54 |
| 1-97 | H-1 | L-3 | E-55 |
| 1-98 | H-1 | L-3 | E-56 |
| 1-99 | H-1 | L-3 | E-57 |
| 1-100 | H-1 | L-3 | E-58 |
| 1-101 | H-1 | L-3 | E-1 |
| 1-102 | H-1 | L-3 | E-2 |
| 1-103 | H-1 | L-4 | E-3 |
| 1-104 | H-1 | L-4 | E-4 |
| 1-105 | H-1 | L-4 | E-5 |
| 1-106 | H-1 | L-4 | E-6 |
| 1-107 | H-1 | L-4 | E-7 |

-continued

| Compound No. | H | L | E |
|---|---|---|---|
| 1-108 | H-1 | L-4 | E-8 |
| 1-109 | H-1 | L-4 | E-9 |
| 1-110 | H-1 | L-4 | E-10 |
| 1-111 | H-1 | L-4 | E-40 |
| 1-112 | H-1 | L-4 | E-41 |
| 1-113 | H-1 | L-4 | E-42 |
| 1-114 | H-1 | L-4 | E-43 |
| 1-115 | H-1 | L-4 | E-44 |
| 1-116 | H-1 | L-4 | E-45 |
| 1-117 | H-1 | L-5 | E-46 |
| 1-118 | H-1 | L-5 | E-47 |
| 1-119 | H-1 | L-5 | E-48 |
| 1-120 | H-1 | L-5 | E-49 |
| 1-121 | H-1 | L-5 | E-50 |
| 1-122 | H-1 | L-5 | E-51 |
| 1-123 | H-1 | L-5 | E-52 |
| 1-124 | H-1 | L-5 | E-53 |
| 1-125 | H-1 | L-5 | E-54 |
| 1-126 | H-1 | L-5 | E-55 |
| 1-127 | H-1 | L-5 | E-56 |
| 1-128 | H-1 | L-5 | E-57 |
| 1-129 | H-1 | L-5 | E-58 |
| 1-130 | H-1 | L-5 | E-1 |
| 1-131 | H-1 | L-5 | E-2 |
| 1-132 | H-1 | L-5 | E-3 |
| 1-133 | H-1 | L-6 | E-4 |
| 1-134 | H-1 | L-6 | E-5 |
| 1-135 | H-1 | L-6 | E-6 |
| 1-136 | H-1 | L-6 | E-7 |
| 1-137 | H-1 | L-6 | E-8 |
| 1-138 | H-1 | L-6 | E-9 |
| 1-139 | H-1 | L-6 | E-10 |
| 1-140 | H-1 | L-6 | E-36 |
| 1-141 | H-1 | L-6 | E-37 |
| 1-142 | H-1 | L-6 | E-38 |
| 1-143 | H-1 | L-6 | E-39 |
| 1-144 | H-1 | L-6 | E-40 |
| 1-145 | H-1 | L-7 | E-41 |
| 1-146 | H-1 | L-7 | E-42 |
| 1-147 | H-1 | L-7 | E-43 |
| 1-148 | H-1 | L-7 | E-44 |
| 1-149 | H-1 | L-7 | E-45 |
| 1-150 | H-1 | L-7 | E-46 |
| 1-151 | H-1 | L-7 | E-47 |
| 1-152 | H-1 | L-8 | E-1 |
| 1-153 | H-1 | L-8 | E-2 |
| 1-154 | H-1 | L-8 | E-3 |
| 1-155 | H-1 | L-8 | E-4 |
| 1-156 | H-1 | L-8 | E-5 |
| 1-157 | H-1 | L-8 | E-6 |
| 1-158 | H-1 | L-8 | E-7 |
| 1-159 | H-1 | L-8 | E-8 |
| 1-160 | H-1 | L-8 | E-9 |
| 1-161 | H-1 | L-8 | E-10 |
| 1-162 | H-1 | L-8 | E-11 |
| 1-164 | H-1 | L-8 | E-13 |
| 1-166 | H-1 | L-9 | E-15 |
| 1-167 | H-1 | L-9 | E-16 |
| 1-187 | H-1 | L-11 | E-36 |
| 1-188 | H-1 | L-11 | E-37 |
| 1-189 | H-1 | L-11 | E-38 |
| 1-190 | H-1 | L-11 | E-39 |
| 1-191 | H-1 | L-12 | E-1 |
| 1-192 | H-1 | L-12 | E-2 |
| 1-193 | H-1 | L-12 | E-3 |
| 1-194 | H-1 | L-12 | E-4 |
| 1-195 | H-1 | L-12 | E-5 |
| 1-196 | H-1 | L-12 | E-6 |
| 1-197 | H-1 | L-12 | E-7 |
| 1-198 | H-1 | L-12 | E-8 |
| 1-199 | H-1 | L-12 | E-9 |
| 1-200 | H-1 | L-12 | E-10 |
| 1-201 | H-1 | L-12 | E-36 |
| 1-202 | H-1 | L-12 | E-37 |
| 1-203 | H-1 | L-12 | E-38 |
| 1-204 | H-1 | L-12 | E-39 |

-continued

| Compound No. | H | L | E |
|---|---|---|---|
| 1-205 | H-1 | L-12 | E-40 |
| 1-206 | H-1 | L-12 | E-41 |
| 1-207 | H-1 | L-13 | E-1 |
| 1-208 | H-1 | L-13 | E-2 |
| 1-209 | H-1 | L-13 | E-3 |
| 1-210 | H-1 | L-13 | E-4 |
| 1-211 | H-1 | L-13 | E-5 |
| 1-212 | H-1 | L-13 | E-6 |
| 1-213 | H-1 | L-13 | E-7 |
| 1-214 | H-1 | L-13 | E-8 |
| 1-215 | H-1 | L-13 | E-9 |
| 1-216 | H-1 | L-13 | E-10 |
| 1-217 | H-1 | L-13 | E-50 |
| 1-218 | H-1 | L-13 | E-51 |
| 1-219 | H-1 | L-13 | E-52 |
| 1-220 | H-1 | L-13 | E-53 |
| 1-221 | H-1 | L-13 | E-54 |
| 1-222 | H-1 | L-14 | E-1 |
| 1-223 | H-1 | L-14 | E-2 |
| 1-224 | H-1 | L-14 | E-3 |
| 1-225 | H-1 | L-14 | E-4 |
| 1-226 | H-1 | L-14 | E-5 |
| 1-227 | H-1 | L-14 | E-6 |
| 1-228 | H-1 | L-14 | E-7 |
| 1-229 | H-1 | L-14 | E-8 |
| 1-230 | H-1 | L-14 | E-9 |
| 1-231 | H-1 | L-14 | E-10 |
| 1-232 | H-1 | L-14 | E-38 |
| 1-233 | H-1 | L-14 | E-39 |
| 1-234 | H-1 | L-14 | E-40 |
| 1-235 | H-1 | L-14 | E-41 |
| 1-236 | H-1 | L-14 | E-42 |
| 1-237 | H-1 | L-14 | E-43 |
| 1-238 | H-1 | L-14 | E-44 |
| 1-239 | H-1 | L-14 | E-45 |
| 1-240 | H-1 | L-14 | E-46 |
| 1-241 | H-1 | L-14 | E-47 |
| 1-242 | H-1 | L-15 | E-1 |
| 1-243 | H-1 | L-15 | E-2 |
| 1-244 | H-1 | L-15 | E-3 |
| 1-245 | H-1 | L-15 | E-4 |
| 1-246 | H-1 | L-15 | E-5 |
| 1-247 | H-1 | L-15 | E-6 |
| 1-248 | H-1 | L-15 | E-7 |
| 1-249 | H-1 | L-15 | E-8 |
| 1-250 | H-1 | L-15 | E-9 |
| 1-251 | H-1 | L-15 | E-10 |
| 1-252 | H-1 | L-15 | E-44 |
| 1-253 | H-1 | L-15 | E-45 |
| 1-254 | H-1 | L-15 | E-46 |
| 1-255 | H-1 | L-15 | E-47 |
| 1-256 | H-1 | L-15 | E-48 |
| 1-257 | H-1 | L-15 | E-49 |
| 1-258 | H-1 | L-16 | E-1 |
| 1-259 | H-1 | L-16 | E-2 |
| 1-260 | H-1 | L-16 | E-3 |
| 1-261 | H-1 | L-16 | E-4 |
| 1-262 | H-1 | L-16 | E-5 |
| 1-263 | H-1 | L-16 | E-6 |
| 1-264 | H-1 | L-16 | E-7 |
| 1-265 | H-1 | L-16 | E-8 |
| 1-266 | H-1 | L-16 | E-9 |
| 1-267 | H-1 | L-16 | E-10 |
| 1-268 | H-1 | L-16 | E-45 |
| 1-269 | H-1 | L-16 | E-46 |
| 1-270 | H-1 | L-16 | E-47 |
| 1-271 | H-1 | L-16 | E-48 |
| 1-272 | H-1 | L-16 | E-49 |
| 1-273 | H-1 | L-16 | E-50 |
| 1-274 | H-1 | L-16 | E-51 |
| 1-275 | H-1 | L-17 | E-1 |
| 1-276 | H-1 | L-17 | E-2 |
| 1-277 | H-1 | L-17 | E-3 |
| 1-278 | H-1 | L-17 | E-4 |
| 1-279 | H-1 | L-17 | E-5 |
| 1-280 | H-1 | L-17 | E-6 |

-continued

| Compound No. | H | L | E |
|---|---|---|---|
| 1-281 | H-1 | L-17 | E-7 |
| 1-282 | H-1 | L-17 | E-8 |
| 1-283 | H-1 | L-17 | E-9 |
| 1-284 | H-1 | L-17 | E-10 |
| 1-285 | H-1 | L-17 | E-36 |
| 1-286 | H-1 | L-17 | E-37 |
| 1-287 | H-1 | L-17 | E-38 |
| 1-288 | H-1 | L-17 | E-39 |
| 1-289 | H-1 | L-17 | E-40 |
| 1-290 | H-1 | L-17 | E-41 |
| 1-291 | H-1 | L-17 | E-42 |
| 1-292 | H-1 | L-17 | E-43 |
| 1-293 | H-1 | L-17 | E-44 |
| 1-294 | H-1 | L-17 | E-45 |
| 1-295 | H-1 | L-17 | E-46 |
| 1-296 | H-1 | L-17 | E-47 |
| 1-297 | H-1 | L-17 | E-48 |
| 1-298 | H-1 | L-17 | E-49 |
| 1-299 | H-1 | L-17 | E-50 |
| 1-300 | H-1 | L-17 | E-51 |
| 1-357 | H-1 | L-18 | E-1 |
| 1-358 | H-1 | L-18 | E-2 |
| 1-359 | H-1 | L-18 | E-3 |
| 1-360 | H-1 | L-18 | E-4 |
| 1-361 | H-1 | L-18 | E-5 |
| 1-362 | H-1 | L-18 | E-6 |
| 1-363 | H-1 | L-18 | E-7 |
| 1-364 | H-1 | L-18 | E-8 |
| 1-365 | H-1 | L-18 | E-9 |
| 1-366 | H-1 | L-18 | E-10 |
| 1-367 | H-1 | L-18 | E-11 |
| 1-369 | H-1 | L-18 | E-13 |
| 1-371 | H-1 | L-18 | E-15 |
| 1-372 | H-1 | L-18 | E-16 |
| 1-379 | H-1 | L-19 | E-1 |
| 1-380 | H-1 | L-19 | E-2 |
| 1-381 | H-1 | L-19 | E-3 |
| 1-382 | H-1 | L-19 | E-4 |
| 1-383 | H-1 | L-19 | E-5 |
| 1-384 | H-1 | L-19 | E-6 |
| 1-385 | H-1 | L-19 | E-7 |
| 1-386 | H-1 | L-19 | E-8 |
| 1-387 | H-1 | L-19 | E-9 |
| 1-388 | H-1 | L-19 | E-10 |
| 1-389 | H-1 | L-19 | E-11 |
| 1-391 | H-1 | L-19 | E-13 |
| 1-393 | H-1 | L-19 | E-15 |
| 1-394 | H-1 | L-19 | E-16 |
| 1-401 | H-1 | L-20 | E-10 |
| 1-402 | H-1 | L-20 | E-11 |
| 1-403 | H-1 | L-20 | E-12 |
| 1-404 | H-1 | L-20 | E-13 |
| 1-406 | H-1 | L-20 | E-15 |
| 1-407 | H-1 | L-20 | E-16 |
| 1-423 | H-49 | L-1 | E-11 |
| 1-425 | H-49 | L-3 | E-13 |
| 1-427 | H-49 | L-5 | E-15 |
| 1-428 | H-49 | L-6 | E-16 |
| 1-436 | H-49 | L-14 | E-1 |
| 1-437 | H-49 | L-15 | E-1 |
| 1-438 | H-49 | L-16 | E-1 |
| 1-439 | H-49 | L-17 | E-1 |
| 1-440 | H-49 | L-18 | E-1 |
| 1-441 | H-49 | L-19 | E-1 |
| 1-442 | H-49 | L-20 | E-1 |
| 1-511 | H-1 | L-21 | E-1 |
| 1-512 | H-1 | L-22 | E-1 |
| 1-513 | H-1 | L-23 | E-1 |
| 1-514 | H-1 | L-24 | E-1 |
| 1-515 | H-1 | L-25 | E-1 |
| 1-516 | H-1 | L-26 | E-1 |
| 1-517 | H-1 | L-27 | E-1 |
| 1-518 | H-1 | L-28 | E-1 |
| 1-519 | H-1 | L-1 | E-69 |
| 1-520 | H-1 | L-12 | E-69. |

7. The electroluminescent device of claim 1, wherein the E has a structure represented by Formula 2-d:

Formula 2-d

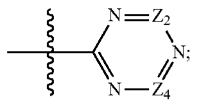

wherein $Z_2$ and $Z_4$ are, at each occurrence identically or differently, selected from $CR_z$;

wherein $R_z$ is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms, substituted or unsubstituted heteroaryl having 3 to 30 carbon atoms, a cyano group, and combinations thereof.

8. The electroluminescent device of claim 7, wherein $R_z$ is, at each occurrence identically or differently, selected from the group consisting of: hydrogen, deuterium, phenyl, naphthyl, biphenyl, terphenyl, fluorenyl, dibenzofuranyl, dibenzothienyl, pyridyl and combinations thereof.

9. The electroluminescent device of claim 1, wherein in the first compound, the L is selected from substituted or unsubstituted arylene having 6 to 30 carbon atoms.

10. The electroluminescent device of claim 9, wherein the L is selected from the group consisting of: phenylene, naphthylene, biphenylene, terphenylene, triphenylenylene, phenanthrylene and fluorenylidene.

11. The electroluminescent device of claim 1, wherein in the second compound, the $L_a$ has a structure represented by Formula 3-1 or Formula 3-3:

Formula 3-1

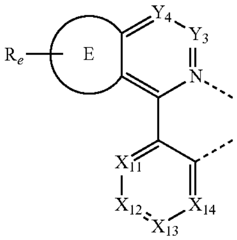

Formula 3-3

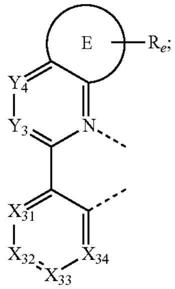

wherein, the ring E is selected from a benzene ring;

$R_e$ represents, at each occurrence identically or differently, mono-substitution, multiple substitutions or non-substitution;

$X_{11}$ to $X_{14}$ are, at each occurrence identically or differently, selected from $CR_{x1}$; $X_{31}$ to $X_{34}$ are, at each occurrence identically or differently, selected from $CR_{x3}$;

$Y_3$ and $Y_4$ are, at each occurrence identically or differently, selected from $CR_d$;

$R_{x1}$, $R_{x3}$, $R_d$ and $R_e$ are, at each occurrence identically or differently, selected from the group consisting of: hydrogen, halogen, substituted or unsubstituted alkyl having 1 to 20 carbon atoms, substituted or unsubstituted cycloalkyl having 3 to 20 ring carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, a cyano group, a hydroxyl group, a sulfanyl group, and combinations thereof;

adjacent substituents $R_{x1}$, $R_d$ and $R_e$ can be optionally joined to form a ring;

when $R_{x3}$ is selected from substituted or unsubstituted alkyl having 1 to 20 carbon atoms, substituted or unsubstituted cycloalkyl having 3 to 20 ring carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms or substituted or unsubstituted amino having 0 to 20 carbon atoms, adjacent substituents $R_{x3}$ can be optionally joined to form a ring.

12. The electroluminescent device of claim 1, wherein $L_a$ has a structure represented by Formula 3-6, Formula 3-8 or Formula 3-9:

Formula 3-6

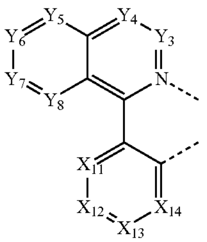

Formula 3-8

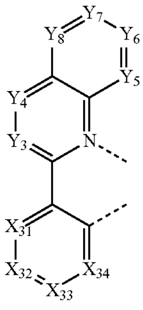

-continued

Formula 3-9

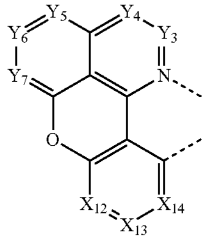

;

Formula 3-11

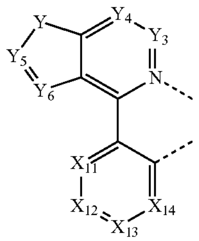

Formula 3-12

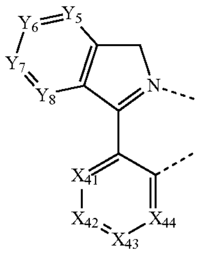

Formula 3-13

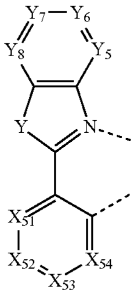

;

wherein $X_{11}$ to $X_{14}$ are, at each occurrence identically or differently, selected from $CR_{x1}$; $X_{31}$ to $X_{34}$ are, at each occurrence identically or differently, selected from $CR_{x3}$;

$Y_3$ and $Y_4$ are, at each occurrence identically or differently, selected from $CR_d$;

$Y_5$, $Y_6$, $Y_7$ and $Y_8$ are, at each occurrence identically or differently, selected from $CR_e$;

$R_{x1}$, $R_{x3}$, $R_d$ and $R_e$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, a cyano group, a hydroxyl group, a sulfanyl group, and combinations thereof;

adjacent substituents $R_{x1}$, $R_d$ and $R_e$ can be optionally joined to form a ring;

when $R_{x3}$ is selected from substituted or unsubstituted alkyl having 1 to 20 carbon atoms, substituted or unsubstituted cycloalkyl having 3 to 20 ring carbon atoms, substituted or unsubstituted alkenyl having 2 to 20 carbon atoms, substituted or unsubstituted aryl having 6 to 30 carbon atoms or substituted or unsubstituted heteroaryl having 3 to 30 carbon atoms, substituted or unsubstituted alkylsilyl having 3 to 20 carbon atoms, or substituted or unsubstituted arylsilyl having 6 to 20 carbon atoms, adjacent substituents $R_{x3}$ can be optionally joined to form a ring.

13. The electroluminescent device of claim 12, wherein in Formula 3-6, Formula 3-8 or Formula 3-9, $Y_3$ and/or $Y_4$ are/is selected from $CR_d$, and the $R_a$ is, at each occurrence identically or differently, selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, a cyano group, a hydroxyl group, a sulfanyl group, and combinations thereof.

14. The electroluminescent device of claim 12, wherein in Formula 3-6, Formula 3-8 or Formula 3-9, at least one or two of $Y_5$ to $Y_8$ are selected from $CR_e$, and the $R_e$ is, at each occurrence identically or differently, selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, a cyano group, a hydroxyl group, a sulfanyl group, and combinations thereof.

15. The electroluminescent device of claim 14, wherein in Formula 3-6 and Formula 3-9, $Y_6$ is selected from $CR_e$; in Formula 3-8, $Y_4$ is selected from $CR_d$ and/or at least one of $Y_6$ to $Y_8$ is selected from $CR_e$;

and, the $R_d$ and $R_e$ are, at each occurrence identically or differently, selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, a cyano group, a hydroxyl group, a sulfanyl group, and combinations thereof.

16. The electroluminescent device of claim 15, wherein the $R_d$ and $R_e$ are, at each occurrence identically or differently, selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms, substituted or unsubstituted heteroaryl having 3 to 30 carbon atoms, and combinations thereof.

17. The electroluminescent device of claim 12, wherein in Formula 3-6, Formula 3-8 or Formula 3-9, at least one or two of $X_{11}$ to $X_{14}$ are selected from $CR_{x1}$, at least one or two of $X_{31}$ to $X_{34}$ are selected from $CR_{x3}$, and the $R_{x1}$ and $R_{x3}$ are, at each occurrence identically or differently, selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, a cyano group, a hydroxyl group, a sulfanyl group, and combinations thereof.

18. The electroluminescent device of claim 17, wherein in Formula 3-6, Formula 3-8 or Formula 3-9, $X_{12}$ and/or $X_{14}$ are/is selected from $CR_{x1}$, $X_{32}$ and/or $X_{34}$ are/is selected from $CR_{x3}$, and the $R_{x1}$ and $R_{x3}$ are, at each occurrence identically or differently, selected from the group consisting of: substituted or unsubstituted alkyl having 1 to 10 carbon atoms, substituted or unsubstituted cycloalkyl having 3 to 10 ring carbon atoms, substituted or unsubstituted aryl having 6 to 20 carbon atoms, substituted or unsubstituted heteroaryl having 3 to 20 carbon atoms, substituted or unsubstituted alkylsilyl having 3 to 20 carbon atoms, substituted or unsubstituted arylsilyl having 6 to 20 carbon atoms and combinations thereof.

19. The electroluminescent device of claim 18, wherein in Formula 3-6, Formula 3-8 or Formula 3-9, $X_{12}$ and $X_{14}$ are each independently selected from $CR_{x1}$, $X_{32}$ and $X_{34}$ are each independently selected from $CR_{x3}$, and the $R_{x1}$ and $R_{x3}$ are, at each occurrence identically or differently, selected from the group consisting of: deuterium, methyl, ethyl, propyl, isopropyl, n-butyl, isobutyl, t-butyl, cyclopentyl, cyclohexyl, deuterated methyl, deuterated ethyl, deuterated propyl, deuterated isopropyl, deuterated n-butyl, deuterated isobutyl, deuterated t-butyl, deuterated cyclopentyl, deuterated cyclohexyl and combinations thereof.

20. The electroluminescent device of claim 1, wherein $L_a$ is, at each occurrence identically or differently, selected from the group consisting of the following structures:

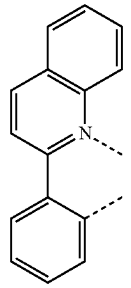

$L_{a-35}$

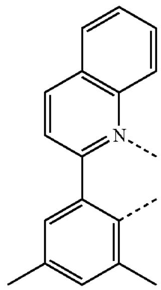

$L_{a-36}$

-continued
$L_{a\text{-}37}$
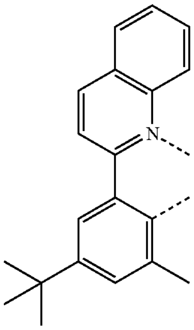
$L_{a\text{-}38}$
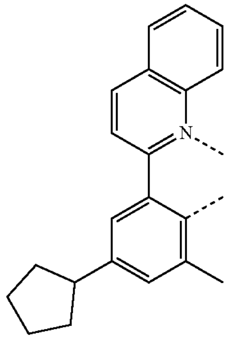
$L_{a\text{-}39}$
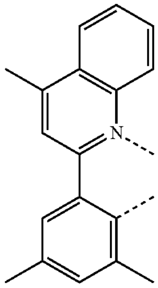
$L_{a\text{-}40}$
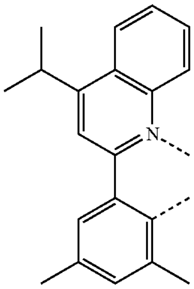
$L_{a\text{-}41}$
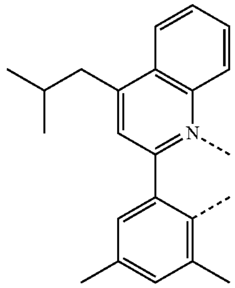
-continued
$L_{a\text{-}42}$
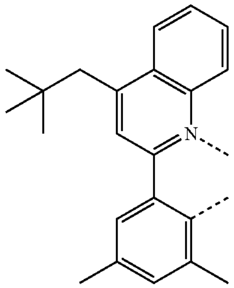
$L_{a\text{-}43}$
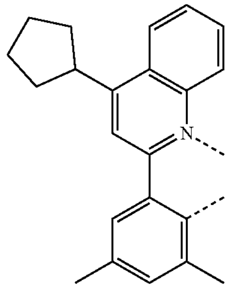
$L_{a\text{-}44}$
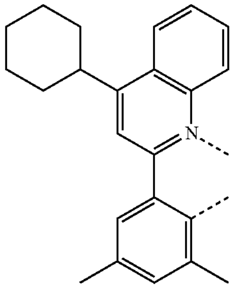
$L_{a\text{-}45}$
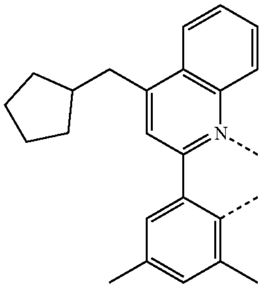
$L_{a\text{-}46}$
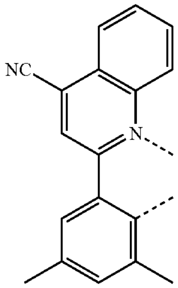

$L_{a\text{-}47}$
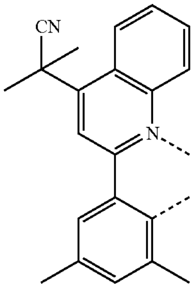
$L_{a\text{-}48}$
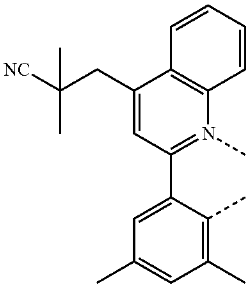
$L_{a\text{-}49}$
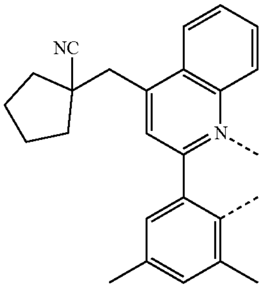
$L_{a\text{-}50}$
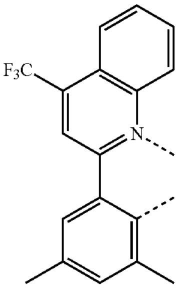
$L_{a\text{-}51}$
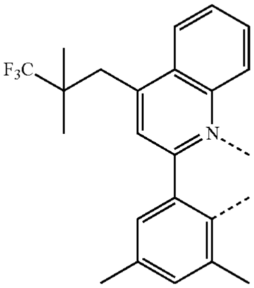
$L_{a\text{-}52}$
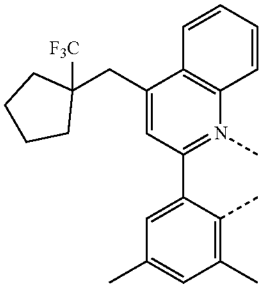
$L_{a\text{-}53}$
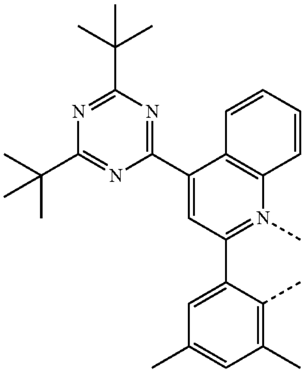
$L_{a\text{-}54}$
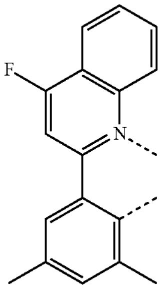
$L_{a\text{-}55}$
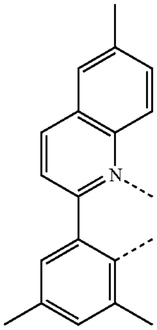

-continued
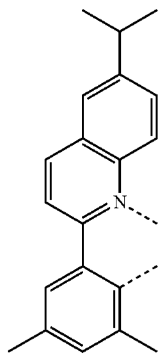
$L_{a-56}$
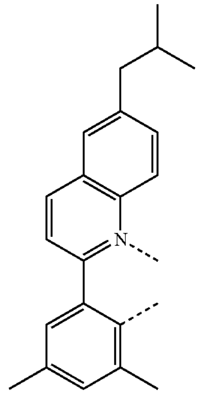
$L_{a-57}$
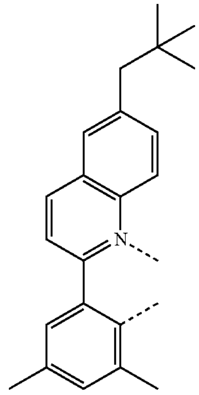
$L_{a-58}$
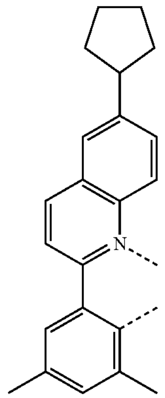
$L_{a-59}$
-continued
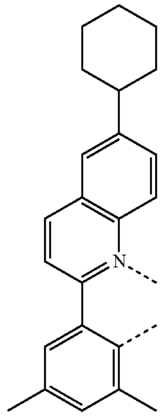
$L_{a-60}$
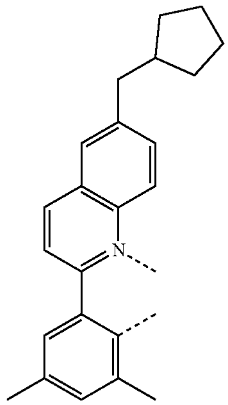
$L_{a-61}$
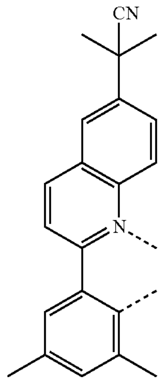
$L_{a-62}$
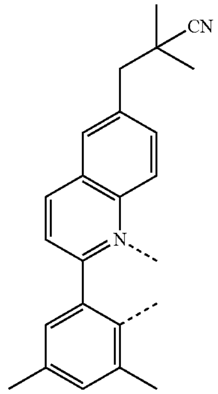
$L_{a-63}$ -continued
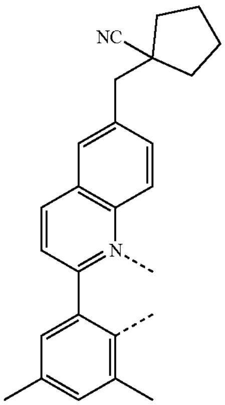
$L_{a-64}$
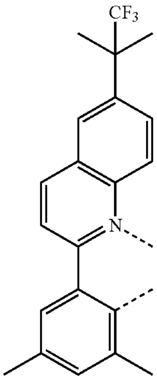
$L_{a-65}$
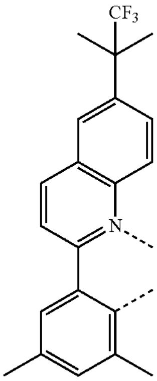
$L_{a-66}$
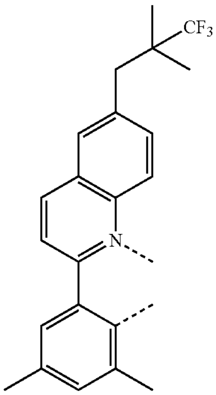
$L_{a-67}$
-continued
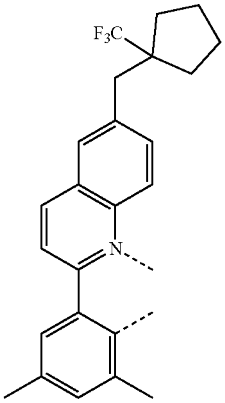
$L_{a-68}$
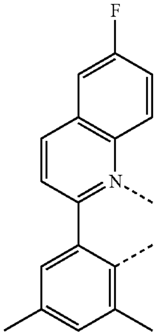
$L_{a-69}$
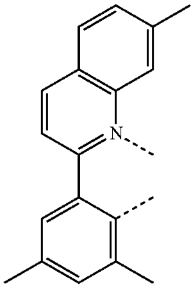
$L_{a-70}$
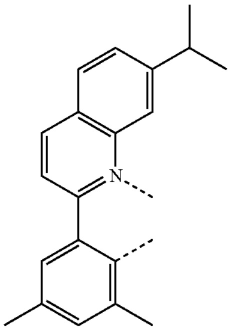
$L_{a-71}$

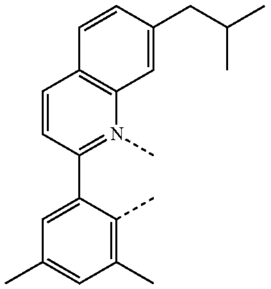
$L_{a-72}$
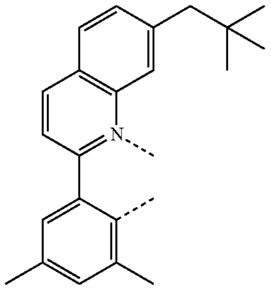
$L_{a-73}$
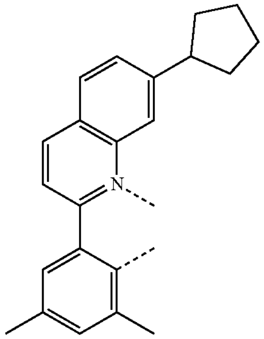
$L_{a-74}$
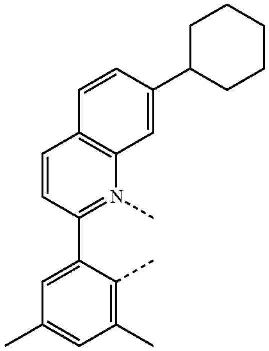
$L_{a-75}$
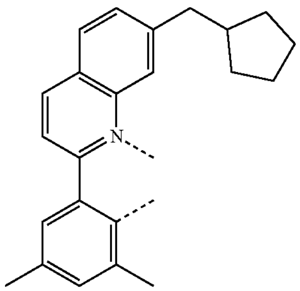
$L_{a-76}$
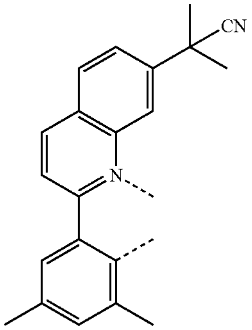
$L_{a-77}$
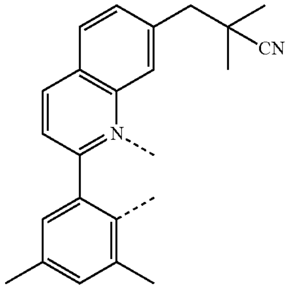
$L_{a-78}$
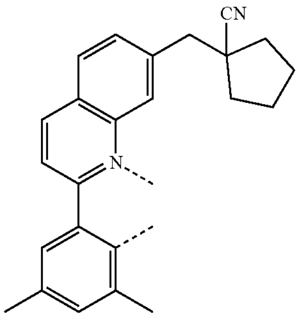
$L_{a-79}$
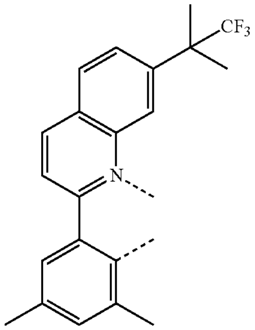
$L_{a-80}$
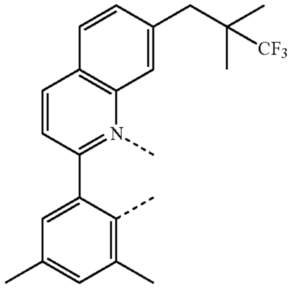
$L_{a-81}$ -continued
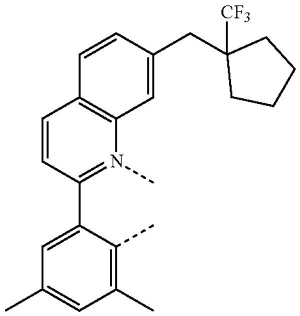
$L_{a}$-82
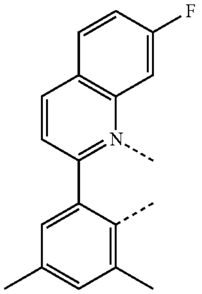
$L_{a}$-83
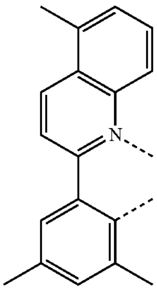
$L_{a}$-84
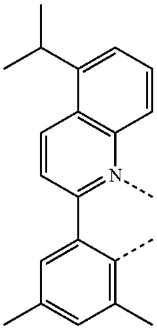
$L_{a}$-85
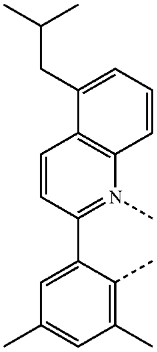
$L_{a}$-86
-continued
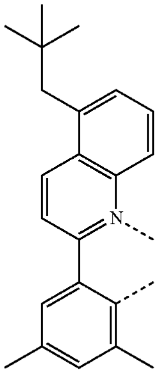
$L_{a}$-87
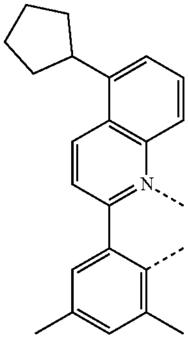
$L_{a}$-88
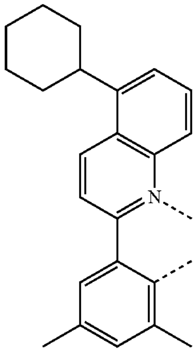
$L_{a}$-89
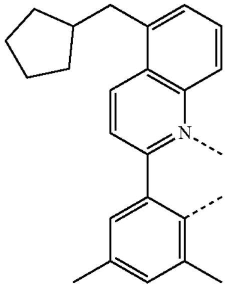
$L_{a}$-90

-continued
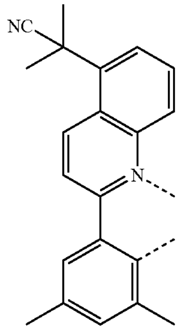
$L_{a\text{-}91}$
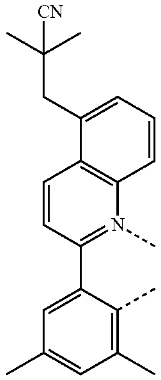
$L_{a\text{-}92}$
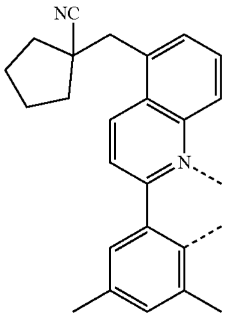
$L_{a\text{-}93}$
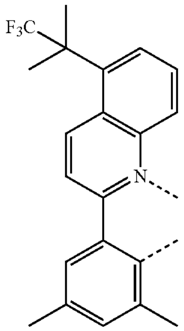
$L_{a\text{-}94}$
-continued
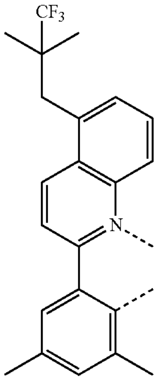
$L_{a\text{-}95}$
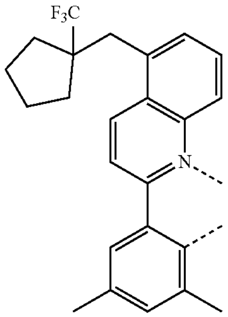
$L_{a\text{-}96}$
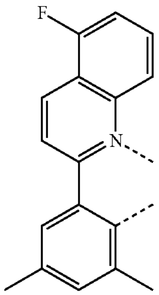
$L_{a\text{-}97}$
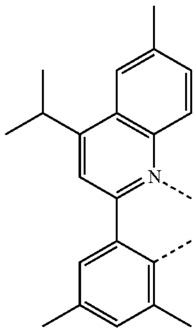
$L_{a\text{-}98}$ -continued
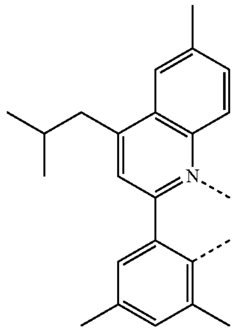
$L_{a\text{-}99}$
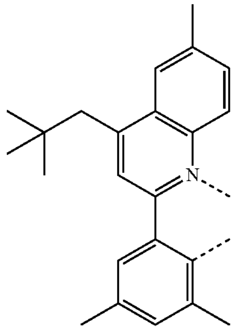
$L_{a\text{-}100}$
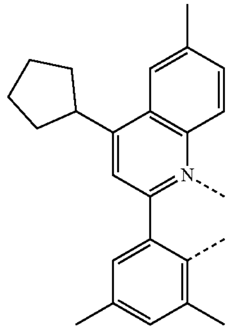
$L_{a\text{-}101}$
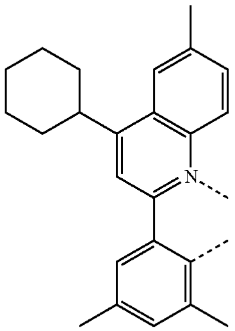
$L_{a\text{-}102}$
-continued
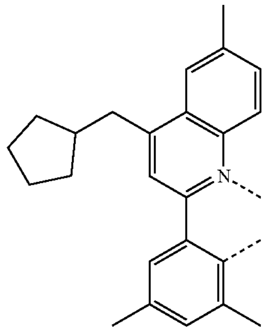
$L_{a\text{-}103}$
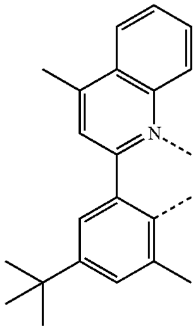
$L_{a\text{-}104}$
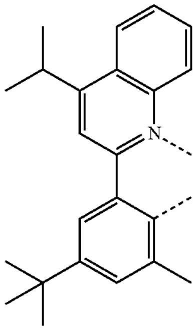
$L_{a\text{-}105}$
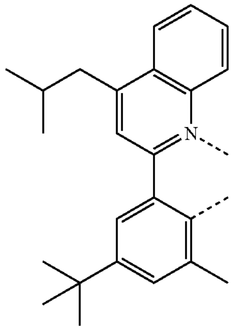
$L_{a\text{-}106}$ -continued
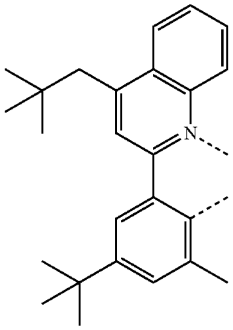
$L_{a}$-107
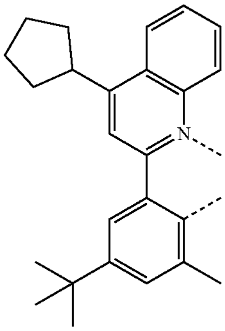
$L_{a}$-108
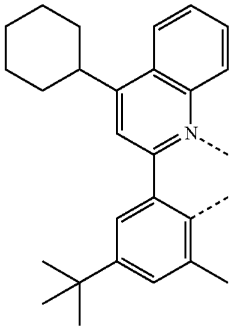
$L_{a}$-109
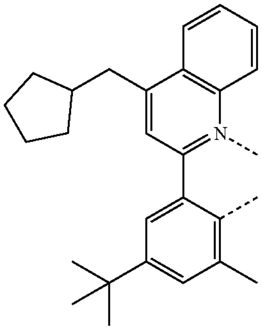
$L_{a}$-110
-continued
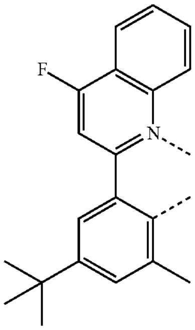
$L_{a}$-111
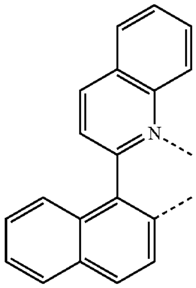
$L_{a}$-112
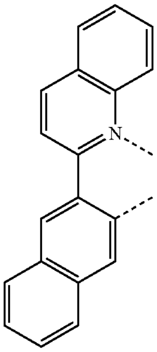
$L_{a}$-113
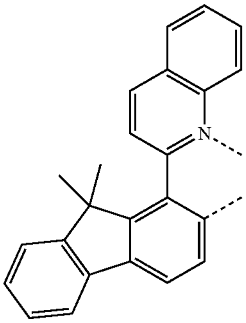
$L_{a}$-114

-continued
$L_{a-115}$
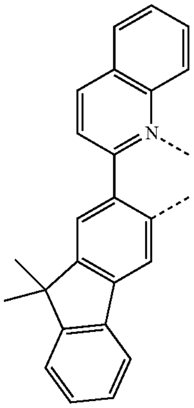
$L_{a-116}$
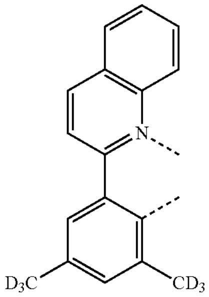
$L_{a-117}$
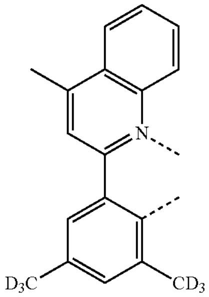
$L_{a-118}$
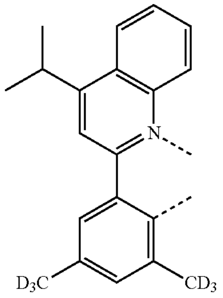
$L_{a-119}$
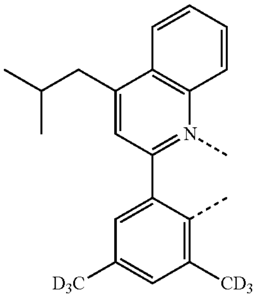
-continued
$L_{a-120}$
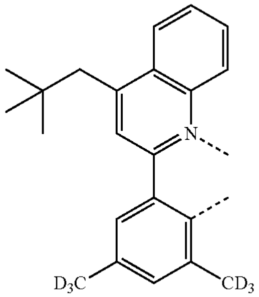
$L_{a-121}$
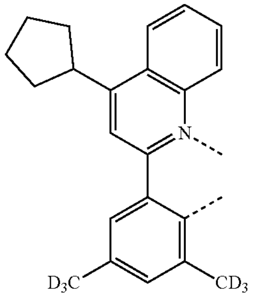
$L_{a-122}$
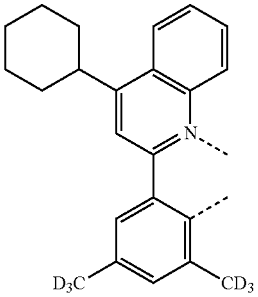
$L_{a-123}$
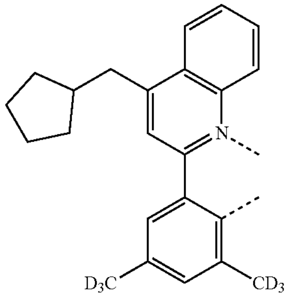
$L_{a-124}$
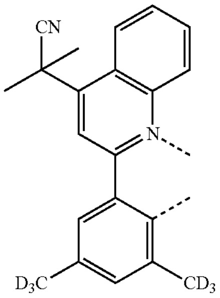

-continued
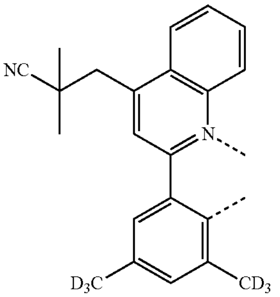
$L_{a-125}$
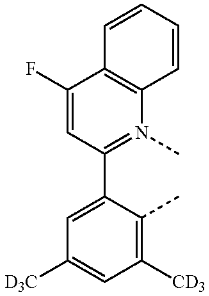
$L_{a-126}$
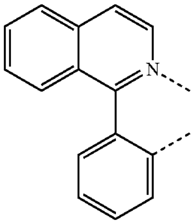
$L_{a-127}$
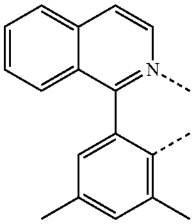
$L_{a-128}$
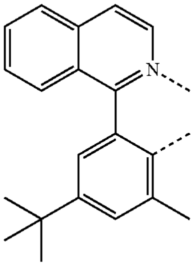
$L_{a-129}$
-continued
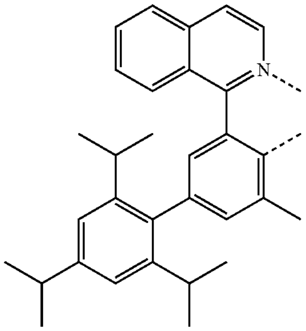
$L_{a-130}$
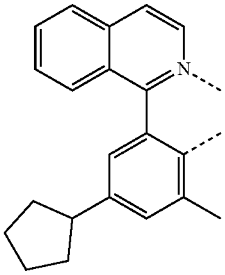
$L_{a-131}$
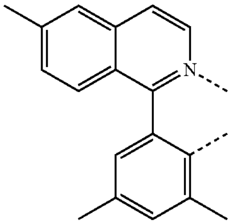
$L_{a-132}$
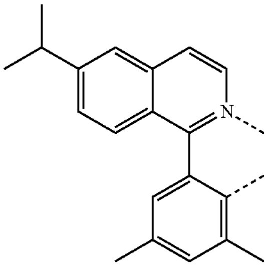
$L_{a-133}$
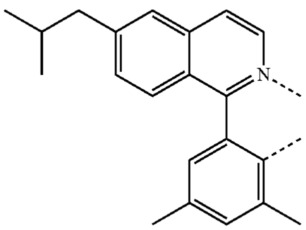
$L_{a-134}$
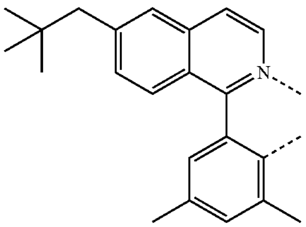
$L_{a-135}$ -continued
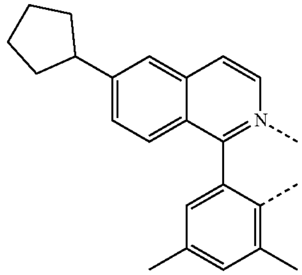
$L_{a}$-136
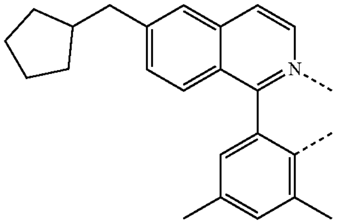
$L_{a}$-137
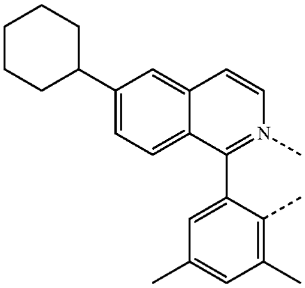
$L_{a}$-138
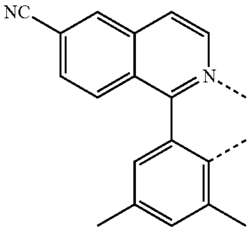
$L_{a}$-139
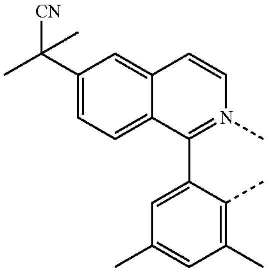
$L_{a}$-140
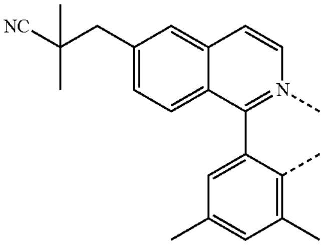
$L_{a}$-141
-continued
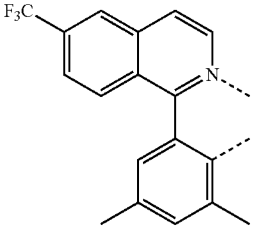
$L_{a}$-142
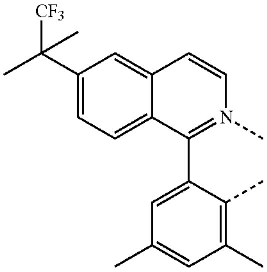
$L_{a}$-143
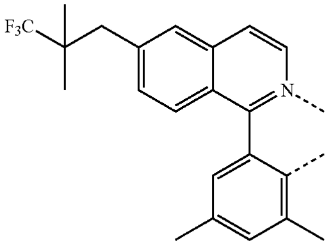
$L_{a}$-144
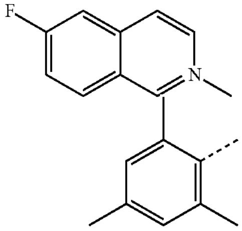
$L_{a}$-145
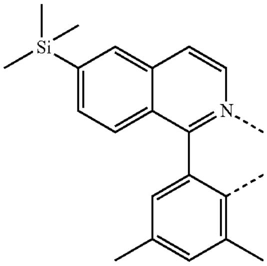
$L_{a}$-146
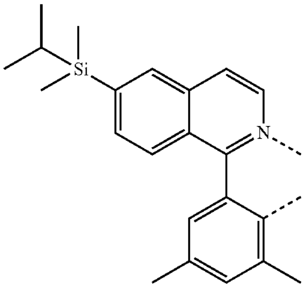
$L_{a}$-147

-continued
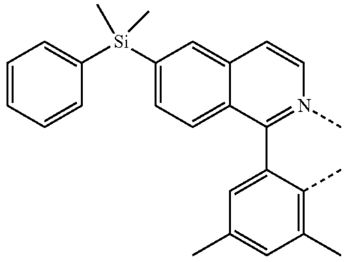
$L_{a-148}$
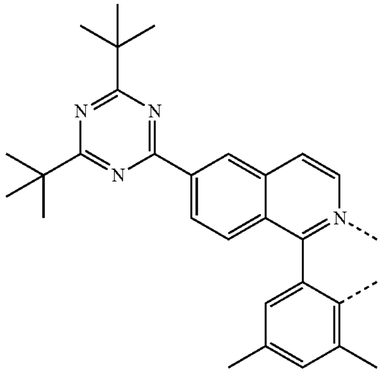
$L_{a-149}$
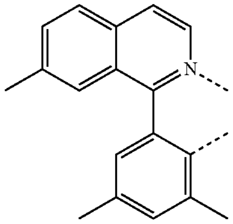
$L_{a-150}$
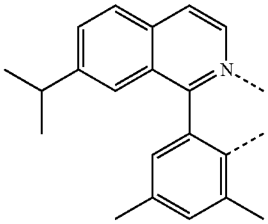
$L_{a-151}$
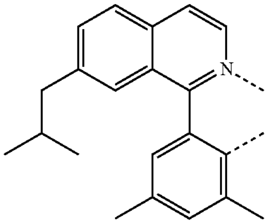
$L_{a-152}$
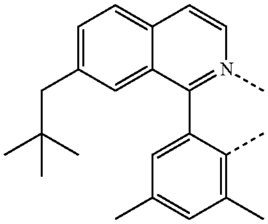
$L_{a-153}$
-continued
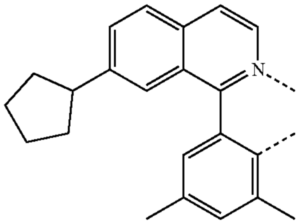
$L_{a-154}$
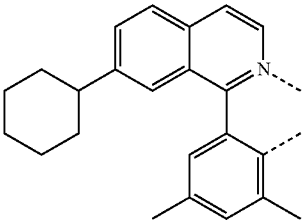
$L_{a-155}$
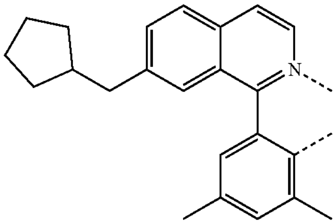
$L_{a-156}$
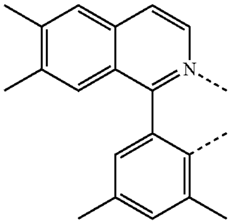
$L_{a-157}$
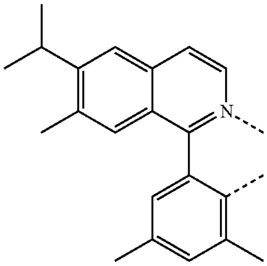
$L_{a-158}$
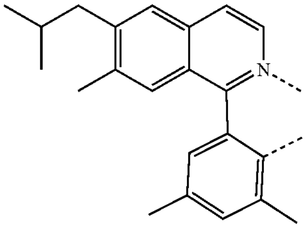
$L_{a-159}$ -continued
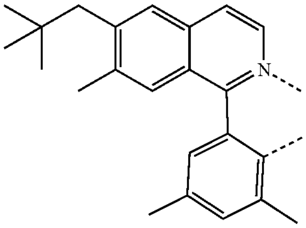
$L_{a-160}$
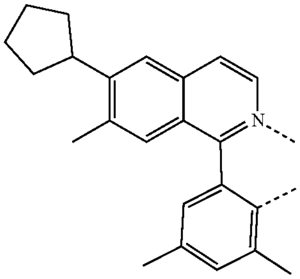
$L_{a-161}$
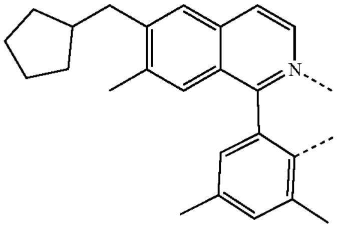
$L_{a-162}$
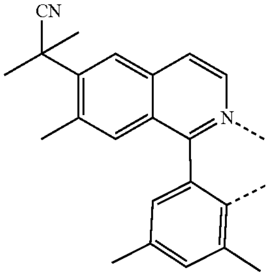
$L_{a-163}$
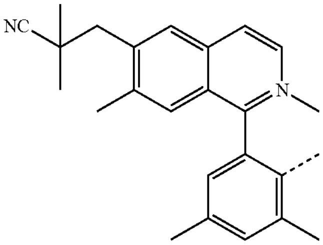
$L_{a-164}$
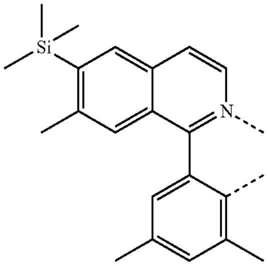
$L_{a-165}$
-continued
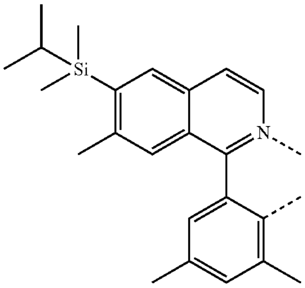
$L_{a-166}$
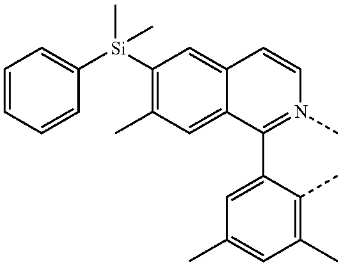
$L_{a-167}$
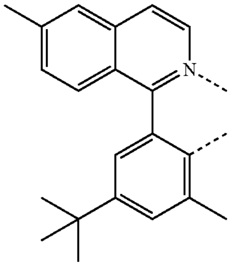
$L_{a-168}$
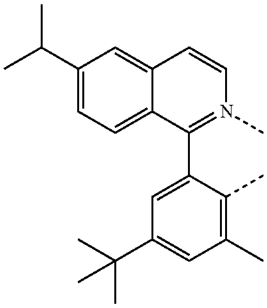
$L_{a-169}$
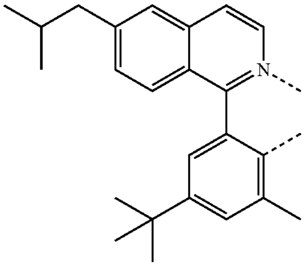
$L_{a-170}$ -continued
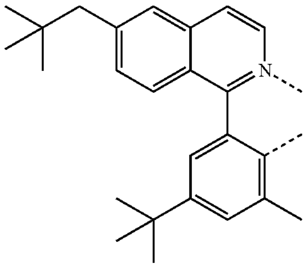
$L_{a\text{-}171}$
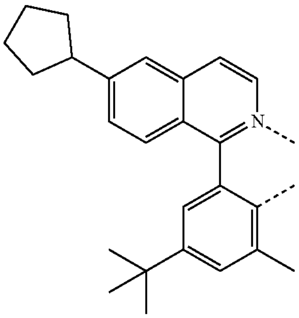
$L_{a\text{-}172}$
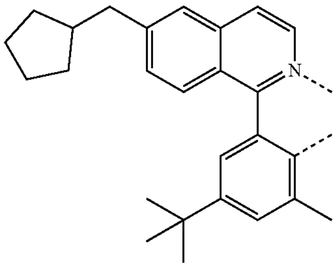
$L_{a\text{-}173}$
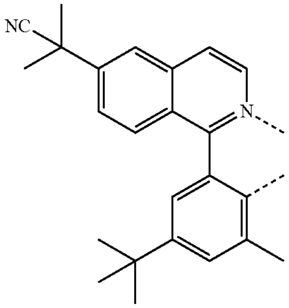
$L_{a\text{-}174}$
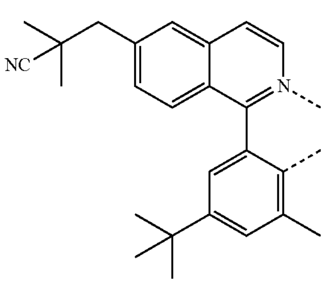
$L_{a\text{-}175}$
-continued
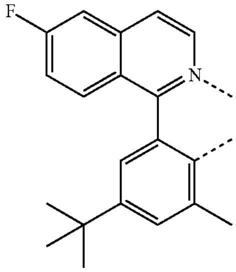
$L_{a\text{-}176}$
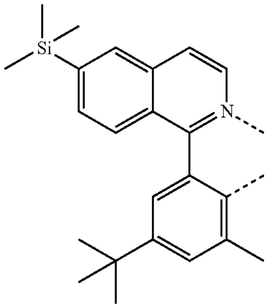
$L_{a\text{-}177}$
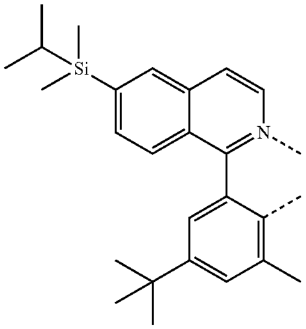
$L_{a\text{-}178}$
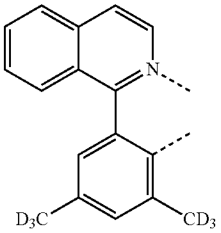
$L_{a\text{-}179}$
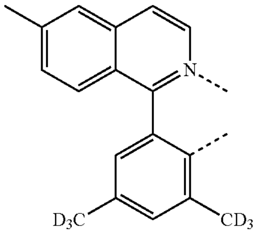
$L_{a\text{-}180}$

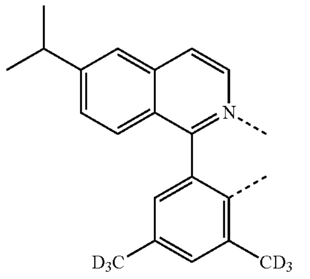
$L_{a-181}$
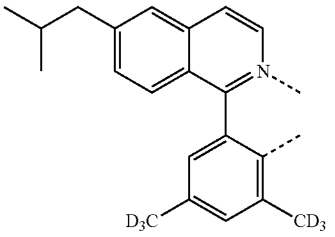
$L_{a-182}$
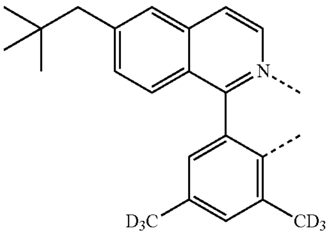
$L_{a-183}$
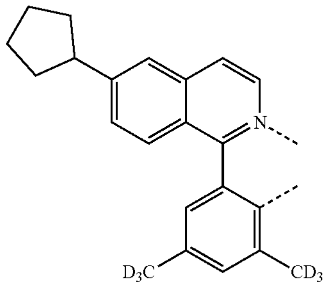
$L_{a-184}$
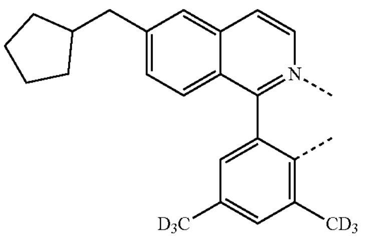
$L_{a-185}$
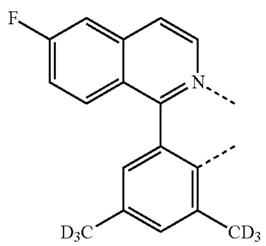
$L_{a-186}$
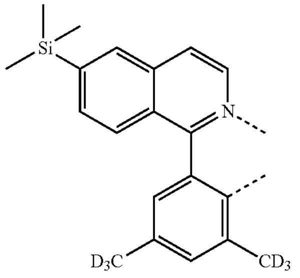
$L_{a-187}$
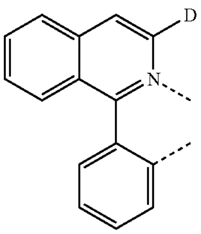
$L_{a-188}$
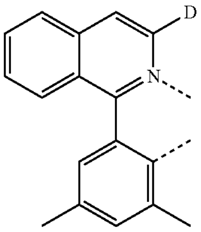
$L_{a-189}$
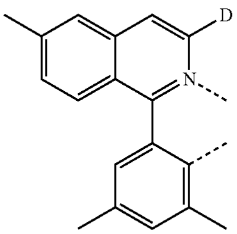
$L_{a-190}$
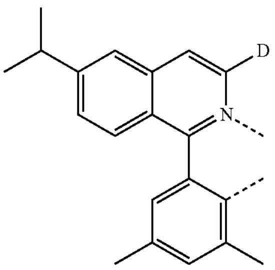
$L_{a-191}$
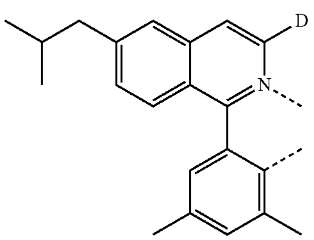
$L_{a-192}$ -continued
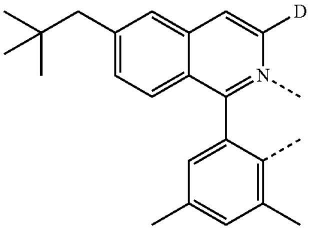
$L_{a\text{-}193}$
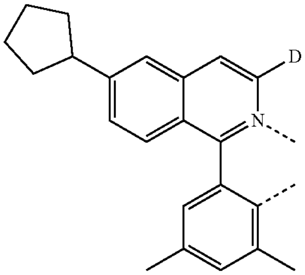
$L_{a\text{-}194}$
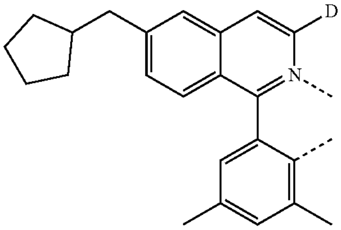
$L_{a\text{-}195}$
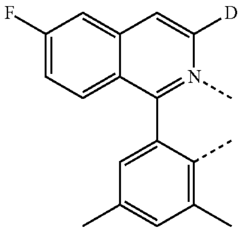
$L_{a\text{-}196}$
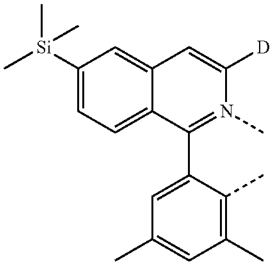
$L_{a\text{-}197}$
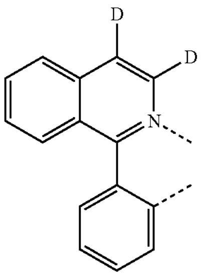
$L_{a\text{-}198}$
-continued
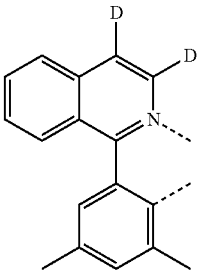
$L_{a\text{-}199}$
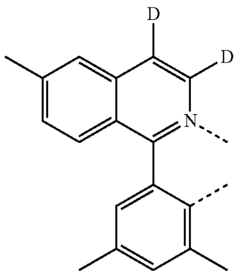
$L_{a\text{-}200}$
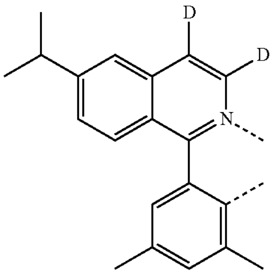
$L_{a\text{-}201}$
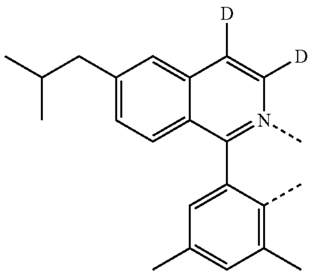
$L_{a\text{-}202}$
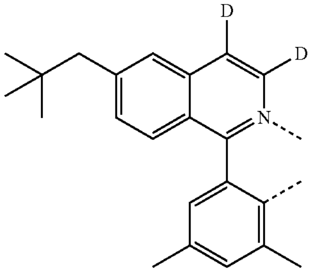
$L_{a\text{-}203}$ -continued
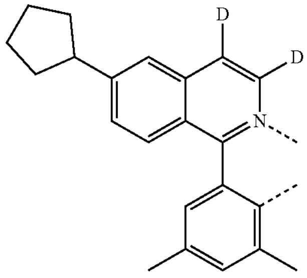
$L_{a\text{-}204}$
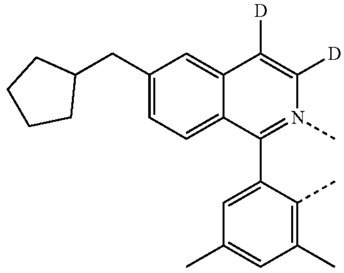
$L_{a\text{-}205}$
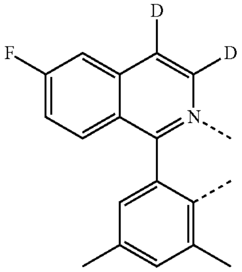
$L_{a\text{-}206}$
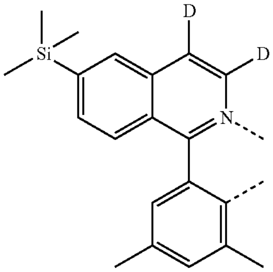
$L_{a\text{-}207}$
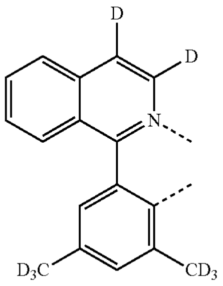
$L_{a\text{-}208}$
-continued
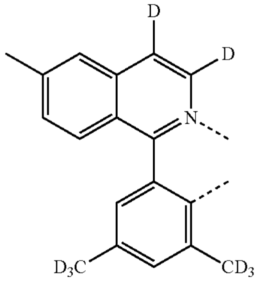
$L_{a\text{-}209}$
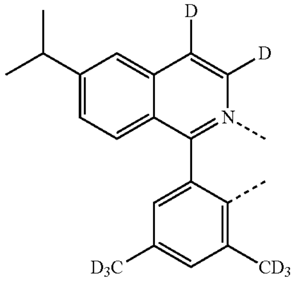
$L_{a\text{-}210}$
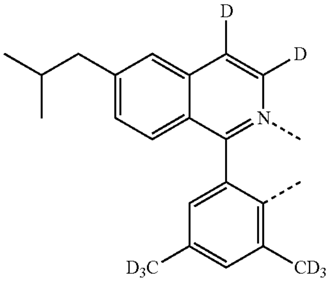
$L_{a\text{-}211}$
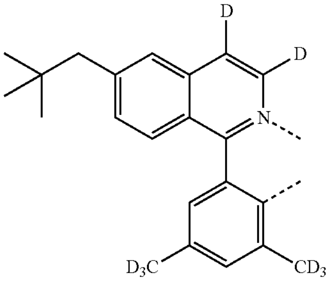
$L_{a\text{-}212}$
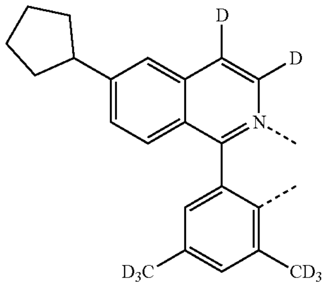
$L_{a\text{-}213}$ -continued
$L_{a-214}$
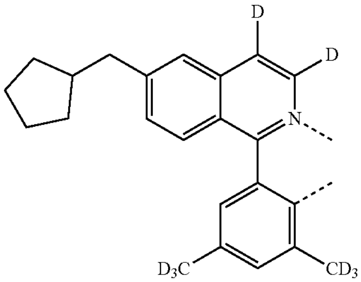
$L_{a-215}$
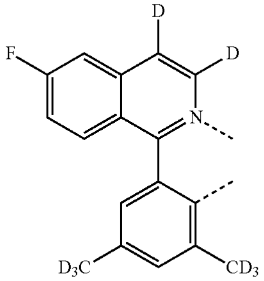
$L_{a-216}$
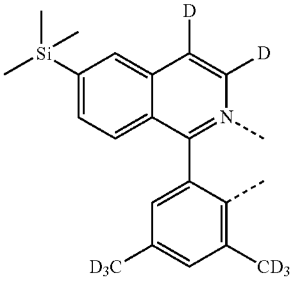
$L_{a-217}$
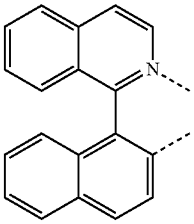
$L_{a-218}$
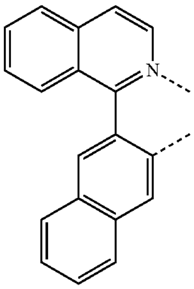
-continued
$L_{a-219}$
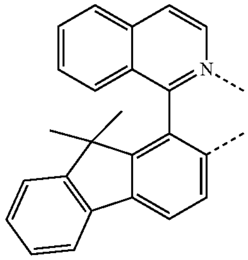
$L_{a-220}$
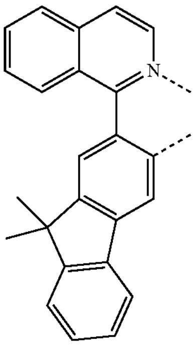
$L_{a-221}$
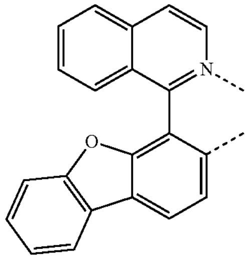
$L_{a-222}$
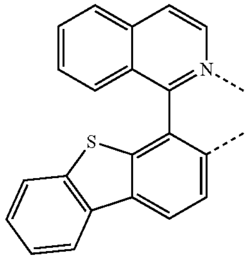
$L_{a-223}$
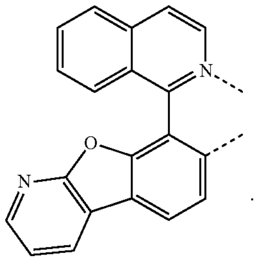

21. The electroluminescent device of claim 20, wherein the $L_b$ has a structure represented by Formula 4:

Formula 4

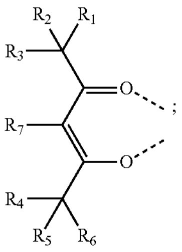

wherein $R_1$ to $R_7$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, a cyano group, and combinations thereof.

22. The electroluminescent device of claim 21, wherein at least two of $R_1$ to $R_3$ are, at each occurrence identically or differently, selected from substituted or unsubstituted alkyl having 2 to 20 carbon atoms, substituted or unsubstituted cycloalkyl having 3 to 20 ring carbon atoms or a combination thereof; and/or at least two of $R_4$ to $R_6$ are, at each occurrence identically or differently, selected from substituted or unsubstituted alkyl having 2 to 20 carbon atoms, substituted or unsubstituted cycloalkyl having 3 to 20 ring carbon atoms or a combination thereof.

23. The electroluminescent device of claim 20, wherein the $L_b$ is, at each occurrence identically or differently, selected from the group consisting of the following:

$L_{b1}$

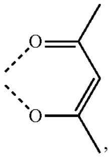

$L_{b2}$

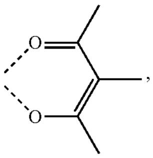

$L_{b3}$

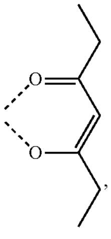

-continued $L_{b4}$

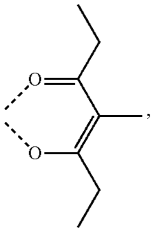

$L_{b5}$

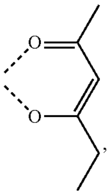

$L_{b6}$

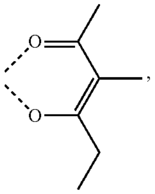

$L_{b7}$

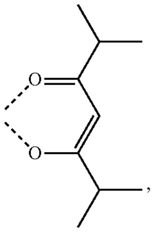

$L_{b8}$

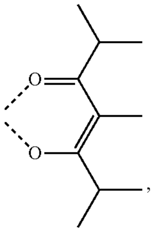

$L_{b9}$

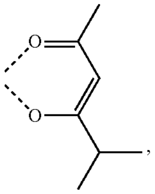

$L_{b10}$

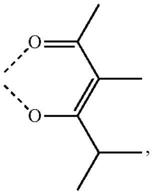

-continued
$L_{b11}$
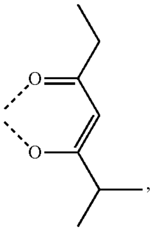
$L_{b12}$
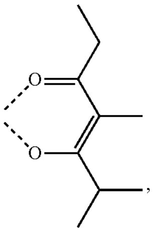
$L_{b13}$
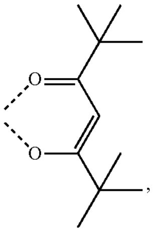
$L_{b14}$
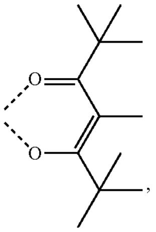
$L_{b15}$
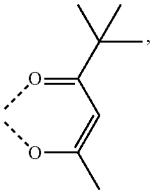
$L_{b16}$
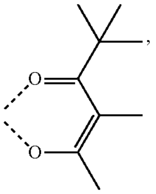
$L_{b17}$
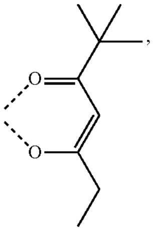
-continued
$L_{b18}$
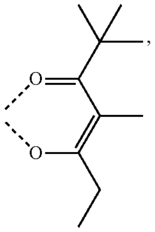
$L_{b19}$
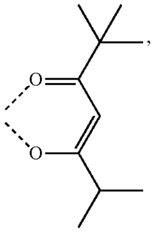
$L_{b20}$
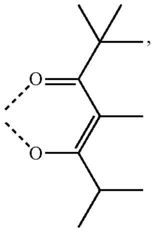
$L_{b21}$
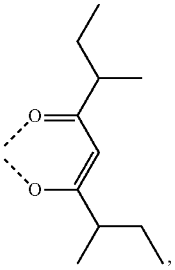
$L_{b22}$
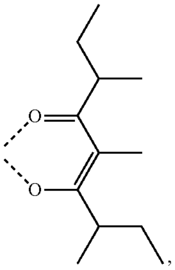
$L_{b23}$
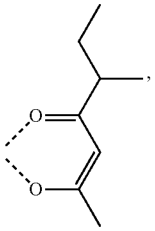

-continued
L$_{b24}$
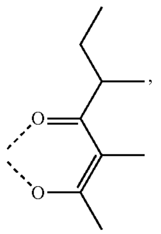
L$_{b25}$
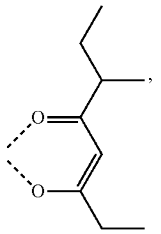
L$_{b26}$
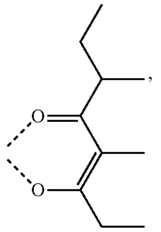
L$_{b27}$
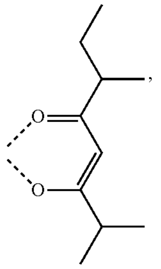
L$_{b28}$
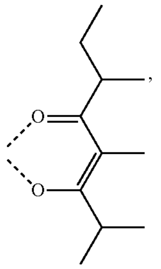
L$_{b29}$
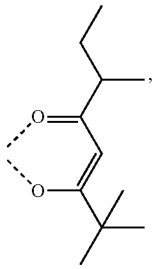
-continued
L$_{b30}$
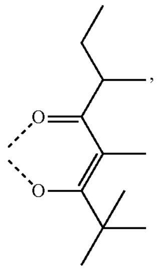
L$_{b31}$
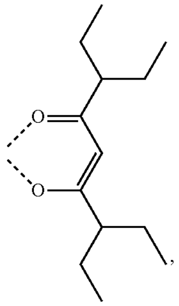
L$_{b32}$
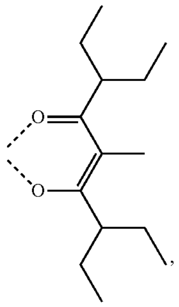
L$_{b33}$
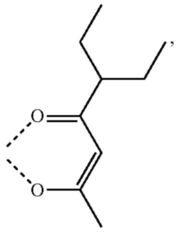
L$_{b34}$
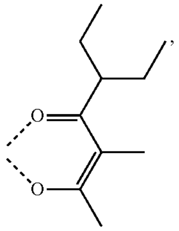
L$_{b35}$
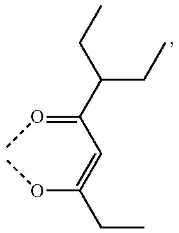

-continued
$L_{b36}$
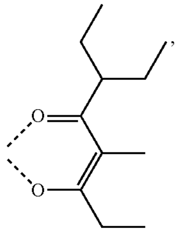
$L_{b37}$
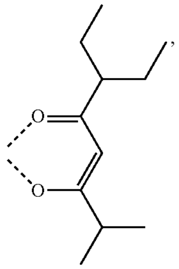
$L_{b38}$
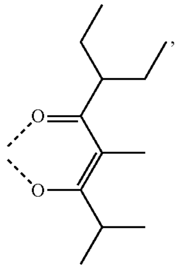
$L_{b39}$
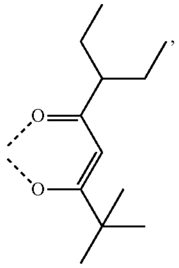
$L_{b40}$
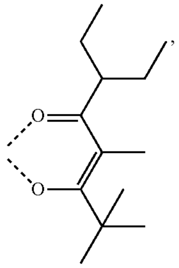
$L_{b41}$
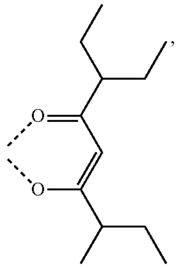
-continued
$L_{b42}$
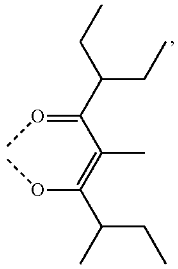
$L_{b43}$
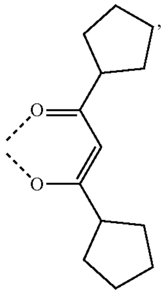
$L_{b44}$
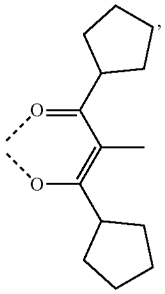
$L_{b45}$
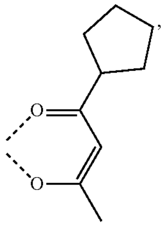
$L_{b46}$
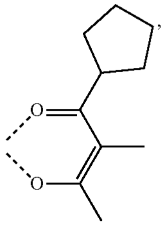
$L_{b47}$
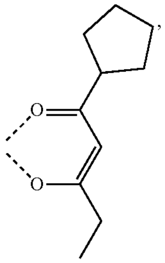

-continued
$L_{b48}$
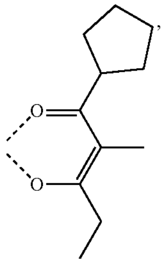
$L_{b49}$
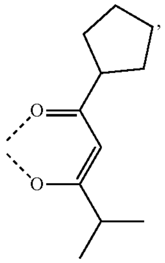
$L_{b50}$
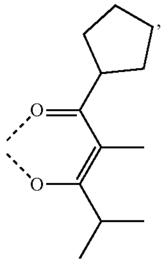
$L_{b51}$
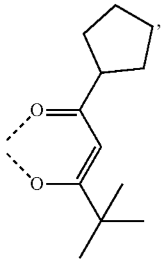
$L_{b52}$
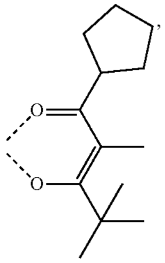
$L_{b53}$
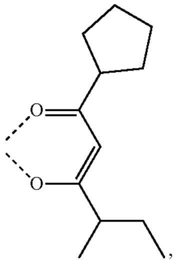
-continued
$L_{b54}$
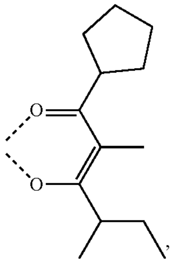
$L_{b55}$
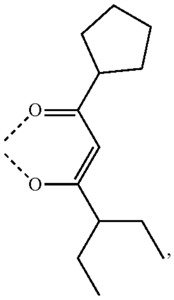
$L_{b56}$
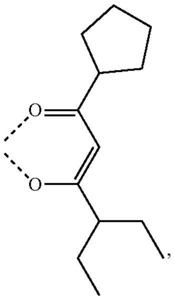
$L_{b57}$
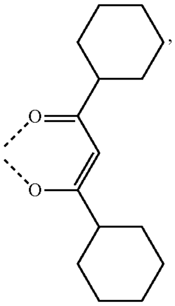
$L_{b58}$
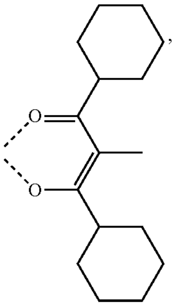

-continued
$L_{b59}$
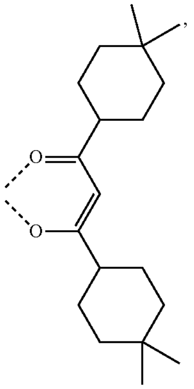
$L_{b60}$
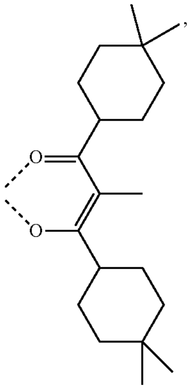
$L_{b61}$
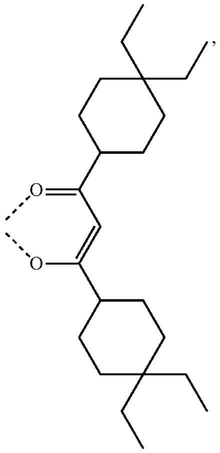
-continued
$L_{b62}$
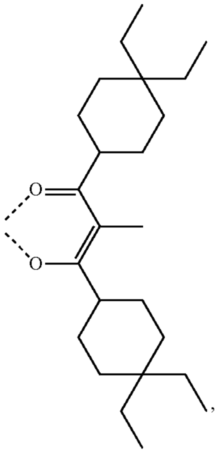
$L_{b63}$
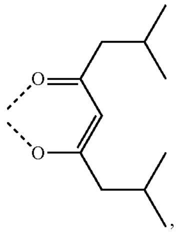
$L_{b64}$
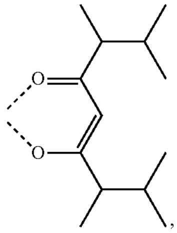
$L_{b65}$
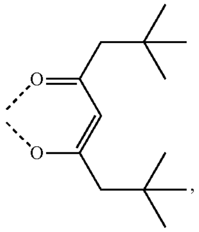
$L_{b66}$
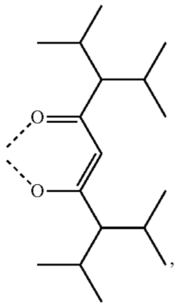

-continued
$L_{b67}$
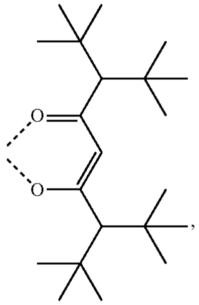
$L_{b68}$
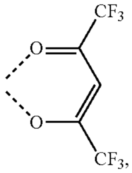
$L_{b69}$
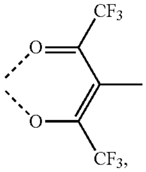
$L_{b70}$
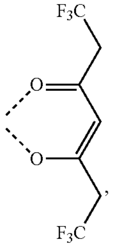
$L_{b71}$
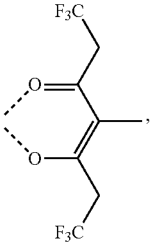
$L_{b72}$
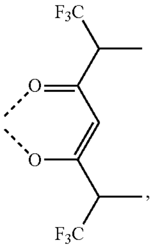
-continued
$L_{b73}$
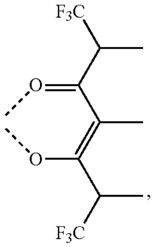
$L_{b74}$
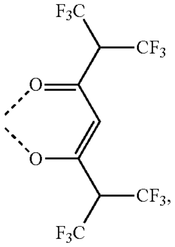
$L_{b75}$
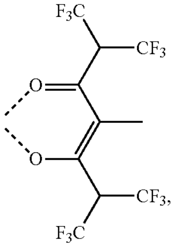
$L_{b76}$
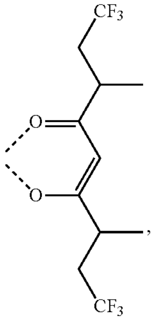
$L_{b77}$
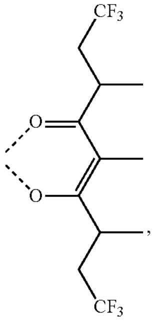

-continued
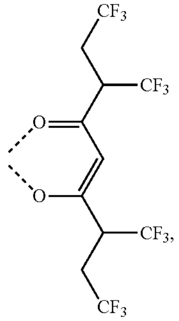
$L_{b78}$
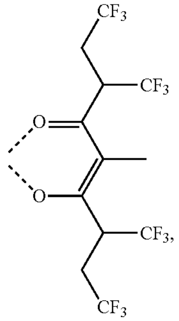
$L_{b79}$
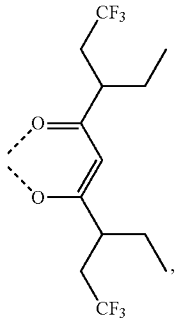
$L_{b80}$
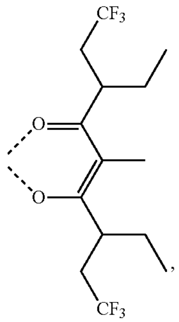
$L_{b81}$
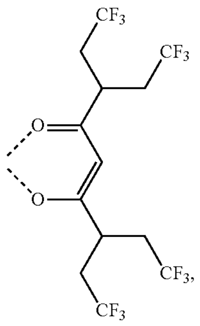
$L_{b82}$
-continued
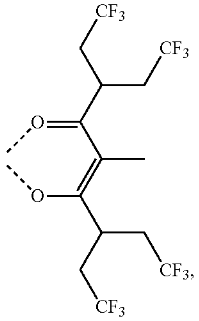
$L_{b83}$
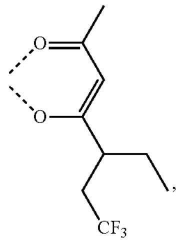
$L_{b84}$
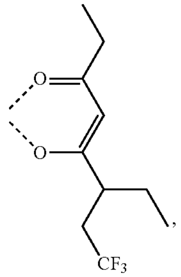
$L_{b85}$
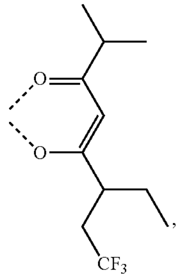
$L_{b86}$
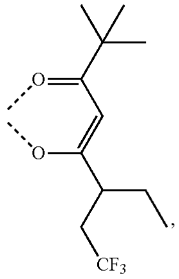
$L_{b87}$ -continued
$L_{b88}$
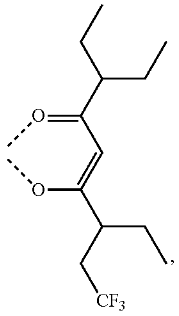
$L_{b89}$
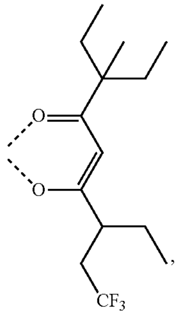
$L_{b90}$
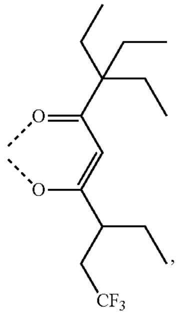
$L_{b91}$
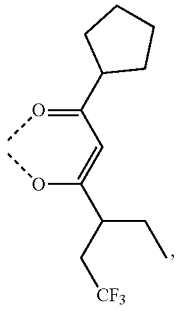
$L_{b92}$
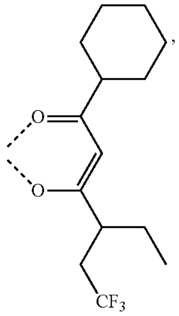
-continued
$L_{b93}$
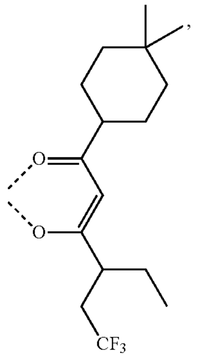
$L_{b94}$
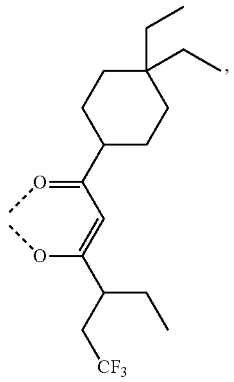
$L_{b95}$
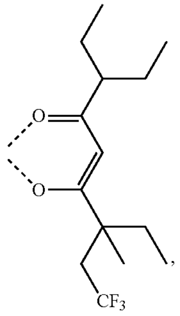
$L_{b96}$
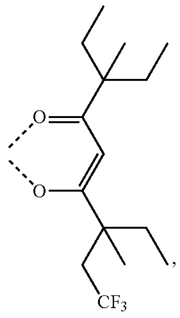

-continued
$L_{b97}$
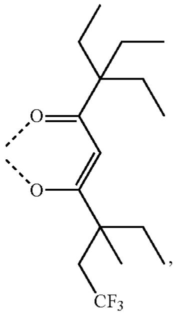
$L_{b98}$
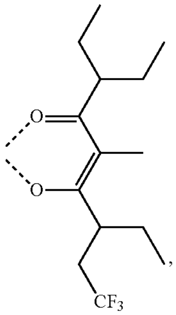
$L_{b99}$
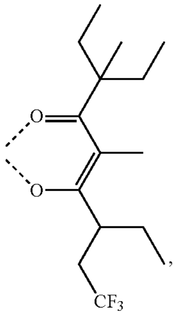
$L_{b100}$
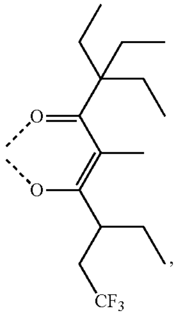
$L_{b101}$
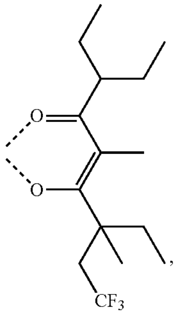
-continued
$L_{b102}$
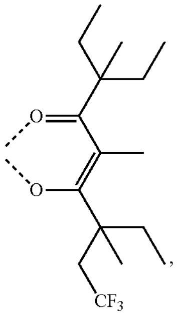
$L_{b103}$
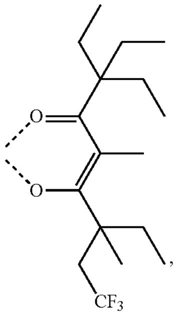
$L_{b104}$
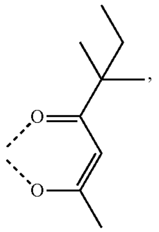
$L_{b105}$
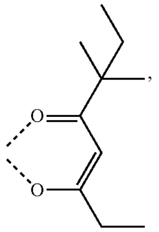
$L_{b106}$
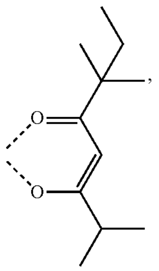

-continued
$L_{b107}$
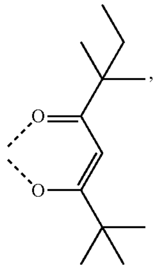
$L_{b108}$
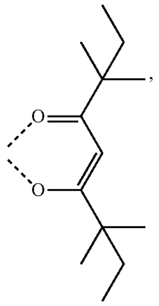
$L_{b109}$
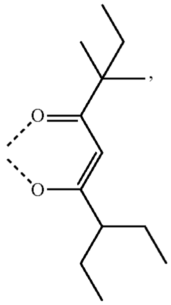
$L_{b110}$
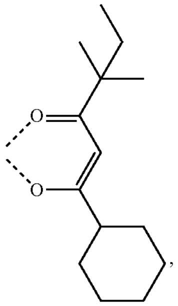
$L_{b111}$
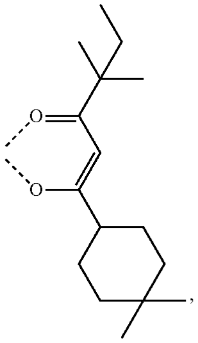
-continued
$L_{b112}$
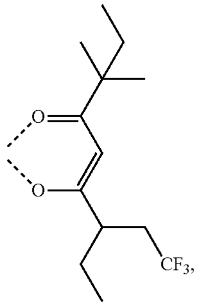
$L_{b113}$
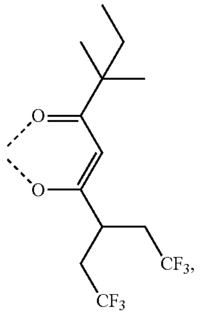
$L_{b114}$
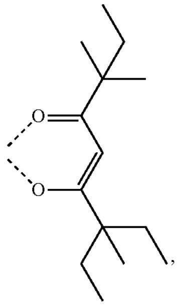
$L_{b115}$
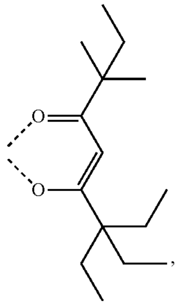
$L_{b116}$
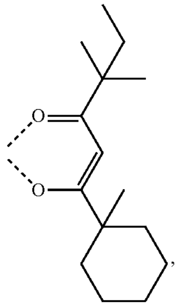

-continued
$L_{b117}$
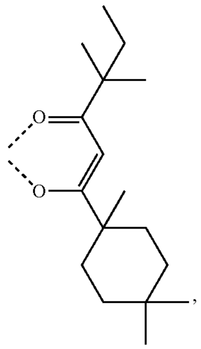
$L_{b118}$
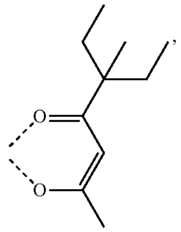
$L_{b119}$
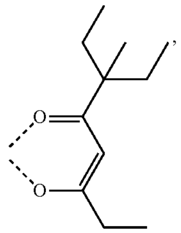
$L_{b120}$
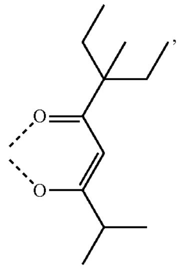
$L_{b121}$
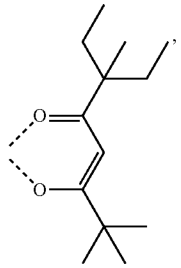
-continued
$L_{b122}$
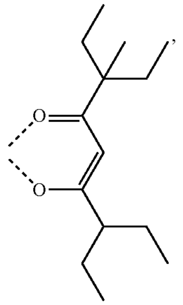
$L_{b123}$
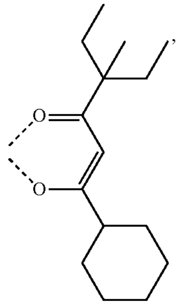
$L_{b124}$
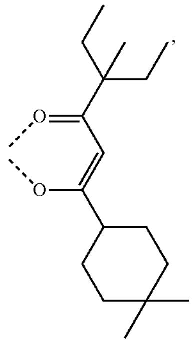
$L_{b125}$
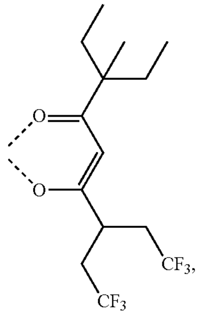
$L_{b126}$
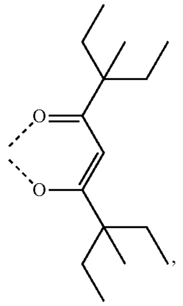

-continued
$L_{b127}$
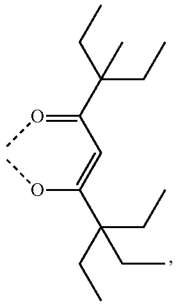
$L_{b128}$
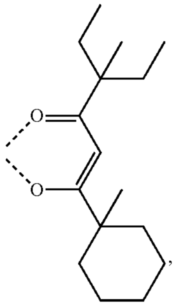
$L_{b129}$
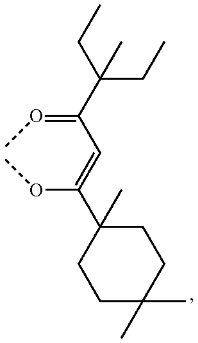
$L_{b130}$
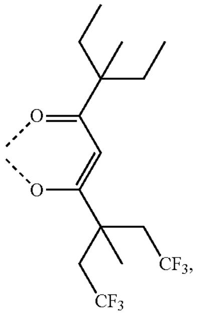
$L_{b131}$
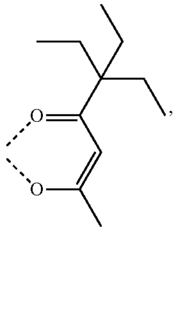
-continued
$L_{b132}$
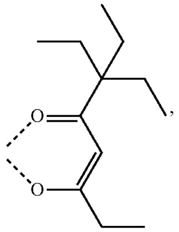
$L_{b133}$
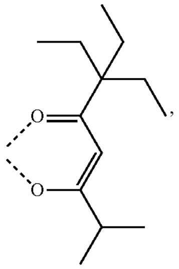
$L_{b134}$
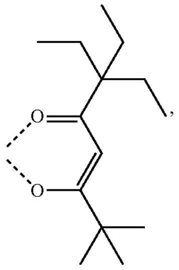
$L_{b135}$
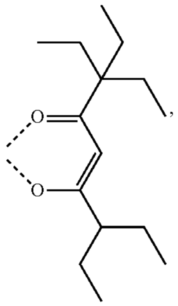
$L_{b136}$
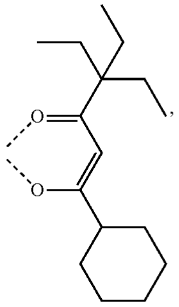

-continued
$L_{b137}$
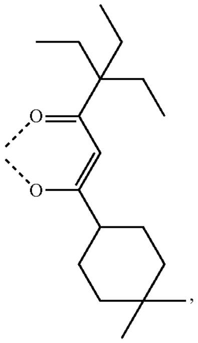
$L_{b138}$
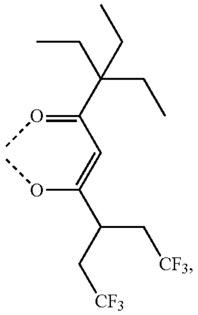
$L_{b139}$
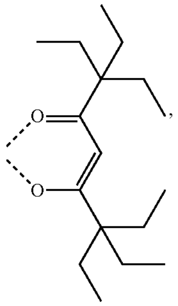
$L_{b140}$
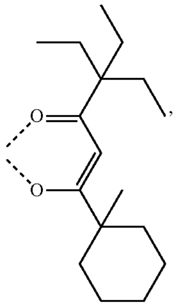
-continued
$L_{b141}$
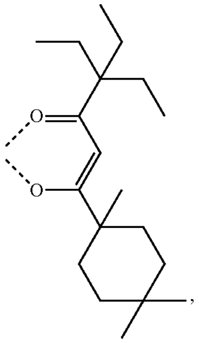
$L_{b142}$
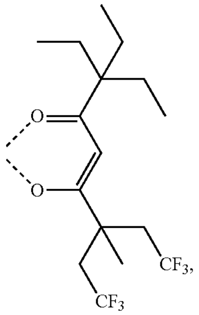
$L_{b143}$
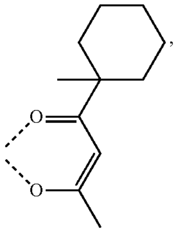
$L_{b144}$
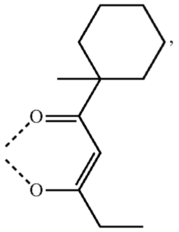
$L_{b145}$
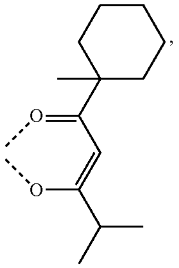

-continued
$L_{b146}$
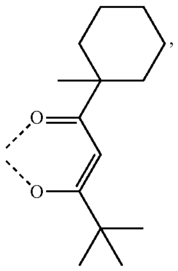
$L_{b147}$
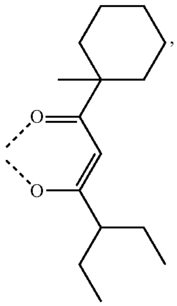
$L_{b148}$
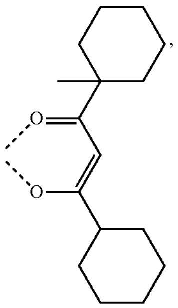
$L_{b149}$
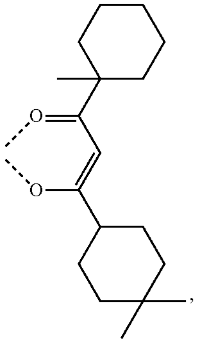
$L_{b150}$
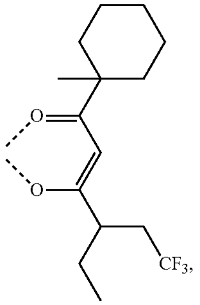
-continued
$L_{b151}$
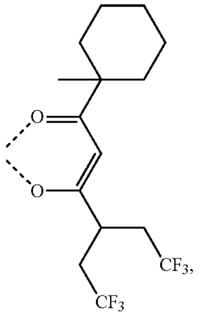
$L_{b152}$
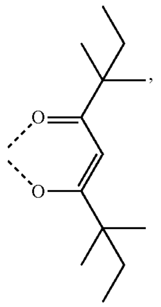
$L_{b153}$
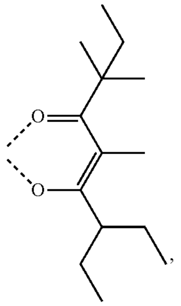
$L_{b154}$
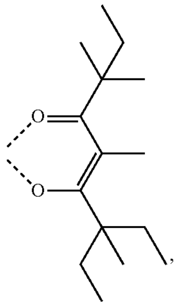
$L_{b155}$
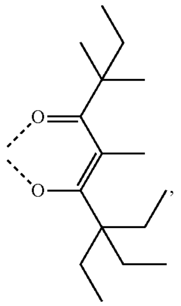

-continued
L$_{b156}$
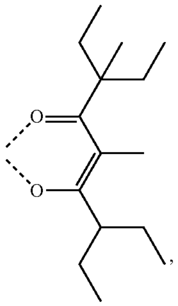
L$_{b157}$
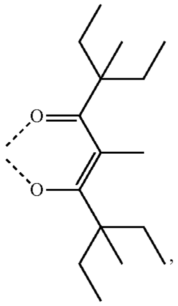
L$_{b158}$
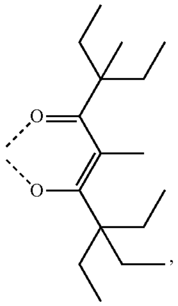
L$_{b159}$
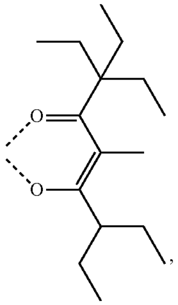
L$_{b160}$
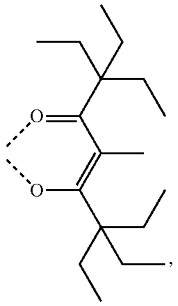
-continued
L$_{b161}$
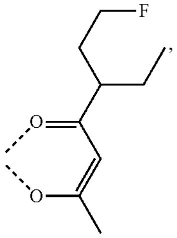
L$_{b162}$
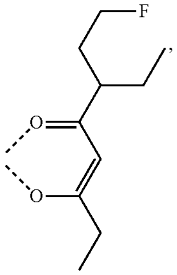
L$_{b163}$
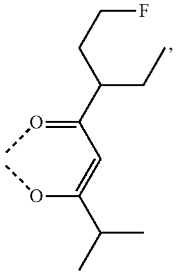
L$_{b164}$
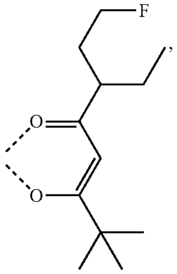
L$_{b165}$
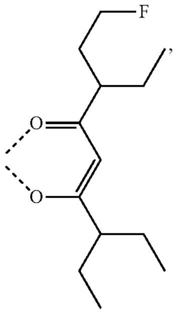

-continued
$L_{b166}$
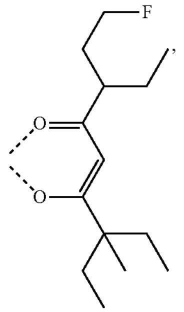
$L_{b167}$
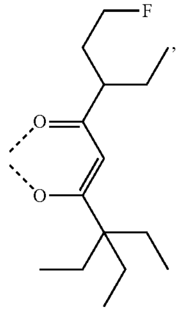
$L_{b168}$
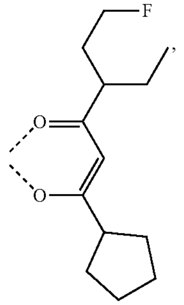
$L_{b169}$
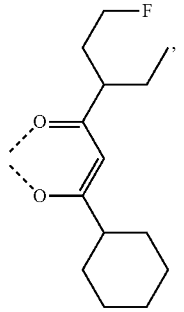
$L_{b170}$
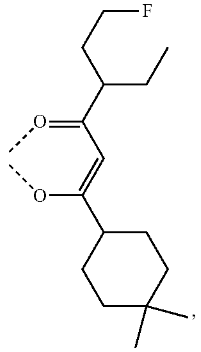
-continued
$L_{b171}$
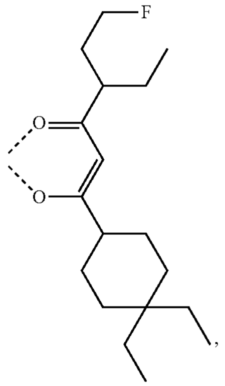
$L_{b172}$
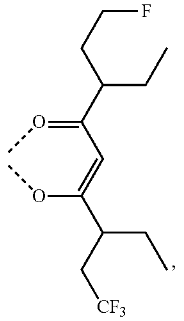
$L_{b173}$
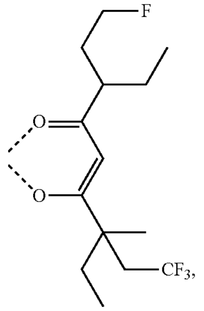
$L_{b174}$
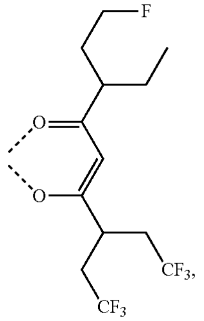

-continued
$L_{b175}$
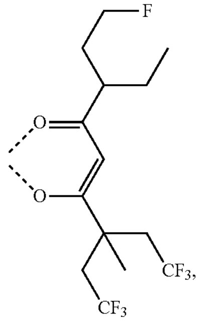
$L_{b176}$
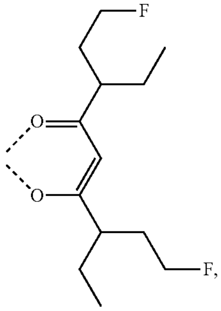
$L_{b177}$
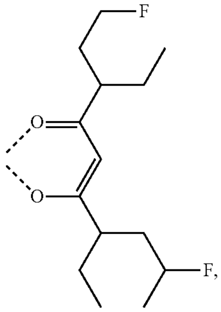
$L_{b178}$
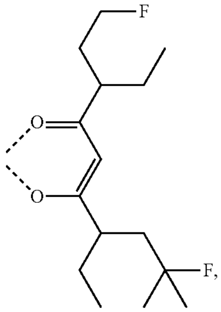
$L_{b179}$
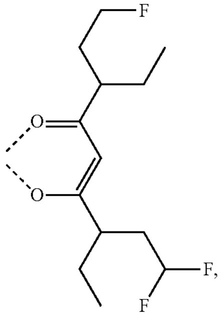
-continued
$L_{b180}$
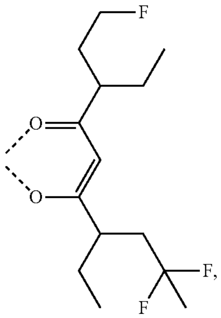
$L_{b181}$
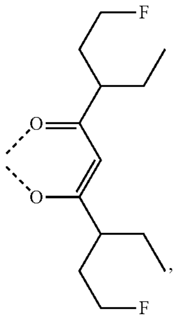
$L_{b182}$
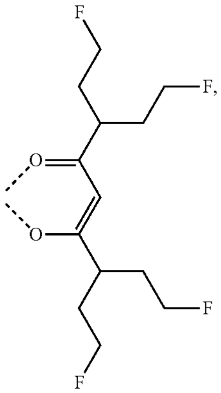
$L_{b183}$
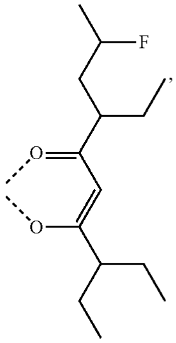

$L_{b184}$
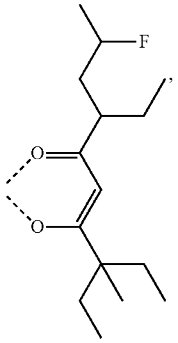
,
$L_{b185}$
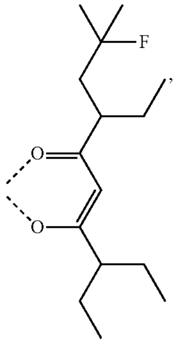
,
$L_{b186}$
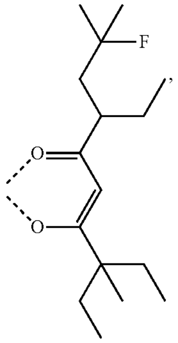
,
$L_{b187}$
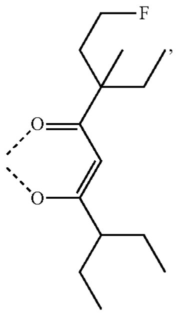
,
$L_{b188}$
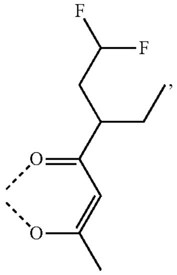
,
$L_{b189}$
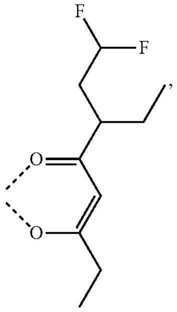
,
$L_{b190}$
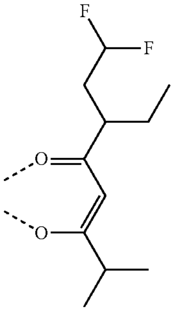
,
$L_{b191}$
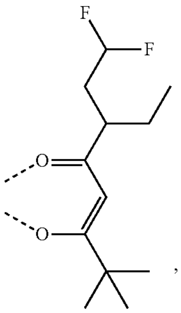
,

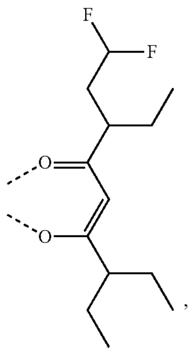
$L_{b192}$
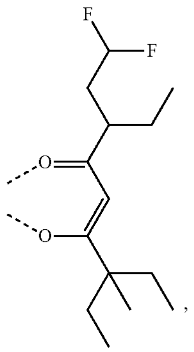
$L_{b193}$
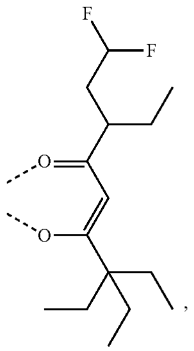
$L_{b194}$
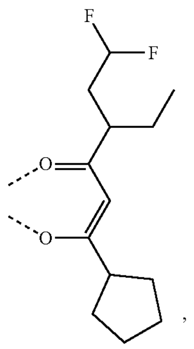
$L_{b195}$
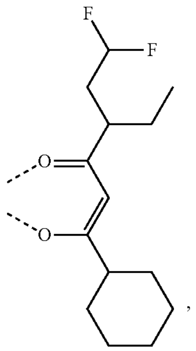
$L_{b196}$
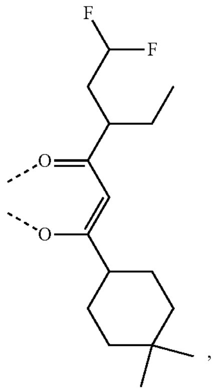
$L_{b197}$
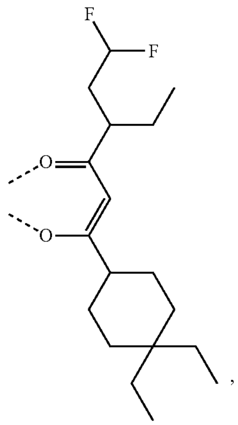
$L_{b198}$
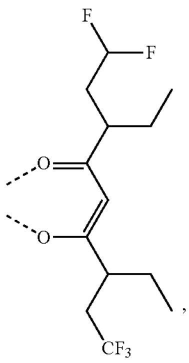
$L_{b199}$ 204
-continued
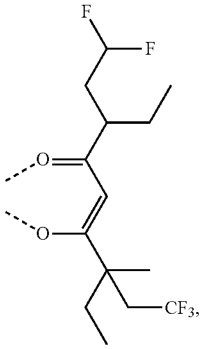
$L_{b200}$
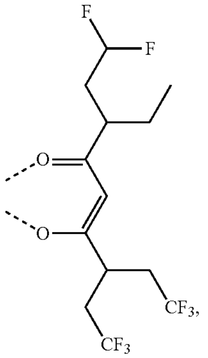
$L_{b201}$
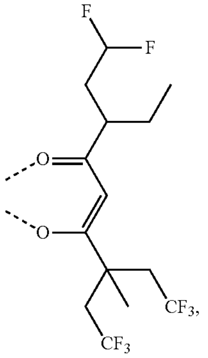
$L_{b202}$
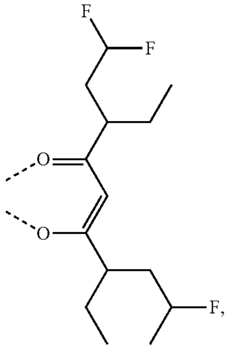
$L_{b203}$
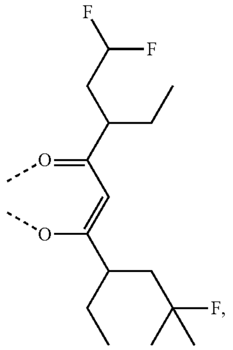
$L_{b204}$
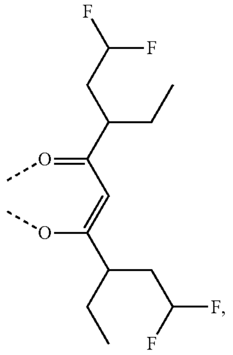
$L_{b205}$
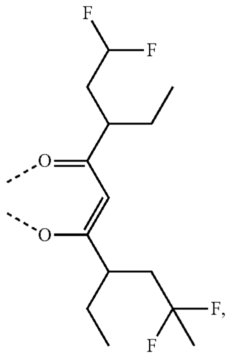
$L_{b206}$
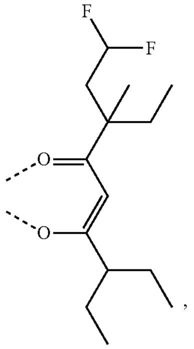
$L_{b207}$ -continued
$L_{b208}$
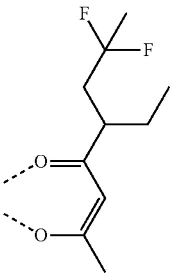
,
$L_{b209}$
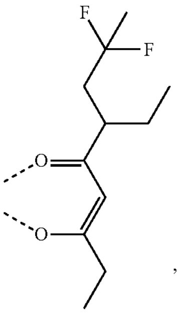
,
$L_{b210}$
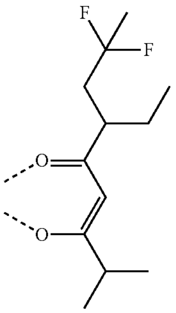
,
$L_{b211}$
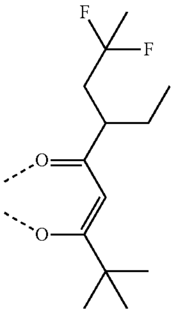
,
$L_{b212}$
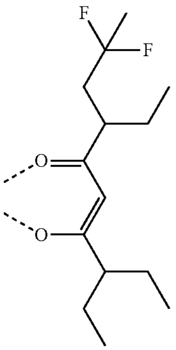
,
-continued
$L_{b213}$
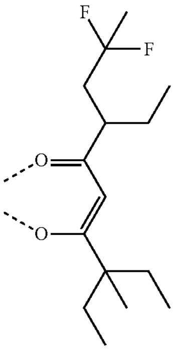
,
$L_{b214}$
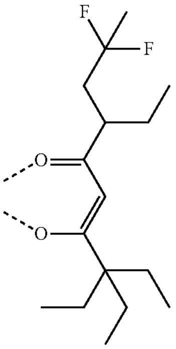
,
$L_{b215}$
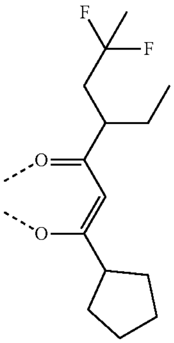
,
$L_{b216}$
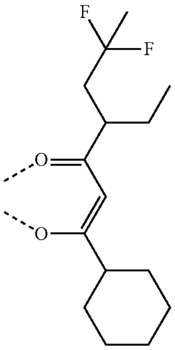

-continued
Lb217
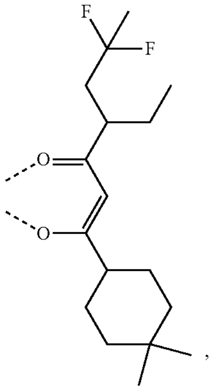
Lb218
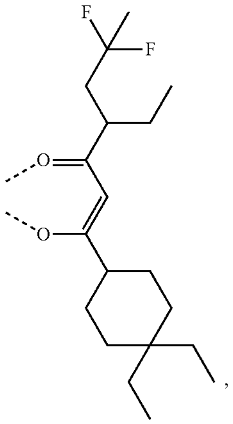
Lb219
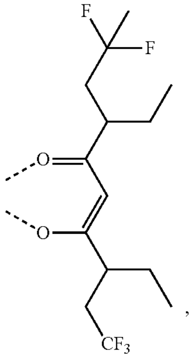
Lb220
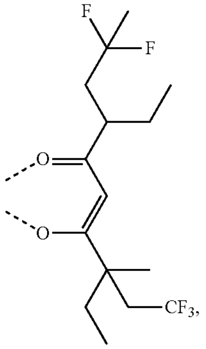
-continued
Lb221
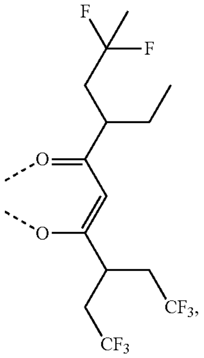
Lb222
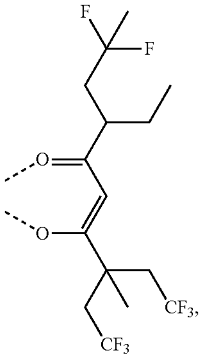
Lb223
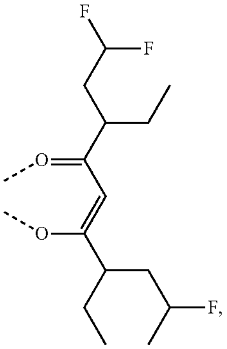
Lb224
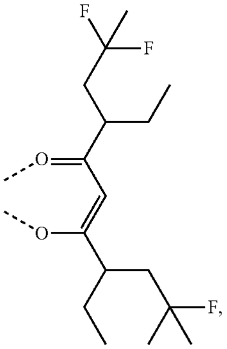

-continued
$L_{b225}$
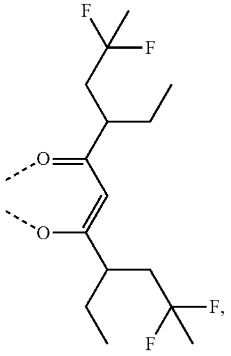
$L_{b226}$
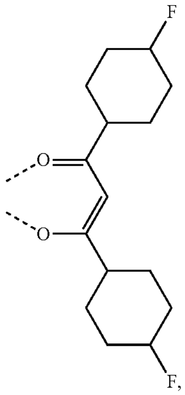
$L_{b227}$
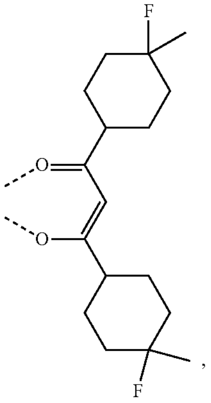
$L_{b228}$
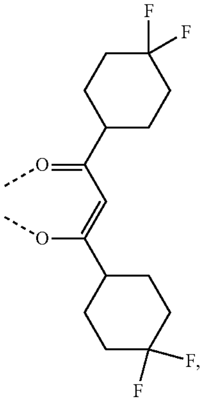
-continued
$L_{b229}$
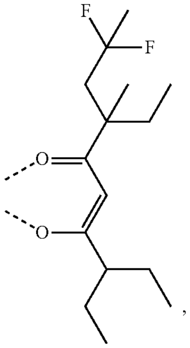
$L_{b230}$
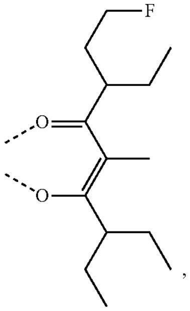
$L_{b231}$
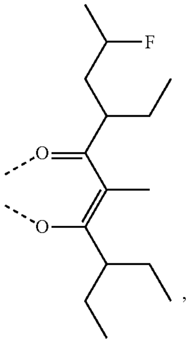
$L_{b232}$
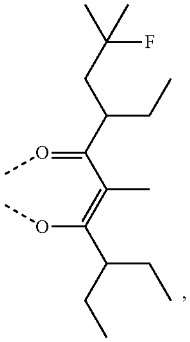

-continued
$L_{b233}$
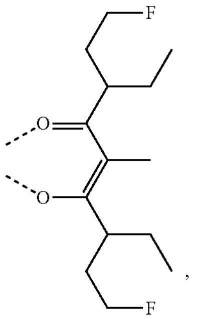
$L_{b234}$
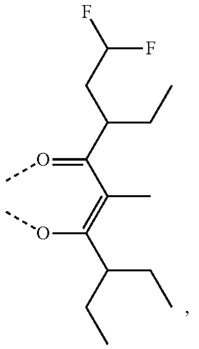
$L_{b235}$
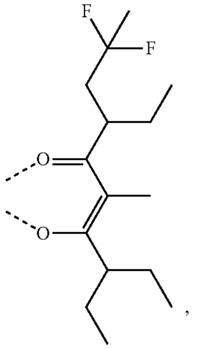
$L_{b236}$
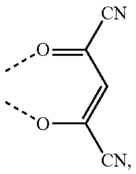
$L_{b237}$
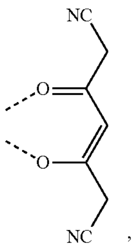
-continued
$L_{b238}$
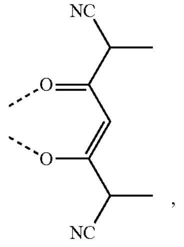
$L_{b239}$
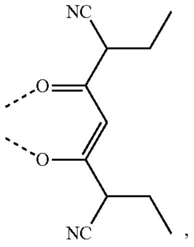
$L_{b240}$
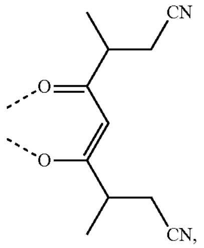
$L_{b241}$
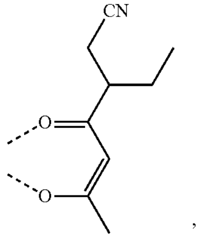
$L_{b242}$
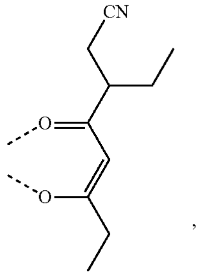
$L_{b243}$
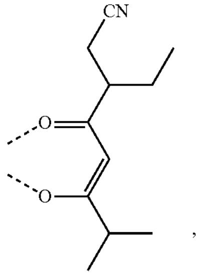

$L_{b244}$
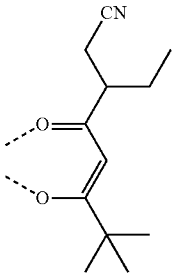
,
$L_{b245}$
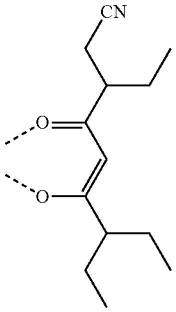
,
$L_{b246}$
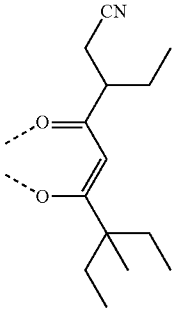
,
$L_{b247}$
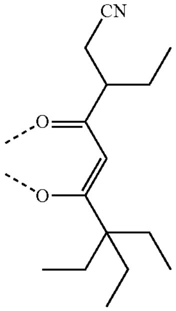
,
$L_{b248}$
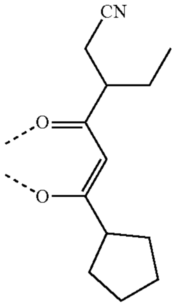
,
$L_{b249}$
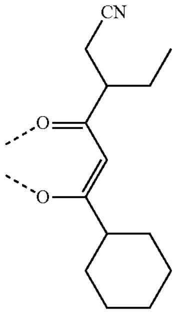
,
$L_{b250}$
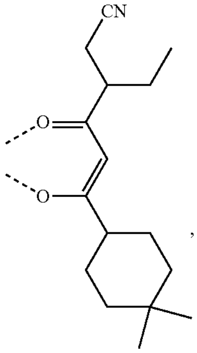
,
$L_{b251}$
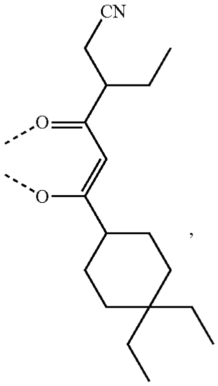
,
$L_{b252}$
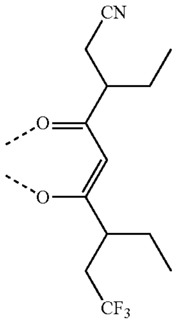
, -continued
$L_{b253}$
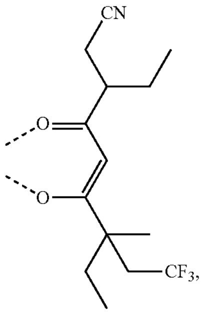
$L_{b254}$
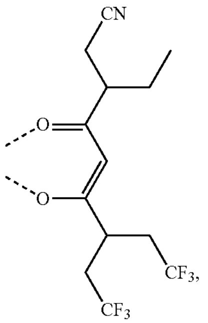
$L_{b255}$
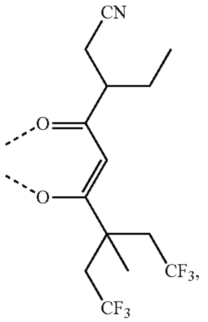
$L_{b256}$
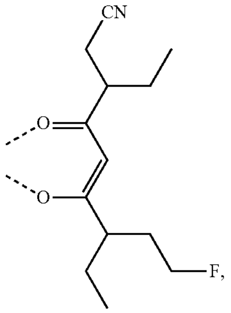
$L_{b257}$
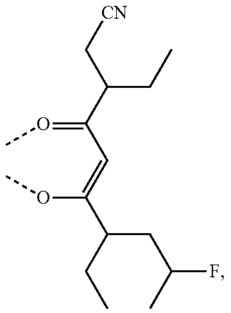
-continued
$L_{b258}$
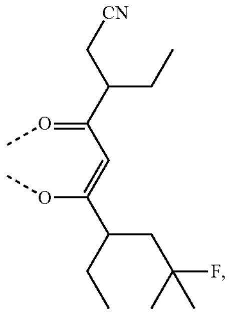
$L_{b259}$
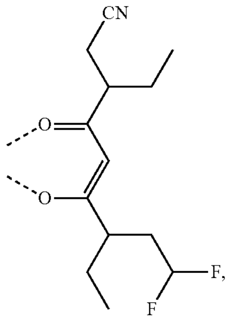
$L_{b260}$
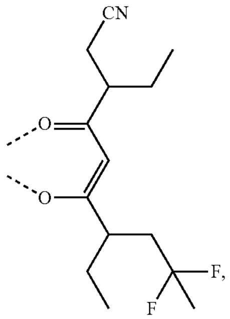
$L_{b261}$
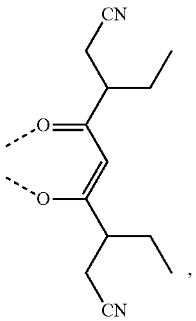
$L_{b262}$
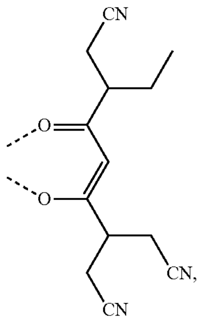

-continued
$L_{b263}$
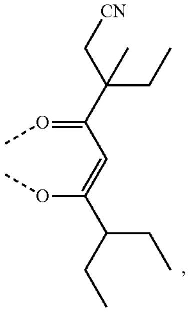
$L_{b264}$
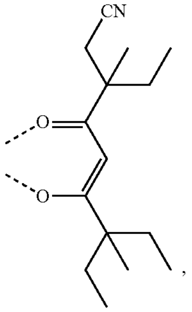
$L_{b265}$
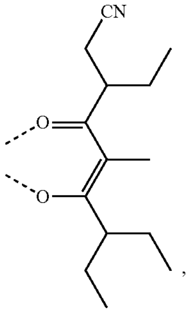
$L_{b266}$
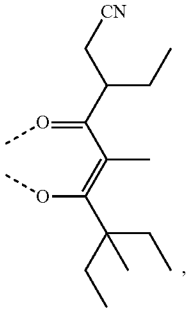
$L_{b267}$
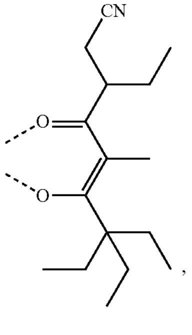
-continued
$L_{b268}$
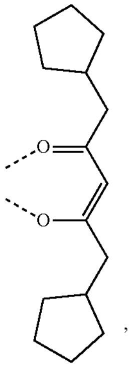
$L_{b269}$
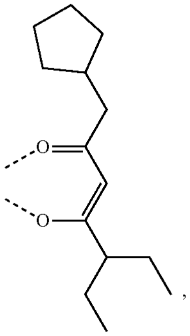
$L_{b270}$
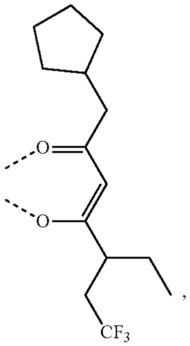
$L_{b271}$
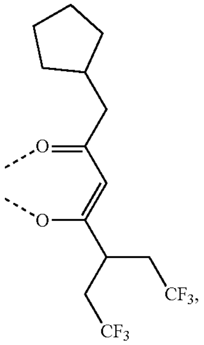

-continued
L$_{b272}$
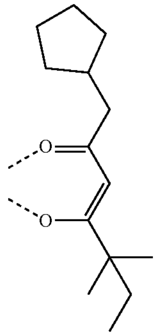
,
L$_{b273}$
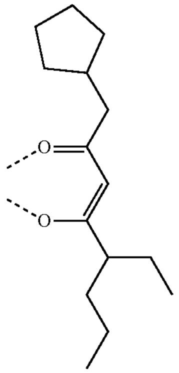
,
L$_{b274}$
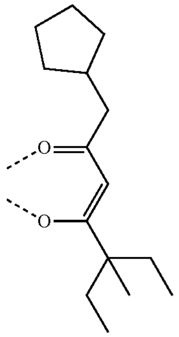
,
L$_{b275}$
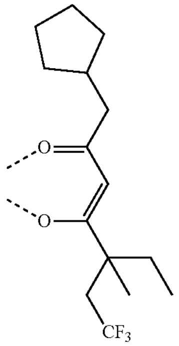
,
L$_{b276}$
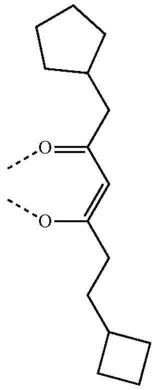
,
L$_{b277}$
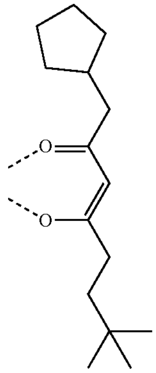
,
L$_{b278}$
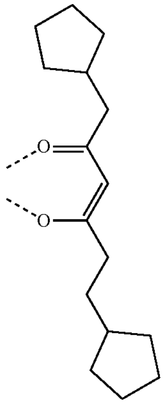
,
L$_{b279}$
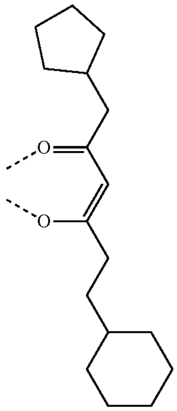
, -continued
$L_{b280}$
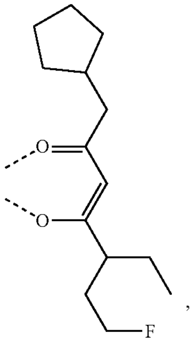
$L_{b281}$
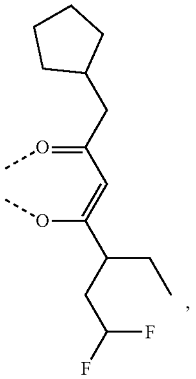
$L_{b282}$
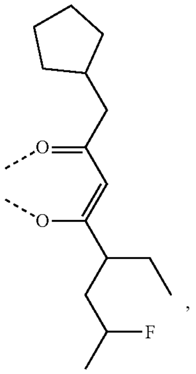
$L_{b283}$
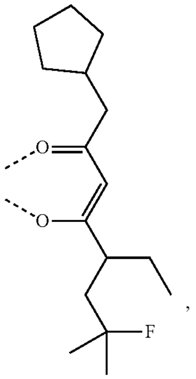
-continued
$L_{b284}$
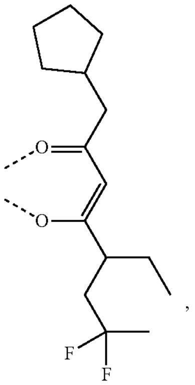
$L_{b285}$
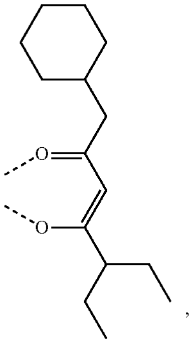
$L_{b286}$
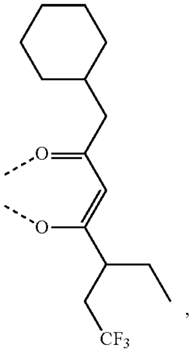
$L_{b287}$
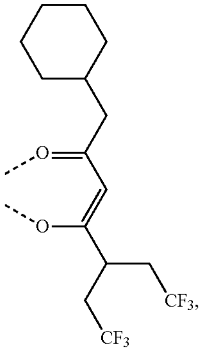

-continued
$L_{b288}$
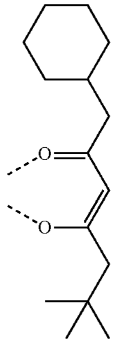
,
$L_{b289}$
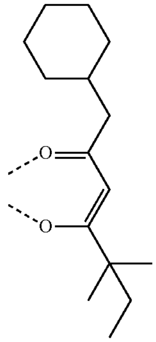
,
$L_{b290}$
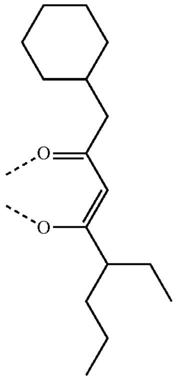
,
$L_{b291}$
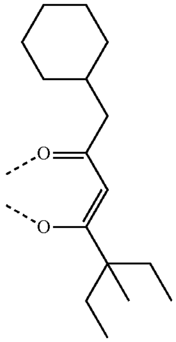
,
-continued
$L_{b292}$
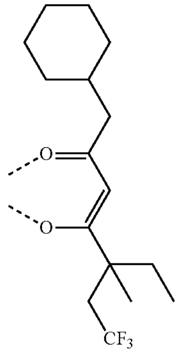
,
$L_{b293}$
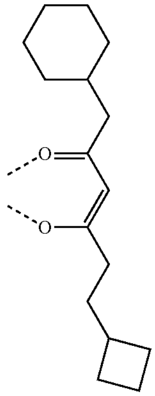
,
$L_{b294}$
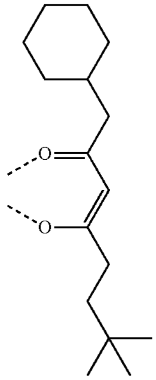
,
$L_{b295}$
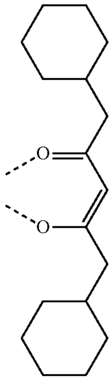
, -continued
L$_{b296}$
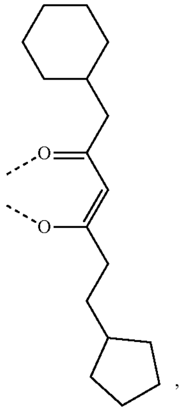
L$_{b297}$
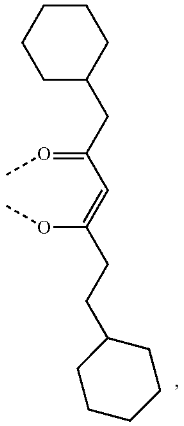
L$_{b298}$
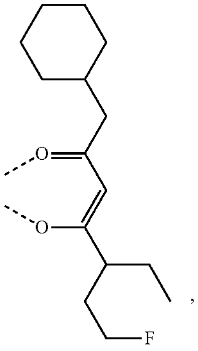
L$_{b299}$
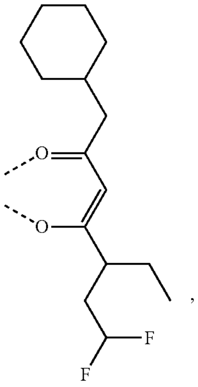
-continued
L$_{b300}$
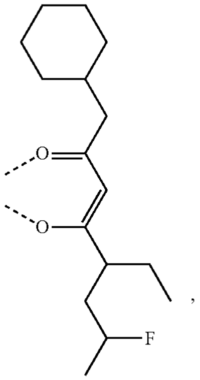
L$_{b301}$
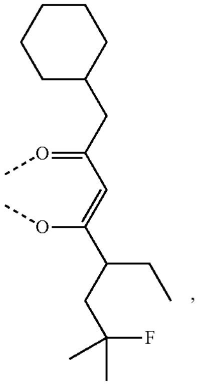
L$_{b302}$
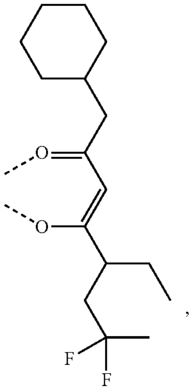
L$_{b303}$
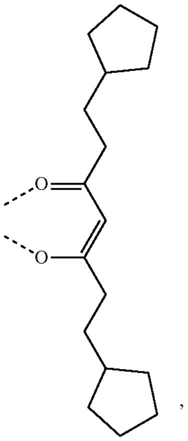

-continued
$L_{b304}$
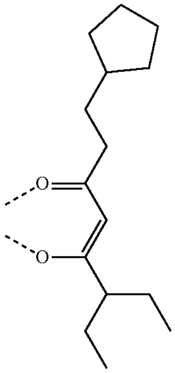
,
$L_{b305}$
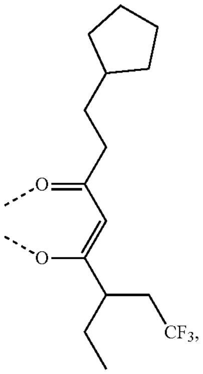
$L_{b306}$
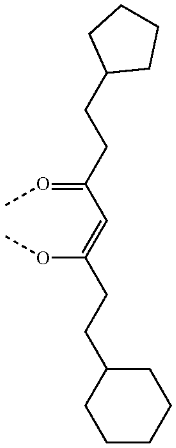
,
$L_{b307}$
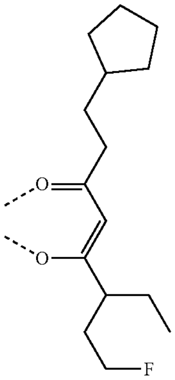
,
-continued
$L_{b308}$
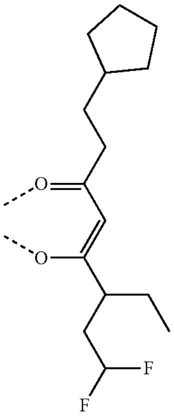
,
$L_{b309}$
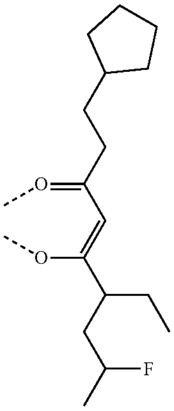
,
$L_{b310}$
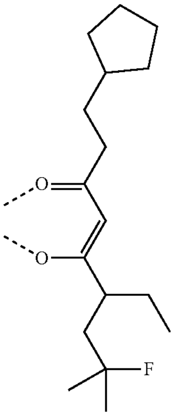
, L$_{b311}$
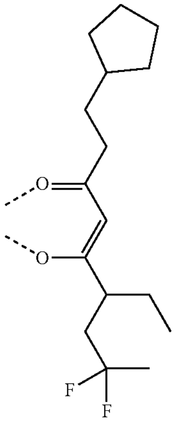
,
L$_{b312}$
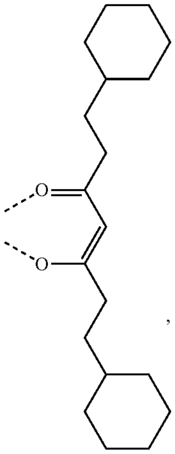
,
L$_{b313}$
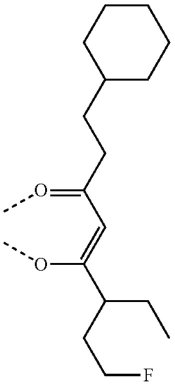
,
L$_{b314}$
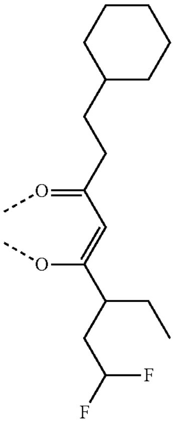
,
L$_{b315}$
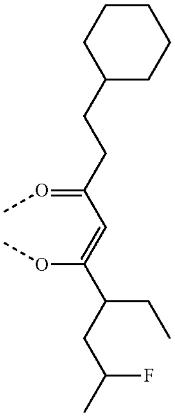
,
L$_{b316}$
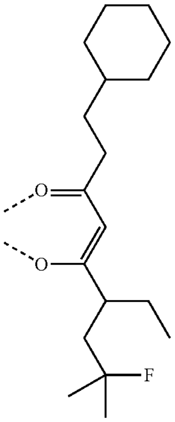
, -continued $L_{b317}$

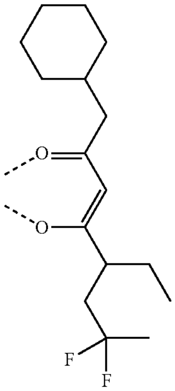

, $L_{b318}$

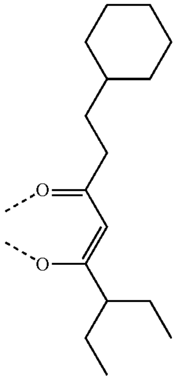

, $L_{b319}$

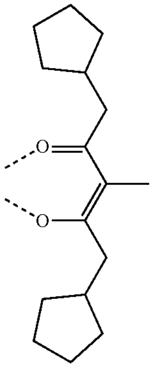

, $L_{b320}$

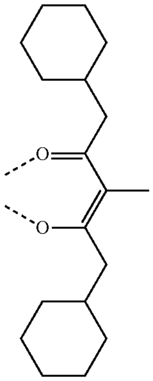

,

-continued $L_{b321}$

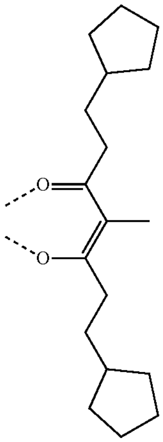

.

$L_{b322}$

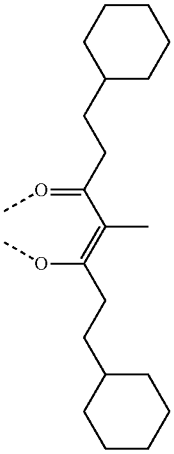

,

24. The electroluminescent device of claim 23, wherein the second compound is selected from the group consisting of Compound 2-1 to Compound 2-2, Compound 2-5 to Compound 2-26, Compound 2-41 to Compound 2-62, Compound 2-77 to Compound 2-98, Compound 2-113 to Compound 2-134, Compound 2-149 to Compound 2-170, Compound 2-185 to Compound 2-206, Compound 2-217 to Compound 2-223, Compound 2-229 to Compound 2-237, Compound 2-243 to Compound 2-251, Compound 2-257 to Compound 2-265, Compound 2-271 to Compound 2-279, Compound 2-285 to Compound 2-293 and Compound 2-299 to Compound 2-300;

wherein, the Compound 2-1 to Compound 2-2, Compound 2-5 to Compound 2-26, Compound 2-41 to Compound 2-62, Compound 2-77 to Compound 2-98, Compound 2-113 to Compound 2-134, Compound 2-149 to Compound 2-170, Compound 2-185 to Compound 2-206 have the structure of $Ir(L_a)_2(L_b)$, wherein the two $L_a$ are the same, and the $L_a$ and $L_b$ are respectively selected from structures listed in the following table:

| Compound No. | $L_a$ | $L_b$ | Compound No. | $L_a$ | $L_b$ |
|---|---|---|---|---|---|
| 2-1 | $L_{a\text{-}36}$ | $L_{b1}$ | 2-2 | $L_{a\text{-}133}$ | $L_{b1}$ |
| 2-5 | $L_{a\text{-}36}$ | $L_{b31}$ | 2-6 | $L_{a\text{-}37}$ | $L_{b31}$ |

-continued

| Compound No. | $L_a$ | $L_b$ | Compound No. | $L_a$ | $L_b$ |
|---|---|---|---|---|---|
| 2-7 | $L_{a-41}$ | $L_{b31}$ | 2-8 | $L_{a-43}$ | $L_{b31}$ |
| 2-9 | $L_{a-45}$ | $L_{b31}$ | 2-10 | $L_{a-53}$ | $L_{b31}$ |
| 2-11 | $L_{a-57}$ | $L_{b31}$ | 2-12 | $L_{a-72}$ | $L_{b31}$ |
| 2-13 | $L_{a-119}$ | $L_{b31}$ | 2-14 | $L_{a-128}$ | $L_{b31}$ |
| 2-15 | $L_{a-129}$ | $L_{b31}$ | 2-16 | $L_{a-130}$ | $L_{b31}$ |
| 2-17 | $L_{a-133}$ | $L_{b31}$ | 2-18 | $L_{a-136}$ | $L_{b31}$ |
| 2-19 | $L_{a-137}$ | $L_{b31}$ | 2-20 | $L_{a-141}$ | $L_{b31}$ |
| 2-21 | $L_{a-146}$ | $L_{b31}$ | 2-22 | $L_{a-181}$ | $L_{b31}$ |
| 2-23 | $L_{a-194}$ | $L_{b31}$ | 2-24 | $L_{a-195}$ | $L_{b31}$ |
| 2-25 | $L_{a-204}$ | $L_{b31}$ | 2-26 | $L_{a-205}$ | $L_{b31}$ |
| 2-41 | $L_{a-36}$ | $L_{b57}$ | 2-42 | $L_{a-37}$ | $L_{b57}$ |
| 2-43 | $L_{a-41}$ | $L_{b57}$ | 2-44 | $L_{a-43}$ | $L_{b57}$ |
| 2-45 | $L_{a-45}$ | $L_{b57}$ | 2-46 | $L_{a-53}$ | $L_{b57}$ |
| 2-47 | $L_{a-57}$ | $L_{b57}$ | 2-47 | $L_{a-72}$ | $L_{b57}$ |
| 2-49 | $L_{a-119}$ | $L_{b57}$ | 2-50 | $L_{a-128}$ | $L_{b57}$ |
| 2-51 | $L_{a-129}$ | $L_{b57}$ | 2-52 | $L_{a-130}$ | $L_{b57}$ |
| 2-53 | $L_{a-133}$ | $L_{b57}$ | 2-54 | $L_{a-136}$ | $L_{b57}$ |
| 2-55 | $L_{a-137}$ | $L_{b57}$ | 2-56 | $L_{a-141}$ | $L_{b57}$ |
| 2-57 | $L_{a-146}$ | $L_{b57}$ | 2-58 | $L_{a-181}$ | $L_{b57}$ |
| 2-59 | $L_{a-194}$ | $L_{b57}$ | 2-60 | $L_{a-195}$ | $L_{b57}$ |
| 2-61 | $L_{a-204}$ | $L_{b57}$ | 2-62 | $L_{a-205}$ | $L_{b57}$ |
| 2-77 | $L_{a-36}$ | $L_{b88}$ | 2-78 | $L_{a-37}$ | $L_{b88}$ |
| 2-79 | $L_{a-41}$ | $L_{b88}$ | 2-80 | $L_{a-43}$ | $L_{b88}$ |
| 2-81 | $L_{a-45}$ | $L_{b88}$ | 2-82 | $L_{a-53}$ | $L_{b88}$ |
| 2-83 | $L_{a-57}$ | $L_{b88}$ | 2-84 | $L_{a-72}$ | $L_{b88}$ |
| 2-85 | $L_{a-119}$ | $L_{b88}$ | 2-86 | $L_{a-128}$ | $L_{b88}$ |
| 2-87 | $L_{a-129}$ | $L_{b88}$ | 2-88 | $L_{a-130}$ | $L_{b88}$ |
| 2-89 | $L_{a-133}$ | $L_{b88}$ | 2-90 | $L_{a-136}$ | $L_{b88}$ |
| 2-91 | $L_{a-137}$ | $L_{b88}$ | 2-92 | $L_{a-141}$ | $L_{b88}$ |
| 2-93 | $L_{a-146}$ | $L_{b88}$ | 2-94 | $L_{a-181}$ | $L_{b88}$ |
| 2-95 | $L_{a-194}$ | $L_{b88}$ | 2-96 | $L_{a-195}$ | $L_{b88}$ |
| 2-97 | $L_{a-204}$ | $L_{b88}$ | 2-98 | $L_{a-205}$ | $L_{b88}$ |
| 2-113 | $L_{a-36}$ | $Lb_{122}$ | 2-114 | $L_{a-37}$ | $L_{b122}$ |
| 2-115 | $L_{a-41}$ | $Lb_{122}$ | 2-116 | $L_{a-43}$ | $L_{b122}$ |
| 2-117 | $L_{a-45}$ | $Lb_{122}$ | 2-118 | $L_{a-53}$ | $L_{b122}$ |
| 2-119 | $L_{a-57}$ | $Lb_{122}$ | 2-120 | $L_{a-72}$ | $L_{b122}$ |
| 2-121 | $L_{a-119}$ | $Lb_{122}$ | 2-122 | $L_{a-128}$ | $L_{b122}$ |
| 2-123 | $L_{a-129}$ | $Lb_{122}$ | 2-124 | $L_{a-130}$ | $L_{b122}$ |
| 2-125 | $L_{a-133}$ | $Lb_{122}$ | 2-126 | $L_{a-136}$ | $L_{b122}$ |
| 2-127 | $L_{a-137}$ | $Lb_{122}$ | 2-128 | $L_{a-141}$ | $L_{b122}$ |
| 2-129 | $L_{a-146}$ | $Lb_{122}$ | 2-130 | $L_{a-181}$ | $L_{b122}$ |
| 2-131 | $L_{a-194}$ | $Lb_{122}$ | 2-132 | $L_{a-195}$ | $L_{b122}$ |
| 2-133 | $L_{a-204}$ | $Lb_{122}$ | 2-134 | $L_{a-205}$ | $L_{b122}$ |
| 2-149 | $L_{a-36}$ | $L_{b126}$ | 2-150 | $L_{a-37}$ | $L_{b126}$ |
| 2-151 | $L_{a-41}$ | $L_{b126}$ | 2-152 | $L_{a-43}$ | $L_{b126}$ |
| 2-153 | $L_{a-45}$ | $L_{b126}$ | 2-154 | $L_{a-53}$ | $L_{b126}$ |
| 2-155 | $L_{a-57}$ | $L_{b126}$ | 2-156 | $L_{a-72}$ | $L_{b126}$ |
| 2-157 | $L_{a-119}$ | $L_{b126}$ | 2-158 | $L_{a-128}$ | $L_{b126}$ |
| 2-159 | $L_{a-129}$ | $L_{b126}$ | 2-160 | $L_{a-130}$ | $L_{b126}$ |
| 2-161 | $L_{a-133}$ | $L_{b126}$ | 2-162 | $L_{a-136}$ | $L_{b126}$ |
| 2-163 | $L_{a-137}$ | $Lb_{126}$ | 2-164 | $L_{a-141}$ | $L_{b126}$ |
| 2-165 | $L_{a-146}$ | $L_{b126}$ | 2-166 | $L_{a-181}$ | $L_{b126}$ |
| 2-167 | $L_{a-194}$ | $L_{b126}$ | 2-168 | $L_{a-195}$ | $L_{b126}$ |
| 2-169 | $L_{a-204}$ | $L_{b126}$ | 2-170 | $L_{a-205}$ | $L_{b126}$ |
| 2-185 | $L_{a-36}$ | $L_{b212}$ | 2-186 | $L_{a-37}$ | $L_{b212}$ |
| 2-187 | $L_{a-41}$ | $L_{b212}$ | 2-188 | $L_{a-43}$ | $L_{b212}$ |
| 2-189 | $L_{a-45}$ | $L_{b212}$ | 2-190 | $L_{a-53}$ | $L_{b212}$ |
| 2-191 | $L_{a-57}$ | $L_{b212}$ | 2-192 | $L_{a-72}$ | $L_{b212}$ |
| 2-193 | $L_{a-119}$ | $L_{b212}$ | 2-194 | $L_{a-128}$ | $L_{b212}$ |
| 2-195 | $L_{a-129}$ | $L_{b212}$ | 2-196 | $L_{a-130}$ | $L_{b212}$ |
| 2-197 | $L_{a-133}$ | $L_{b212}$ | 2-198 | $L_{a-136}$ | $L_{b212}$ |
| 2-199 | $L_{a-137}$ | $L_{b212}$ | 2-200 | $L_{a-141}$ | $L_{b212}$ |
| 2-201 | $L_{a-146}$ | $L_{b212}$ | 2-202 | $L_{a-181}$ | $L_{b212}$ |
| 2-203 | $L_{a-194}$ | $L_{b212}$ | 2-204 | $L_{a-195}$ | $L_{b212}$ |
| 2-205 | $L_{a-204}$ | $L_{b212}$ | 2-206 | $L_{a-205}$ | $L_{b212}$ |

wherein the Compound 2-217 to Compound 2-223, Compound 2-229 to Compound 2-237, Compound 2-243 to Compound 2-251, Compound 2-257 to Compound 2-265, Compound 2-271 to Compound 2-279, Compound 2-285 to Compound 2-293 and Compound 2-299 to Compound 2-300 have the structure of $Ir(L_a)_2(L_b)$, wherein the two $L_a$ are different, and the $L_a$ and $L_b$ respectively correspond to structures listed in the following table:

| Compound No. | $L_a$ | $L_a$ | $L_b$ | Compound No. | $L_a$ | $L_a$ | $L_b$ |
|---|---|---|---|---|---|---|---|
| 2-217 | $L_{a-133}$ | $L_{a-41}$ | $L_{b31}$ | 2-218 | $L_{a-133}$ | $L_{a-43}$ | $L_{b31}$ |
| 2-219 | $L_{a-133}$ | $L_{a-136}$ | $L_{b31}$ | 2-220 | $L_{a-133}$ | $L_{a-137}$ | $L_{b31}$ |
| 2-221 | $L_{a-133}$ | $L_{a-146}$ | $L_{b31}$ | 2-222 | $L_{a-133}$ | $L_{a-204}$ | $L_{b31}$ |
| 2-223 | $L_{a-133}$ | $L_{a-205}$ | $L_{b31}$ | | | | |
| 2-229 | $L_{a-41}$ | $L_{a-136}$ | $L_{b31}$ | 2-230 | $L_{a-41}$ | $L_{a-137}$ | $L_{b31}$ |
| 2-231 | $L_{a-133}$ | $L_{a-41}$ | $L_{b57}$ | 2-232 | $L_{a-133}$ | $L_{a-43}$ | $L_{b57}$ |
| 2-233 | $L_{a-133}$ | $L_{a-136}$ | $L_{b57}$ | 2-234 | $L_{a-133}$ | $L_{a-137}$ | $L_{b57}$ |
| 2-235 | $L_{a-133}$ | $L_{a-146}$ | $L_{b57}$ | 2-236 | $L_{a-133}$ | $L_{a-204}$ | $L_{b57}$ |
| 2-237 | $L_{a-133}$ | $L_{a-205}$ | $L_{b57}$ | | | | |
| 2-243 | $L_{a-41}$ | $L_{a-136}$ | $L_{b57}$ | 2-244 | $L_{a-41}$ | $L_{a-137}$ | $L_{b57}$ |
| 2-245 | $L_{a-133}$ | $L_{a-41}$ | $L_{b88}$ | 2-246 | $L_{a-133}$ | $L_{a-43}$ | $L_{b88}$ |
| 2-247 | $L_{a-133}$ | $L_{a-136}$ | $L_{b88}$ | 2-248 | $L_{a-133}$ | $L_{a-137}$ | $L_{b88}$ |
| 2-249 | $L_{a-133}$ | $L_{a-146}$ | $L_{b88}$ | 2-250 | $L_{a-133}$ | $L_{a-204}$ | $L_{b88}$ |
| 2-251 | $L_{a-133}$ | $L_{a-205}$ | $L_{b88}$ | | | | |
| 2-257 | $L_{a-41}$ | $L_{a-136}$ | $L_{b88}$ | 2-258 | $L_{a-41}$ | $L_{a-137}$ | $L_{b88}$ |
| 2-259 | $L_{a-133}$ | $L_{a-41}$ | $L_{b122}$ | 2-260 | $L_{a-133}$ | $L_{a-43}$ | $L_{b122}$ |
| 2-261 | $L_{a-133}$ | $L_{a-136}$ | $L_{b122}$ | 2-262 | $L_{a-133}$ | $L_{a-137}$ | $L_{b122}$ |
| 2-263 | $L_{a-133}$ | $L_{a-146}$ | $L_{b122}$ | 2-264 | $L_{a-133}$ | $L_{a-204}$ | $L_{b122}$ |
| 2-265 | $L_{a-133}$ | $L_{a-205}$ | $L_{b122}$ | | | | |
| 2-271 | $L_{a-41}$ | $L_{a-136}$ | $L_{b122}$ | 2-272 | $L_{a-41}$ | $L_{a-137}$ | $L_{b122}$ |
| 2-273 | $L_{a-133}$ | $L_{a-41}$ | $L_{b126}$ | 2-274 | $L_{a-133}$ | $L_{a-43}$ | $L_{b126}$ |
| 2-275 | $L_{a-133}$ | $L_{a-136}$ | $L_{b126}$ | 2-276 | $L_{a-133}$ | $L_{a-137}$ | $L_{b126}$ |
| 2-277 | $L_{a-133}$ | $L_{a-146}$ | $L_{b126}$ | 2-278 | $L_{a-133}$ | $L_{a-204}$ | $L_{b126}$ |
| 2-279 | $L_{a-133}$ | $L_{a-205}$ | $L_{b126}$ | | | | |
| 2-285 | $L_{a-41}$ | $L_{a-136}$ | $L_{b126}$ | 2-286 | $L_{a-41}$ | $L_{a-137}$ | $L_{b126}$ |
| 2-287 | $L_{a-133}$ | $L_{a-41}$ | $L_{b212}$ | 2-288 | $L_{a-133}$ | $L_{a-43}$ | $L_{b212}$ |
| 2-289 | $L_{a-133}$ | $L_{a-136}$ | $L_{b212}$ | 2-290 | $L_{a-133}$ | $L_{a-137}$ | $L_{b212}$ |
| 2-291 | $L_{a-133}$ | $L_{a-146}$ | $L_{b212}$ | 2-292 | $L_{a-133}$ | $L_{a-204}$ | $L_{b212}$ |
| 2-293 | $L_{a-133}$ | $L_{a-205}$ | $L_{b212}$ | | | | |
| 2-299 | $L_{a-41}$ | $L_{a-136}$ | $L_{b212}$ | 2-300 | $L_{a-41}$ | $L_{a-137}$ | $L_{b212}$. |

25. The electroluminescent device of claim 23, wherein the second compound has the structure of $Ir(L_a)_2(L_b)$, wherein $L_a$ is, at each occurrence identically or differently, selected from any one or any two of the group consisting of $L_{a-35}$ to $L_{a-223}$ and $L_b$ is selected from any one of the group consisting of $L_{b1}$ to $L_{b322}$.

26. The electroluminescent device of claim 1, wherein the organic layer is a light-emitting layer, the first compound is a host material, and the second compound is a light-emitting material.

27. The electroluminescent device of claim 26, wherein the device emits red light or white light.

28. A display assembly, comprising the electroluminescent device of claim 1.

29. The electroluminescent device of claim 1, wherein R and $R_f$ are, at each occurrence identically or differently, selected from the group consisting of: hydrogen, deuterium, halogen, substituted or unsubstituted aryl having 6 to 30 carbon atoms, substituted or unsubstituted heteroaryl having 3 to 30 carbon atoms, a cyano group, a hydroxyl group, a sulfanyl group and combinations thereof.

30. A compound combination, comprising a first compound and a second compound, wherein the first compound has a structure of H-L-E;

H has a structure represented by Formula 1-a:

Formula 1-a

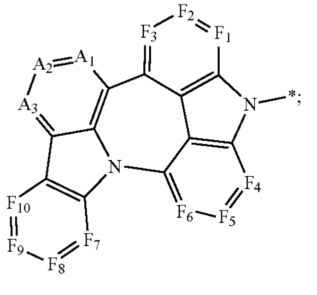

in Formula 1-a, $A_1$, $A_2$ and $A_3$ are, at each occurrence identically or differently, selected from CR, and $F_1$ to $F_{10}$ are, at each occurrence identically or differently, selected from $CR_f$;

E has a structure represented by Formula 2-d:

Formula 2-d

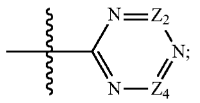

in Formula 2-d, $Z_2$ and $Z_4$ are each independently selected from $CR_z$;

L is selected from substituted or unsubstituted arylene having 6 to 30 carbon atoms, substituted or unsubstituted heteroarylene having 3 to 30 carbon atoms or a combination thereof;

R, $R_f$ and $R_z$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, a cyano group, a hydroxyl group, a sulfanyl group, and combinations thereof; and adjacent substituents R, $R_f$ can be optionally joined to form a ring;

the second compound is a metal complex having a general formula of $Ir(L_a)_2(L_b)$;

wherein $L_a$ and $L_b$ are a first ligand and a second ligand coordinated to the Ir, respectively;

$L_a$ and $L_b$ can be optionally joined to form a multidentate ligand;

the multiple $L_a$ may be the same or different;

the $L_a$ has a structure represented by Formula 3-1 or Formula 3-3:

Formula 3-1

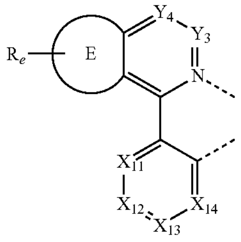

Formula 3-3

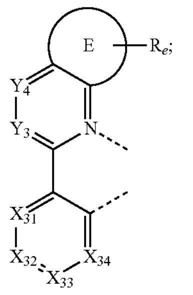

wherein, the ring E is selected from a benzene ring;

$R_e$ represents, at each occurrence identically or differently, mono-substitution, multiple substitutions or non-substitution;

$X_{11}$ to $X_{14}$ are, at each occurrence identically or differently, selected from $CR_{x1}$; $X_{31}$ to $X_{34}$ are, at each occurrence identically or differently, selected from $CR_{x3}$;

$Y_3$ and $Y_4$ are, at each occurrence identically or differently, selected from $CR_d$;

$R_{x1}$, $R_{x3}$, $R_d$ and $R_e$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, a cyano group, an isocyano group, a hydroxyl group, a sulfanyl group, and combinations thereof;

adjacent substituents $R_{x1}$, $R_d$ and $R_e$ can be optionally joined to form a ring;

when $R_{x3}$ is selected from substituted or unsubstituted alkyl having 1 to 20 carbon atoms, substituted or unsubstituted cycloalkyl having 3 to 20 ring carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, or substituted or unsubstituted amino having 0 to 20 carbon atoms, adjacent substituents $R_{x3}$ can be optionally joined to form a ring;

$L_b$ has the following structure:

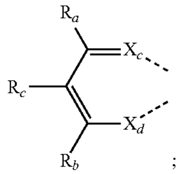

;

$R_a$, $R_b$ and $R_c$ represent, at each occurrence identically or differently, mono-substitution, multiple substitutions or non-substitution;

$X_c$ and $X_d$ are O;

$R_a$, $R_b$ and $R_c$, are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, a cyano group, and combinations thereof;

in structures of $L_b$, adjacent substituents $R_a$, $R_b$, $R_c$, can be optionally joined to form a ring;

and, the following case is not comprised: the first compound is

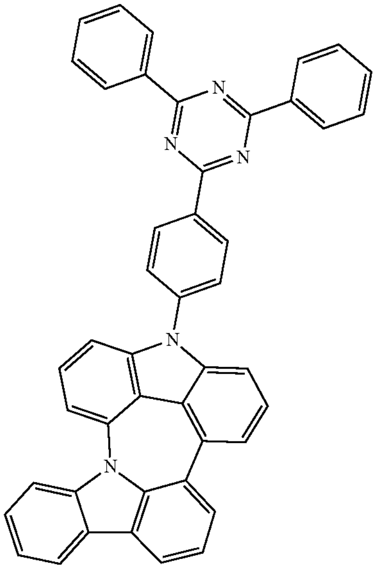 [SMILES: c1ccc(-c2nc(-c3ccccc3)nc(-c3ccc(-n4c5cccc6c7cccc8c9ccccc9n(c9cccc4c9c65)c78)cc3)n2)cc1]

while the second compound is

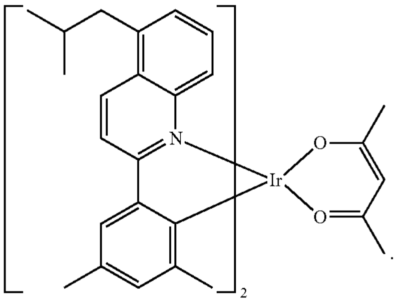

* * * * *